US007279164B2

(12) United States Patent
Hermida Cruz et al.

(10) Patent No.: US 7,279,164 B2
(45) Date of Patent: Oct. 9, 2007

(54) CHIMERIC PROTEINS THAT INDUCE EFFECTS DIRECTED AGAINST VIRUSES

(75) Inventors: Lisset Hermida Cruz, Ciudad de La Habana (CU); Rayner Rodriguez Diaz, Ciudad de La Habana (CU); Laura Lazo Vazquez, Ciudad de La Habana (CU); Aida Zulueta Morales, Ciudad de La Habana (CU); Carlos Lopez Abarrategui, Ciudad de La Habana (CU); Iris Valdes Prado, Ciudad de La Habana (CU); Ricardo de la C. Silva Rodriguez, Ciudad de La Habana (CU); Glay Chinea Santiago, Ciudad de La Habana (CU); Gerardo Enrique Guillen Nieto, Ciudad de La Habana (CU); Maria Guadalupe Guzman Tirado, Ciudad de La Habana (CU); Beatriz de la Caridad Sierra Vazquez, Ciudad de La Habana (CU); Raul Rafael Espinosa Perez, Ciudad de La Habana (CU)

(73) Assignee: Centro de Ingenieria Genetica y Biotecnologia, Ciudad de La Habana (CU)

( * ) Notice: Subject to any disclaimer, the term of this patent is extended or adjusted under 35 U.S.C. 154(b) by 71 days.

(21) Appl. No.: 10/484,114

(22) PCT Filed: Jul. 12, 2002

(86) PCT No.: PCT/CU02/00006

§ 371 (c)(1), (2), (4) Date: Jun. 7, 2004

(87) PCT Pub. No.: WO03/008571

PCT Pub. Date: Jan. 30, 2003

(65) Prior Publication Data

US 2004/0234951 A1 Nov. 25, 2004

(30) Foreign Application Priority Data

Jul. 16, 2001 (CU) .................................... 0172/01

(51) Int. Cl.
*A61K 39/00* (2006.01)
*A61K 39/12* (2006.01)

(52) U.S. Cl. ............................... 424/185.1; 424/192.1; 424/218.1

(58) Field of Classification Search ............ 424/147.1, 424/184.1, 185.1, 186.1, 199.1, 202.1, 204.1, 424/192.1, 218.1; 435/5; 536/23.72
See application file for complete search history.

(56) References Cited

FOREIGN PATENT DOCUMENTS

EP 0474313 A2 3/1992

(Continued)

OTHER PUBLICATIONS

Chaturvedi et al., "Dengue vaccines: Problems and Prospects," Indian J Med. Res., vol. 121, May 2005, pp. 639-652.*

(Continued)

*Primary Examiner*—Bruce R. Campell
*Assistant Examiner*—M. Franco Salvoza
(74) *Attorney, Agent, or Firm*—Hoffman & Baron, LLP

(57) ABSTRACT

The present invention is related to the obtaining of chimeric chains coding for proteins capable of inducing, in the recipient, a serotype-specific and protective humoral immune response against the infection by the Dengue virus, thus eliminating the effects of the serotype-nonespecific viral immunoenhancement that causes hemorrhagies and clinical complications described for this kind of pathology. These chimeric chains of nucleic acids are composed by the specific combination of fragments belonging to the gene of a mutated protein from *Neisseria meningitidis* with dehydrogenase activity and fragments that codify for a region of the envelope (E) protein from the Dengue virus which, when inserted to an expression vector, give rise to chimeric proteins with particular properties. The resultant chimeric molecules from this invention are applicable to the pharmaceutical industry for the obtaining of vaccine preparations and diagnostic means of high serotype-specificity to be used in humans.

7 Claims, 13 Drawing Sheets

FOREIGN PATENT DOCUMENTS

| | | | |
|---|---|---|---|
| WO | WO96/37221 | | 11/1996 |
| WO | WO97/26359 | | 7/1997 |
| WO | WO9831814 | A1 * | 7/1998 |
| WO | WO 00/66791 | | 11/2000 |

OTHER PUBLICATIONS

Perez et al., "Safety and preliminary immunogenicity of the recombinant outer membrane protein P64K of *Neiseria meningitis* in human volunteers," Biotechnol. Appl. Biochem. 34, 121-125 (2001).*

Pugachev et al., "New developments in flavivirus vaccines with special attention to yellow fever," Curr Opin Infect Dis 18:387-394 (2005).*

Silva et al., "Characterization of the lpdA gene from *Neisseria meningitidis* by polymerase chain reaction, restriction fragment length polymorphism and sequencing," FEMS Microbiology Letters 174 (1999)191-199.*

Srivastava et al., "Mice immunized with a dengue type 2 virus E and NS1 fusion protein made in *Escherichia coli* are protected against lethal dengue virus infection," Vaccine vol. 13, No. 13 (1995).*

Blok, J., et al., "Variation of the Nucleotide and Encoded Amino Acid Sequences of the Envelope Gene from Eight Dengue-2 Viruses", Archives of Virology 1989, 105(1-2):39-53.

Lanciotti, Robert S., et al., "Molecular evolution and epidemiology of dengue-3 viruses", Journal of General Virology 1994, 75(1):65-75.

Lanciotti, Robert S., et al., "Molecular evolution and phylogeny of dengue-4 viruses", Journal of General Virology 1997, 78(9):2279-2286.

Silva, Ricardo, et al., "Characterisation of the lpdA gene from *Neisseria meningitidis* by polymerase chain reaction, restriction fragment length polymorphism and sequencing", FEMS Microbiology Letters May 1999, 174(1):191-199.

Tettelin, Herve, et al., "Complete Genome Sequence of *Neisseria meningitidis* Serogroup B Strain MC58", SCIENCE 2000, 287(5459):1809-1815.

Wang, Eryu, et al., "Evolutionary Relationships of Endemic/Epidemic and Sylvatic Dengue Viruses", Journal of Virology 2000, 74(7):3227-3234.

* cited by examiner

CHIMERIC PROTEINS THAT INDUCE EFFECTS DIRECTED AGAINST VIRUSES

This application is a U.S. National Phase Application of International Application No. PCT/CU02/00006 filed on Jul. 12, 2002. The specification of International Application No. PCT/CU02/00006 is hereby incorporated by reference.

This application asserts priority to Cuban Application No. CU 2001-0172 filed on Jul. 16, 2001. The specification of Cuban application No. CU 2001-0172 is hereby incorporated by reference.

FIELD OF THE INVENTION

The present invention is related with the field of the biotechnology and the pharmaceutical industry, in particular with the obtaining of chimeric nucleotide chains which, when introduced into an expression vector, give rise to proteins able to elicit a serotype-specific humoral immune response and protection against the Dengue virus infection; quoted from now on as DEN, avoiding the effects of the serotype-specific viral immunoamplification, causing hemorrhages and clinical complications described in this type of pathology.

BACKGROUND OF THE INVENTION

The Dengue virus (DEN), is a coated virus whose lipid membrane contains two of its three structural proteins: the envelope protein (E) and the membrane protein (M). The E protein covers an icosaedric nucleocapsid composed by the third of its structural proteins, the core protein. This virus belongs to the Flaviviridae family and four different serotypes exist. Its transmission to the man is carried out through the mosquito *Aedes aegypti* that belongs to the Stegomia family. The disease produced in the human for this virus was considered as benign and was described as Dengue Fever or Classical Dengue (DF) until the appearance of a more serious modality and sometimes lethal, characterized by hemorrhagic fever and shock, denominated: Hemorrhagic Dengue Fever and Dengue Shock Syndrome (HDF/DSS) (Hammon WMc. New hemorrhagic fever in children in the Philippines and Thailand. Trans Assoc Physicians 1960; 73: 140–155). Several epidemiological studies have been carried out evidencing as a risk factor the sequential infection of two different viral serotypes (Kouri G P, Guzman M G, Brave J R. Why dengue hemorrhagic fever in Cuba) 2. An integral analysis. Trans Roy Soc Trop Med Hyg 1987; 72: 821–823). This phenomenon is explained by the immunoenhancement, which is based on an increase of the viral infection by increasing the entrance of the virus-antibody complex to the cell through the Fc receptors of the target cell (monocytes) (haistead SB. Pathogenesis of dengue: challenges to molecular biology. Science 1988; 239: 476–481).

Different technologies have been developed to produce live attenuated vaccines, but at present there exist multiple unsolved issues on the possible benefits of these vaccines, since they could revert to the virulence, viral interference and inter-genomic recombination. Alternately, recombinant antigens can be obtained as possible components of a subunit vaccine (Feighny, R., Borrous, J. and Putnak R. Dengue type-2 virus envelope protein made using recombinant baculovirus protects mice against virus challenge. Am. J. Trop. Med. Hyg. 1994. 50(3). 322–328; Deubel, V., Staropoli, I., Megret, F., et al. Affinity-purified dengue-2 virus envelope glycoprotein induces neutralizing antibodies and protective immunity in mice. Vaccine. 1997. 15, 1946–1954).

The main antigen of the virus is the envelope protein DENe. This protein is the major component of the viral surface and is thought to mediate the binding of the virus to the cellular receptor (A Heinz F X, Berge R, Tuma W et al. A topological and functional model of epitopes on the structural glycoprotein of tick-borne encephalitis virus defined by monoclonal antibodies. Virology. 1983; 126: 525). This protein has structural homology with that of the tick borne encephalitis virus (TBE) (Rey, F. A., Heinz, F. X., Mandl, C., et al. The envelope glycoprotein from tick borne encephalitis virus at 2 A° resolution. Nature 1995; 375: 291–298) and it is also structurally conserved among serotypes.

The insect cells constitute one of the systems most used for the expression of diverse heterologous genes that employ the baculovirus system as vectors. These vectors have been used for the expression of several combinations of structural and nonstructural proteins of the Encephalitis Japanese virus (JEV), DEN-1, DEN-2 and DEN4, (Matsuura Y, Miyamoto M, Soto T et al. Characterization of japanese encephalitis virus envelope protein expressed by recombinant baculoviruses. Virology 1989; 173: 677–682; Deubel V, Bordier M, Megret F et al. Processing, secretion and immunoreactivity of carboxy terminally truncated dengue-2 envelope proteins expressed in insect cell by recombinant baculoviruses. Virology 1991; 180: 440–447; Putnak R, Feighny R, Burrous J et al. Dengue 1 virus envelope glycoprotein gene expressed in recombinant baculovirus elicit virus neutralization antibodies in mice and protects them from virus challenge. Am J Trop Med Hyg 1991; 45: 159–167; Feighny R, Burrous J, Putnak R. Dengue type 2 virus envelope protein made using recombinant baculovirus protects mice against virus challenge. Am J Trop Med Hyg 1994; 50: 322–328). Another system used has been the cells of *Drosophila melanogaster* expressing different variants of the E protein (PCT/US96/07627). In spite of obtaining an appropriate functional response, upon using the proteins expressed in these systems, they imply a high cost for the development of scale-up production processes; therefore, the expression in yeast has been an alternative to produce recombinant structural proteins of flavivirus. However, in the case of the DENe protein, expressed in *Pichia pastoris* (PCT/US96/07627; Sugrue R. J., Fu H., Howe J., Chan Y. Expression of the Dengue virus structural proteins in *Pichia pastoris* leads to the generation of virus-like particles. J. Virol. 1997. 78, 1861–1866), the levels of expression are low, either secreted or intracellularly, hindering the purification process.

In parallel, several variants of the DENe protein have been obtained in bacteria. One of them was the C-terminal portion of the E protein of the JEV fused to a protein of the Tryptophan metabolism (TrpE) of *E. coli*. This protein was produced as inclusion bodies and was recognized by neutralizing monoclonal antibodies (Mabs) using immunodetection techniques. However, pure preparations of this protein were unable to develop neutralizing antibodies and to protect against viral challenge (Mason P. W., Zogel M. V., Semproni A. R., et al. The antigenic structure of dengue type I virus envelope and NS1 protein expressed in *E. coli*. J Gen Virol. 1990. 71: 2107–2114). In addition, another construction was made (Srivastava A. K., Morita K., Matsuo S., et al. Japanese encephalitis virus fusion protein with protein A expressed in *E. coli* confers protection in mice. Microbiol Immunol. 1991. 35: 863–870), that contains the protein A of *Staphylococcus aurius* fused to the C-terminal fragment of the E protein, followed by the N-terminal segment of the nonstructural protein of the JEV, the NS1. In this case the fused protein was soluble, facilitating its purification by affinity chromatography. Upon immunizing mice with this pure protein high neutralizing antibodies titers were obtained, which also inhibited haemagglutination and protected against the viral challenge with the JEV. Similar results were obtained using the DENe region of the DEN-2 fused to the protein A of *S. aureus* (Srivastava A. K., Putnak R. J., Warren R. L., Hoke C. H. Mice immunized with a dengue type 2 virus E and NS1 fusion protein made in *Escherichia coli* are protected against lethal dengue virus infection. Vaccine. 1995. 13: 1251–1258); however, it is not possible to use these preparations in humans due to the presence of the protein A, which has shown a high affinity for the human immunoglobulin G (IgG).

Finally, it has been reported a fusion protein that contains the B domain of the DENe protein of DEN-2 and the maltose binding protein (MBP) of *E. coli* (Simmons M., Nelson W. M., Wu S. J., Hayes C. G. Evaluation of the protective efficacy of a recombinant dengue envelope B domain fusion protein against dengue 2 virus infection in mice. Am J Trop Med Hyg. 1998. 58: 655-662) denominated MBP-DomB. This protein variant was immunogenic in mice and elicited neutralizing antibodies.

SUMMARY OF THE INVENTION

In our case, the subject of this invention relies on the obtaining of chimeric sequences, as for instance, in the first case, the sequence coding for a region of the DENe protein linked to the N-terminal fragment of a mutated protein with dehydrogenase activity (MDH) from *Neisseria meningitidis*; in the second case, the sequence coding for a region of the DENe protein linked to the entire gene of the MDH protein in two different positions, and in the third case, the chimeric sequences are formed by two fragments of the DENe protein from two different viral serotypes fused to the same gene coding for the MDH protein. These chimeric chains when inserted into a suitable vector, give rise to insoluble chimeric proteins within the bacterium's cytoplasm. These proteins are then capable to elicit high levels of neutralizing antibodies against DEN, inhibitors of the viral hemagglutination and to protect immunized mice against viral challenge.

With regards to the insolubility of the aforementioned proteins, an easy scale-up folding process was achieved in vitro, as well as the expression and purification processes which were superior to those used by Simmons et al, 1998. On the other hand, the serotype specificity of the antibodies is demonstrated, generated by immunization of mice with these proteins, at the level of neutralization, inhibition of hemaglutination and ELISA, using doses lower than those employed by Simmons et al, 1998. This fact constitutes the first report on the expression of insoluble DENe proteins in *E. coli* capable of stimulating a functionl immune response.

In addition, considering the results obtained with the dimeric variant, it is possible to generate serotype-specific antibodies with the same molecule for two different viral serotypes, capable of neutralizing viral infection and protect mice against viral challenge. Concerning the MDH protein, a search for homology with other sequences was done in the EMBL data base, revealing that the first 110 amino acids are highly similar to the lipoic binding domain region and the flexible hinge of the dihydrolipoamide acetyltransferase (E2 enzyme of the pyruvate dehydrogenase complex and α-cetoglutarate dehydrogenase), and the rest of the protein is highly similar to the lipoamide dehydrogenase (LPDH), enzyme E3 of said complexes (Stephens, P. E; H. M. Darlinson, and J. R. Guest., 1983. The Pyruvate dehydrogenase complex of *E. coli*. Eur. J. Biochem. 133:155–162.

On the other hand, it was also found that patients with Primary Biliary Cirrhosis (PBC) produced anti-mitochondrial autoantibodies, specific for the lipoic acid binding site, common among these proteins (Gershwin M E, Mackay I R, Sturgess A, Coppel R L. Identification and specificity of a cDNA encoding the 70 KDa mitochondrial antigen recognized in primary biliary cirrhosis. J Immunol 1987;138: 3525–31). Therefore, we decided to mutate this region within the protein to avoid any autoimmune response when immunized in humans as chimeric proteins. The mutated MDH protein of our invention was used in a Phase I clinical trial and showed to be safe and immunogenic in humans, and also was not recognized by sera of patients with PBC (Pérez, A., F. Dickinson, Z. Cinza, A. Ruiz, T. Serrano, J. Sosa, S. González, Y. Gutiérrez, C. Nazábal, O. Gutiérrez, D. Guzmán, M. Diaz, M. Delgado, E. Caballero, G. Sardiñas, A. Alvarez, A. Martin, G. Guillén, R. Silva. Safety and preliminary immunogenicity of the recombinant outer membrane protein of *Neisseria meningitidis* in human volunteers. Biotech. Appl. Biochem. 34: 121–125). However, the possible use of the MBP in humans has not been demonstrated yet (Simmons M., Nelson W. M., Wu S. J., Hayes C. G. Evaluation of the protective efficacy of a recombinant dengue envelope B domain fusion protein against dengue 2 virus infection in mice. Am J Trop Med Hyg. 1998. 58: 655–662).

DETAILED DESCRIPTION OF THE INVENTION

In this invention is described the obtaining of chimeric nucleotide chains that when introduced into an expression vector, give rise to chimeric proteins capable of inducing a serotype-specific humoral immune response and protecting against the infection by Dengue virus, as for instance, the sequence coding for a region of the DENe protein from each one of the viral serotypes of the Dengue virus, linked to the N-terminal fragment of a mutated protein with dehydrogenase activity (MDH) from *Neisseria meningitidis*; in the second case, the sequence coding for a region of the DENe protein linked to the entire gene of the MDH protein in two different positions: within one site of the sequence coding for the structural domain of the MDH protein (lipoic acid binding domain and the 3' end of the gen), and in the third case, the chimeric sequences are formed by two fragments of the DENe protein from two different viral serotypes, DEN-2 and DEN-4, in two different positions of the MDH gen: one within a particular site of the sequence coding for the lipoic acid binding domain (serotype 4) and the other in the 3' end of the MDH gen (serotype 2). This was called a dimeric construct.

This chimeric proteins were obtained insoluble within the bacterium's cytoplasm. A purification process by immobilazed metal affinity chromatography (IMAC) was done which led to obtain pure proteins for immunogenicity studies.

When antigenicity results were analyzed a strong recognition of all the recombinant chimeric proteins for the hyperimmune ascitic liquids (HMAF) anti-DEN was demonstrated, being higher for the case of the fusion to the entire MDH gene, which evidences a positive effect on the folding of the region from the DENe protein given by the MDH. In the cases where the serotype 2 was used, all recombinant proteins obtained were recognized by a serotype-specific neutralizing antibody (3H5), being also higher for the case of the fusion to the entire MDH gene, as well as in the dimeric protein. It was also observed that the recognition for the HMAF from the homologous serotype in each case was significantly higher than the recognition for the HMAF from the heterologous serotypes, evidencing the exposure of serotype-specific epitopes and permitting thus its use as a diagnostic mean for Dengue and serotyping.

When all the recombinant chimeric proteins were immunized in mice a neutralizing and protective response was obtained. Highest neutralizing titers were obtained with the sequences fused to the entire gene of the MDH and with the dimeric protein, independently of the position of the fragment from the DENe protein. This showed an immunopotentiator effect of the immune response mediated by the MDH that can be explained by the influence in the folding of the DENe protein reflected in the antigenicity results obtained. It was also demonstrated for the first time, and contrary to the previous state of the art, that the insolubility of these proteins do not affect the capacity of generating a suitable immune response.

The immune response produced in all the cases was serotype-specific (antibodies against the immunized homologous serotype) in the viral neutralization, the hemoagglutination inhibition and ELISA. The generation of serotype-specific antibodies means that they are not capable to recognize antigenic determinants from virus of heterologous serotypes that favour the immunoenhacement phenomenum. This characteristic is of great importance for the development of a vaccine candidate against the Dengue virus since the recognition of antibodies to heterologous serotypes could be one of the causes for the Hemorrhagic Dengue Fever (HDF).

Besides it was showed the induction of antibodies against two viral serotypes after immunization with just one of the chimeric proteins, which permits the formulation of a vaccine candidate against the four serotypes, using only two of our available recombinant chimeric proteins.

The obtaining of the mutant MDH protein consisted of the elimination of the lipoic acid binding site in the sequence ETDKAT, based on the covalent binding of this fatty acid with the epsilon-amine groups of lysine (K) (Tuaillon N, Andre C, Briand J P et al. A lipoyl synthetic octadecapeptide of dihydrolipoamide acetyltransferase specifically recognized by anti-M2 autoantibodies in Primary Biliary Cirrhosis. J Immunol 1992; 148:445-50).

The mutagenesis was done by using PCR with a pair of primers to amplify the N-terminal region (from the start codon of the lpdA gene until the lipoic acid binding site, 135 bp) and the C-terminal of the protein (from the lipoic acid binding site until the 3' end of the gene); thus, being eliminated the possibility to generate autoimmune reactions, as demonstrated in the human clinical trials.

Deposit of the Biological Material

Plasmids PLL1, PLL2, PLL3, PLH1, PLH2, PLH3,PAZ1, PAZ2, PAZ3, PID1, PID2 and PID3 were deposited according to the Budapest Treaty in the Belgian Coordinated collection of Microorganism—BCCM™, LMBP-COLLECTION, on Jun. 20, 2003 and under the access numbers LMBP 4564, LMBP 4565, LMBP 4566, LMBP 4561, LMBP 4562, LMBP 4563, LMBP 4555, LMBP 4556, LMBP 4557, LMBP 4558, LMBP 4559, LMBP 4560, respectively.

DENe2: Fragment of the envelope protein of DEN-2.

N-term: Nucleotide sequence that codifies for the first 45 amino acids of the MDH protein.

Figure 2:
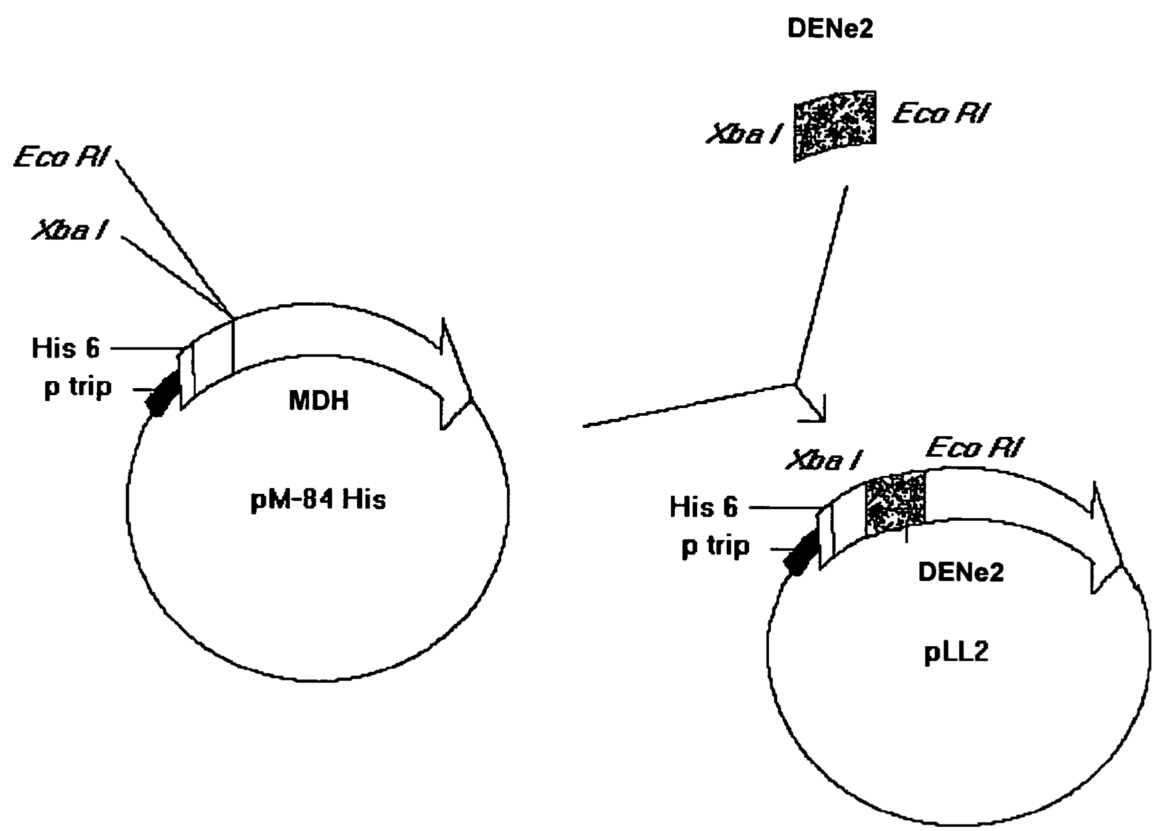

FIG. 2. Cloning strategy of the E2 fragment to obtain PLL2.

DENe2: Fragment of the envelope protein of DEN-2.

MDH: dehydrogenase mutant.

Figure 3:
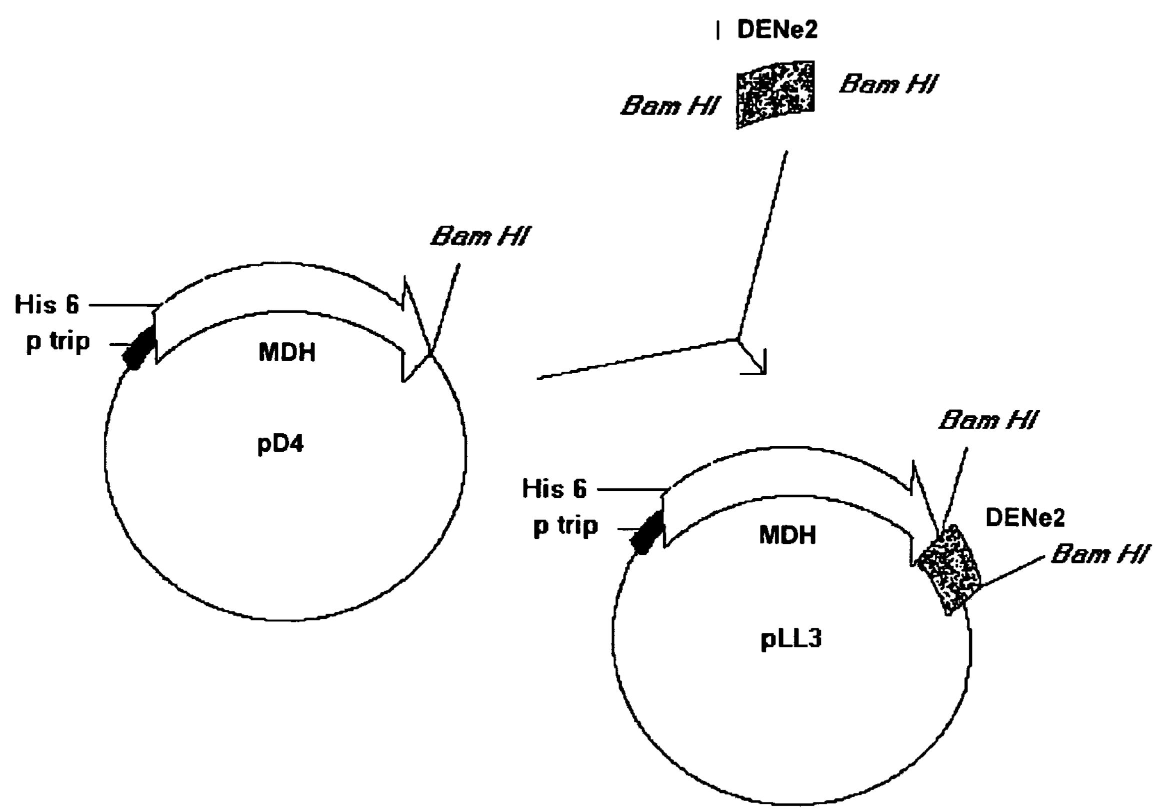

FIG. 3. Cloning strategy of the E2 fragment to obtain PLL3.

DENe2: Fragment of the envelope protein of DEN-2.

MDH: dehydrogenase mutant.

Figure 4:
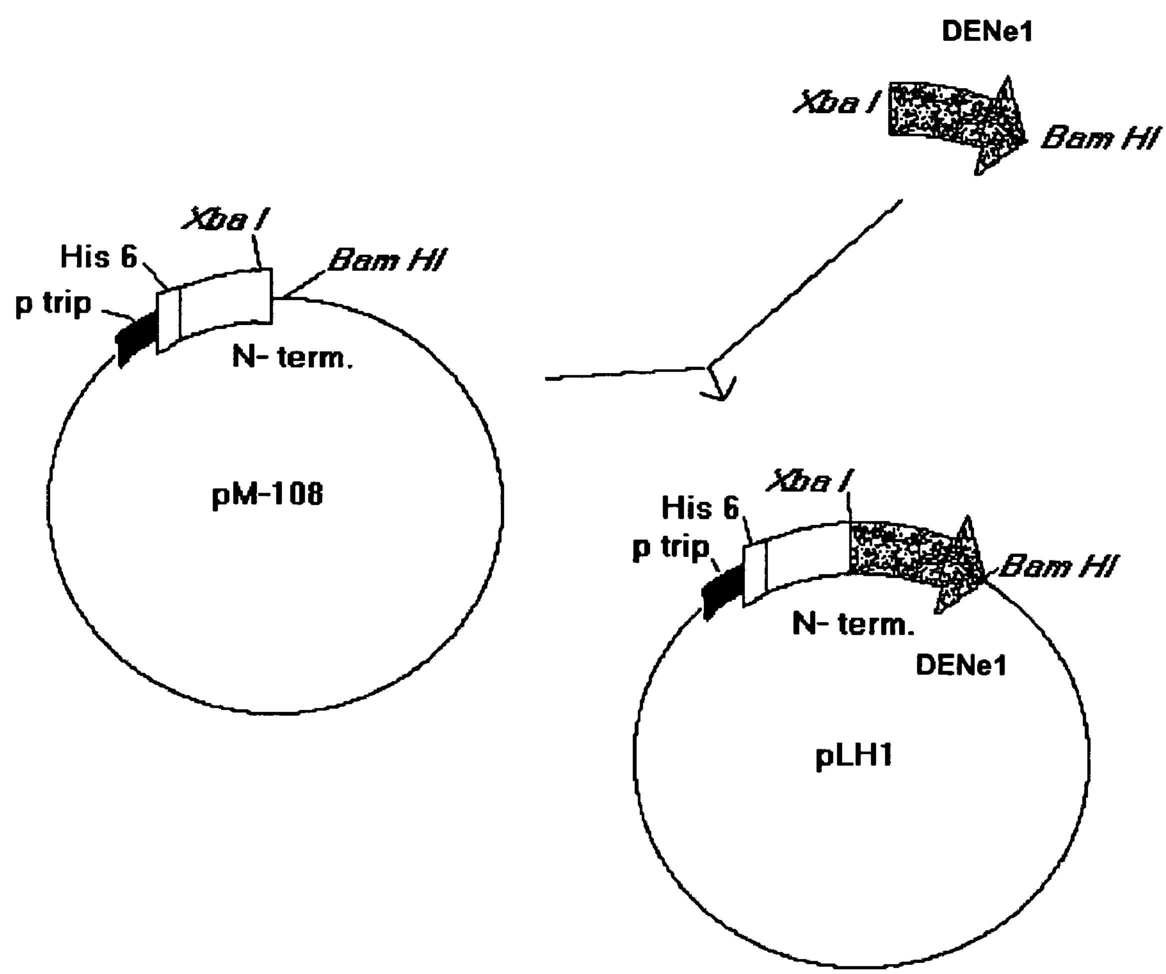

FIG. 4. Cloning strategy of the E1 fragment to obtain PLH1.

DENe1: Fragment of the envelope protein of DEN-1.

N-term: Nucleotide sequence that codifies for the first 45 amino acids of the MDH protein.

Figure 5:
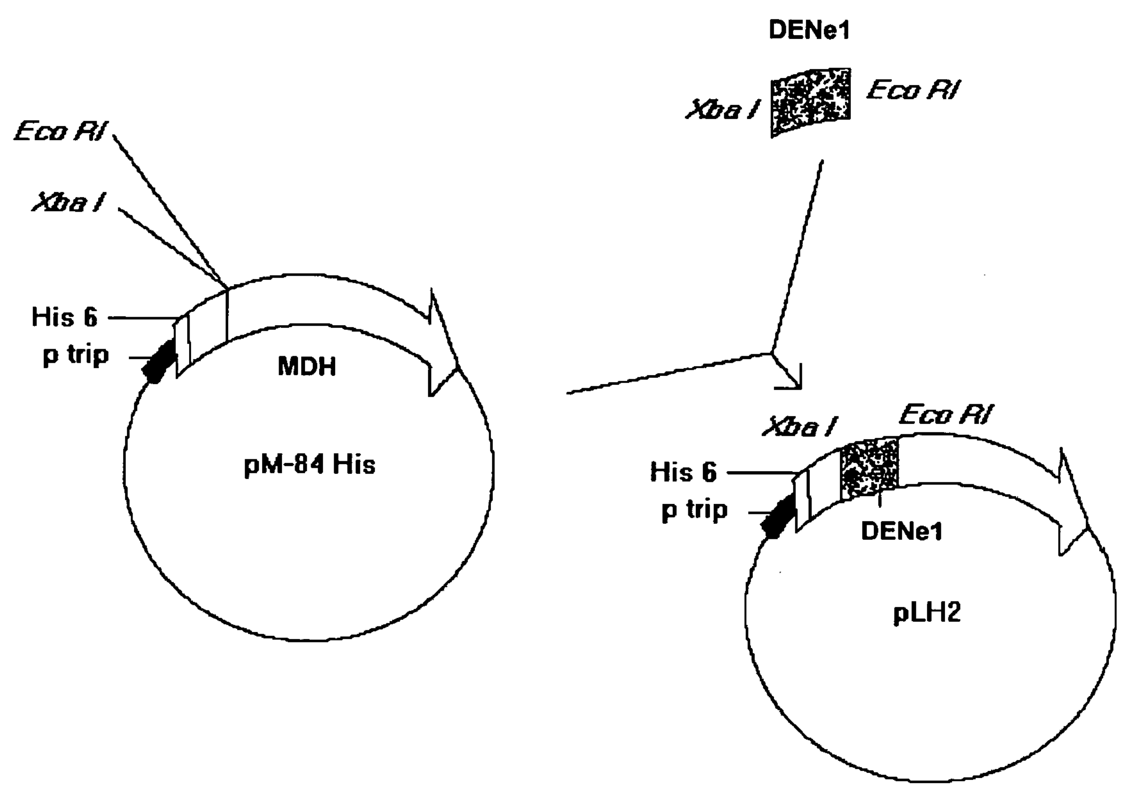

FIG. 5. Cloning strategy of the E1 fragment to obtain PLH2.

DENe1: Fragment of the envelope protein of DEN-1.

N-term: Nucleotide sequence that codifies for the first 45 amino acids of the MDH protein.

Figure 6:
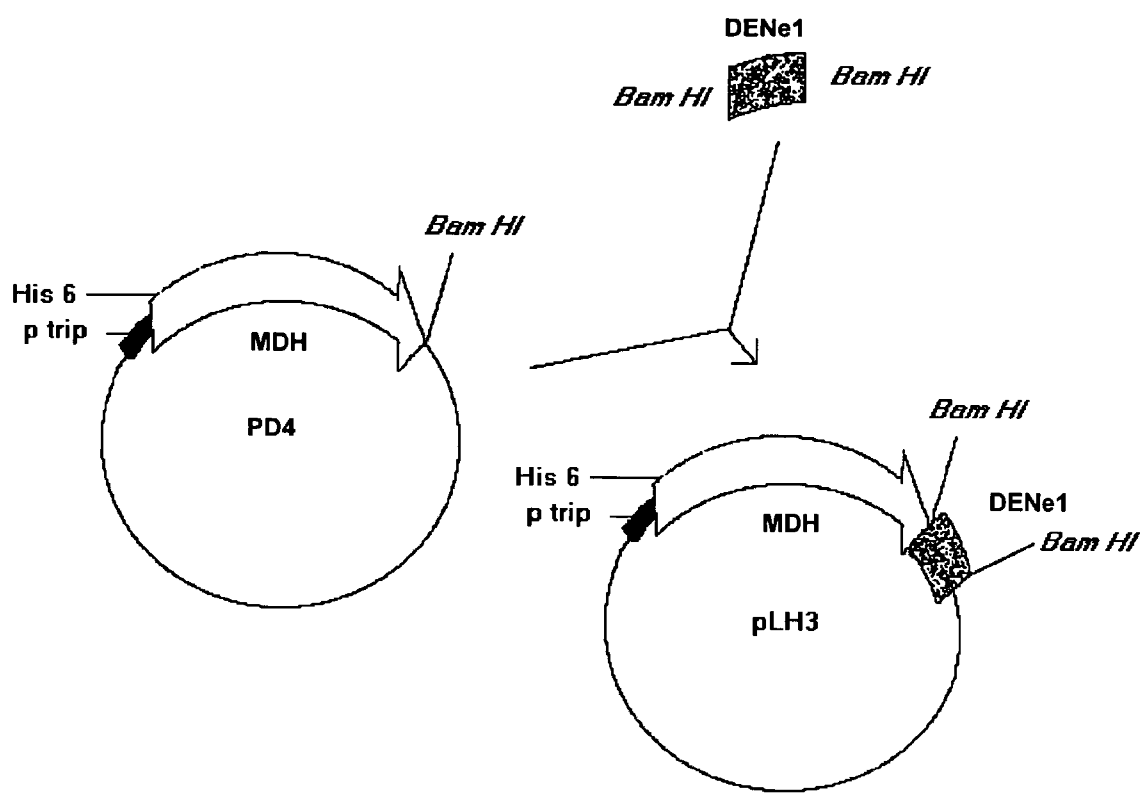

FIG. 6. Cloning strategy of the E1 fragment to obtain PLH3.

DENe1: Fragment of the envelope protein of DEN-1.

MDH: dehydrogenase mutant.

Figure 7:
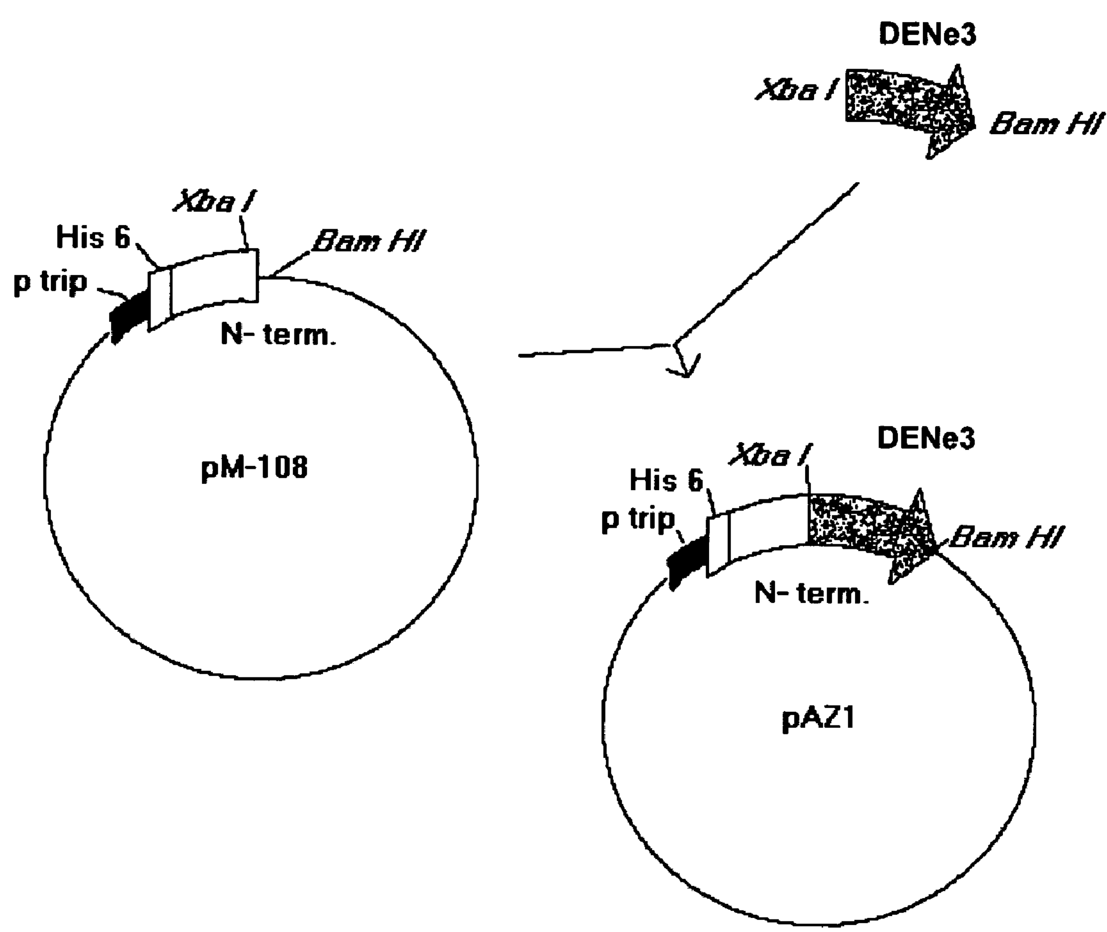

FIG. 7. Cloning strategy of the E3 fragment to obtain PAZ1.

DENe3: Fragment of the envelope protein of DEN-3.

N-term: Nucleotide sequence that codifies for the first 45 amino acids of the MDH protein.

Figure 8:
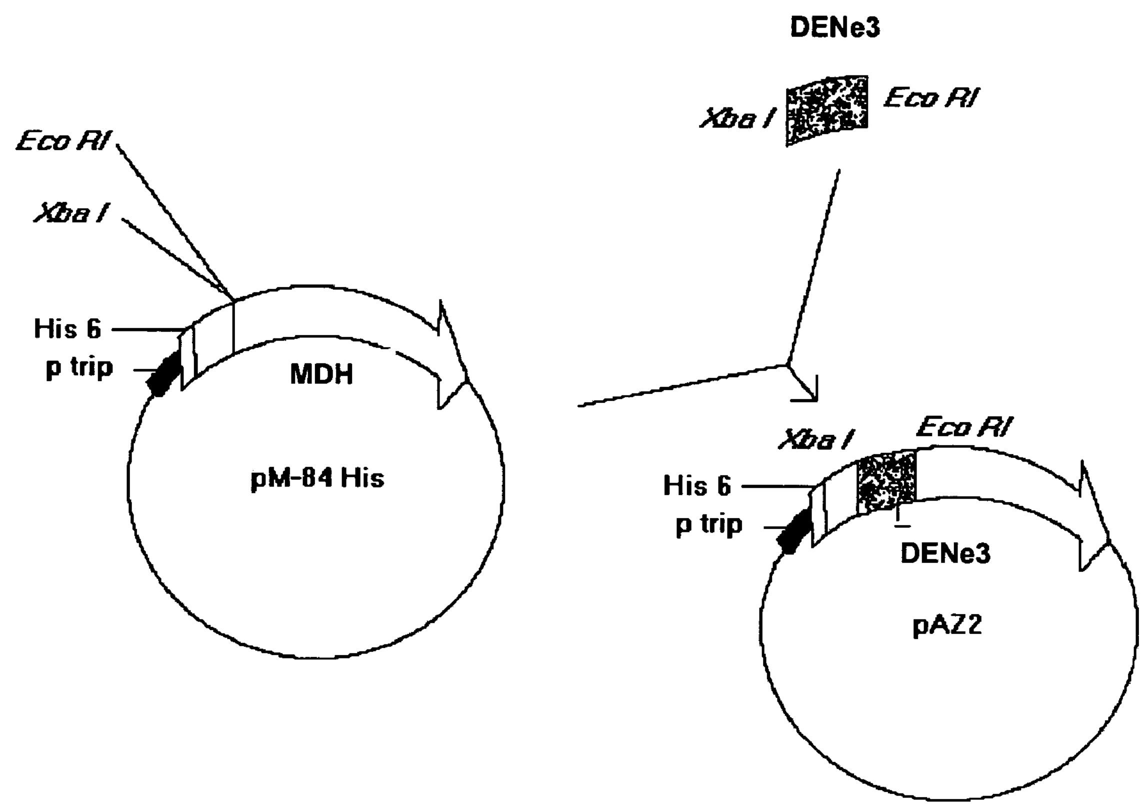

FIG. 8. Cloning strategy of the E3 fragment to obtain PAZ2.

DENe3: Fragment of the envelope protein of DEN-3.

MDH: dehydrogenase mutant.

Figure 9:
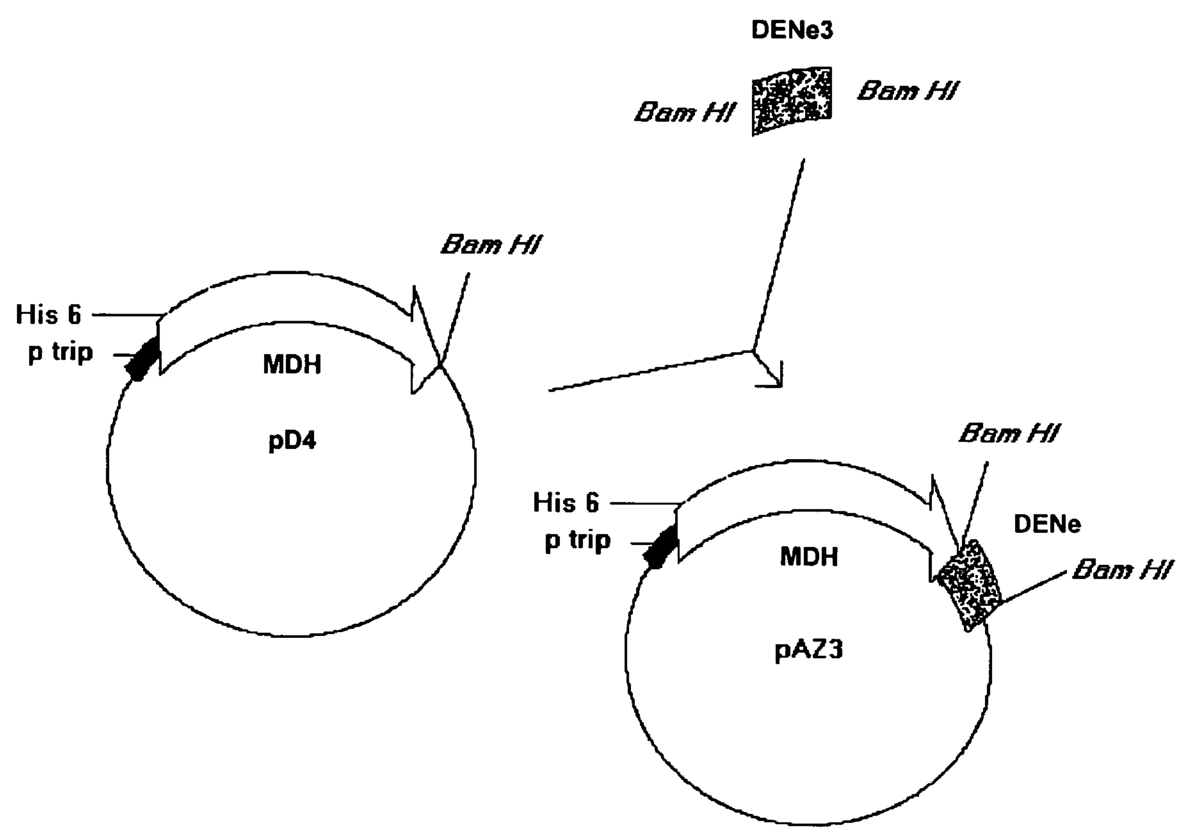

FIG. 9. Cloning strategy of the E3 fragment to obtain PAZ3.

DENe3: Fragment of the envelope protein of DEN-3.

MDH: dehydrogenase mutant.

Figure 10:
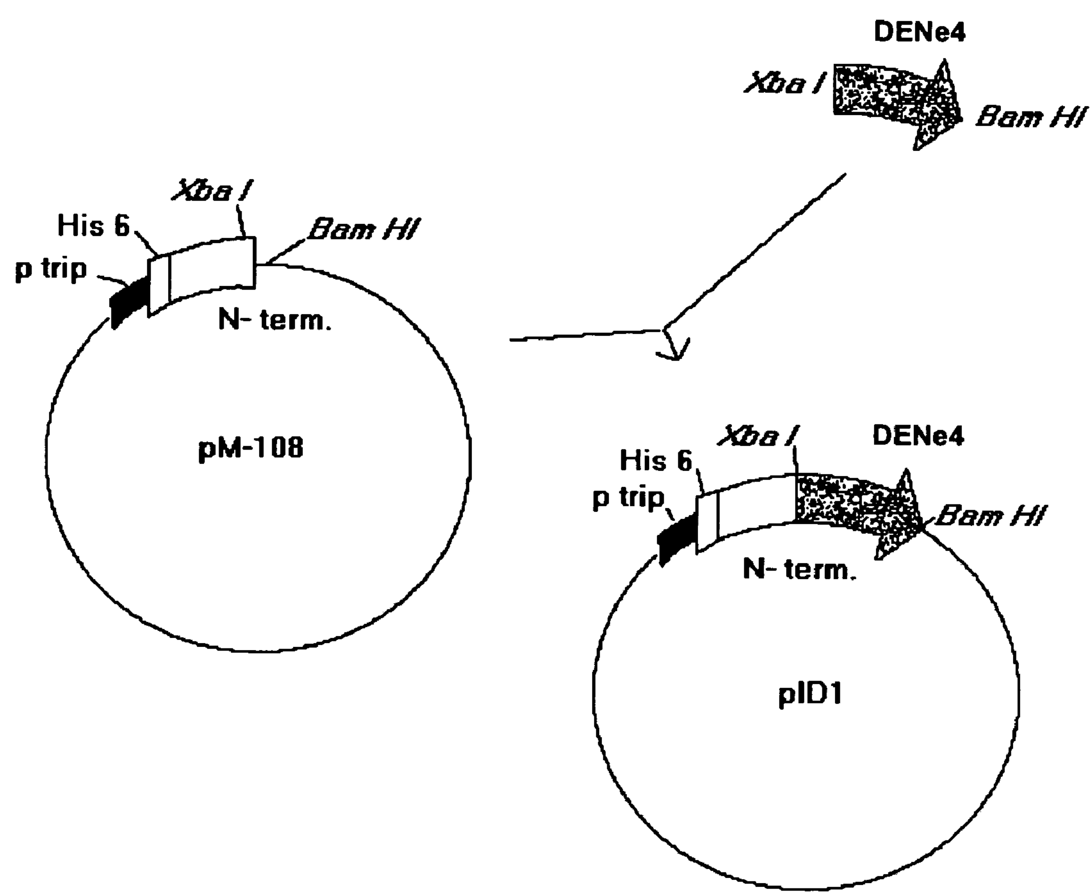

FIG. 10. Cloning strategy of the E4 fragment to obtain PID1.

DENe4: Fragment of the envelope protein of DEN-4.

N-term: Nucleotide sequence that codifies for the first 45 amino acids of the MDH protein.

Figure 11:
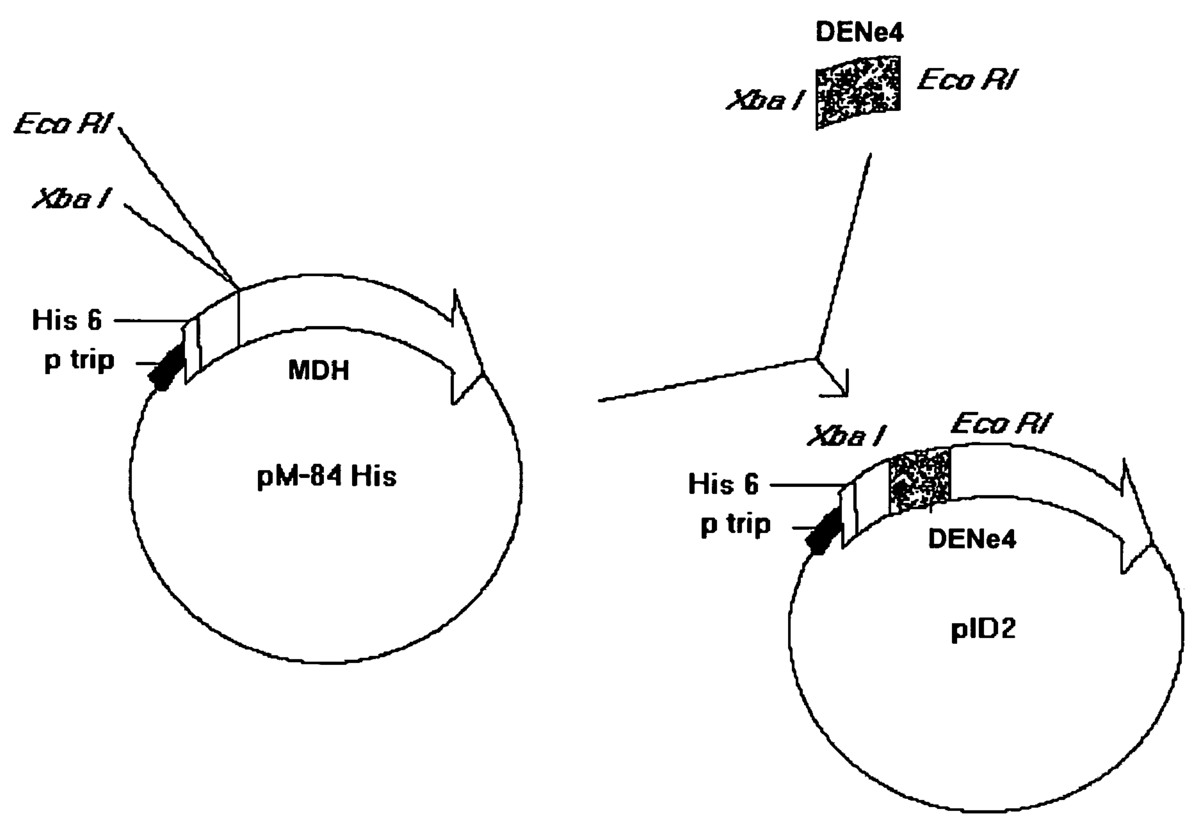

FIG. 11. Cloning strategy of the E4 fragment to obtain PID2.

DENe4: Fragment of the envelope protein of DEN4.

MDH: dehydrogenase mutant.

Figure 12:
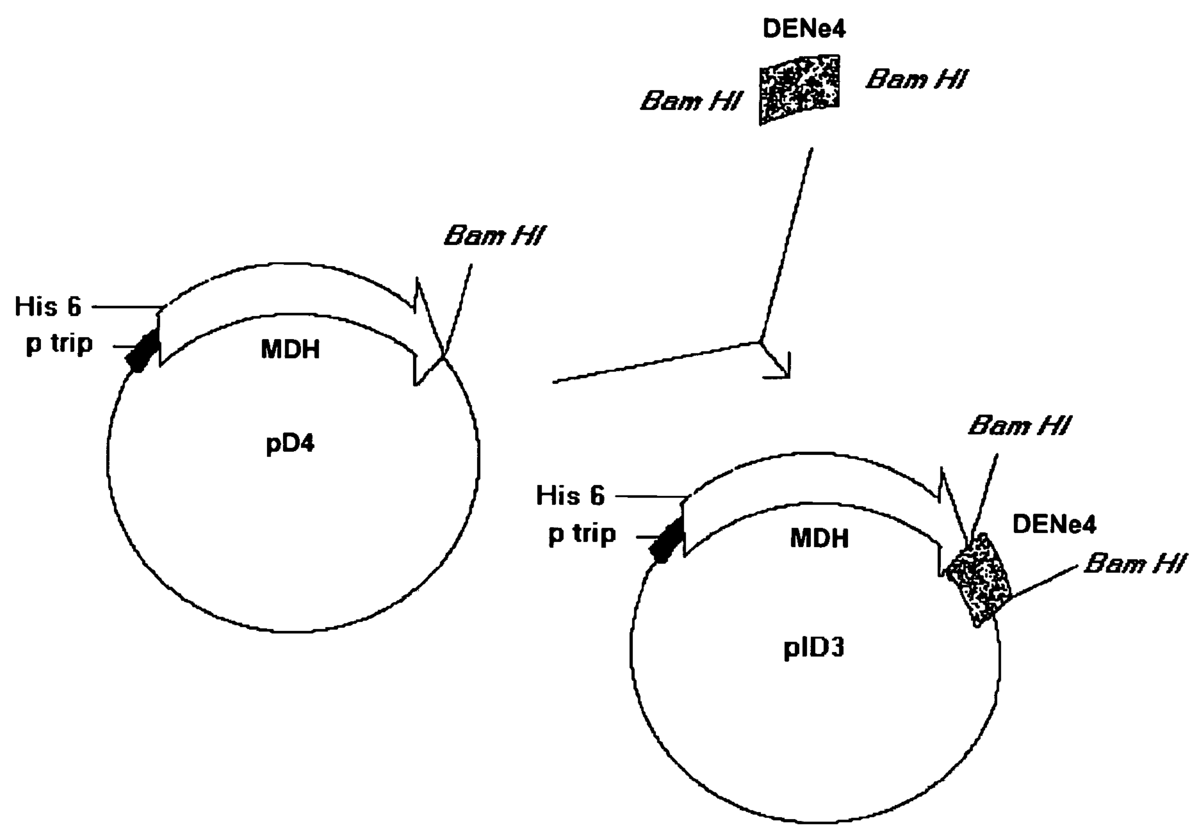

FIG. 12. Cloning strategy of the E4 fragment to obtain PID3.

DENe4: Fragment of the envelope protein of DEN4.

MDH: dehydrogenase mutant.

Figure 13:
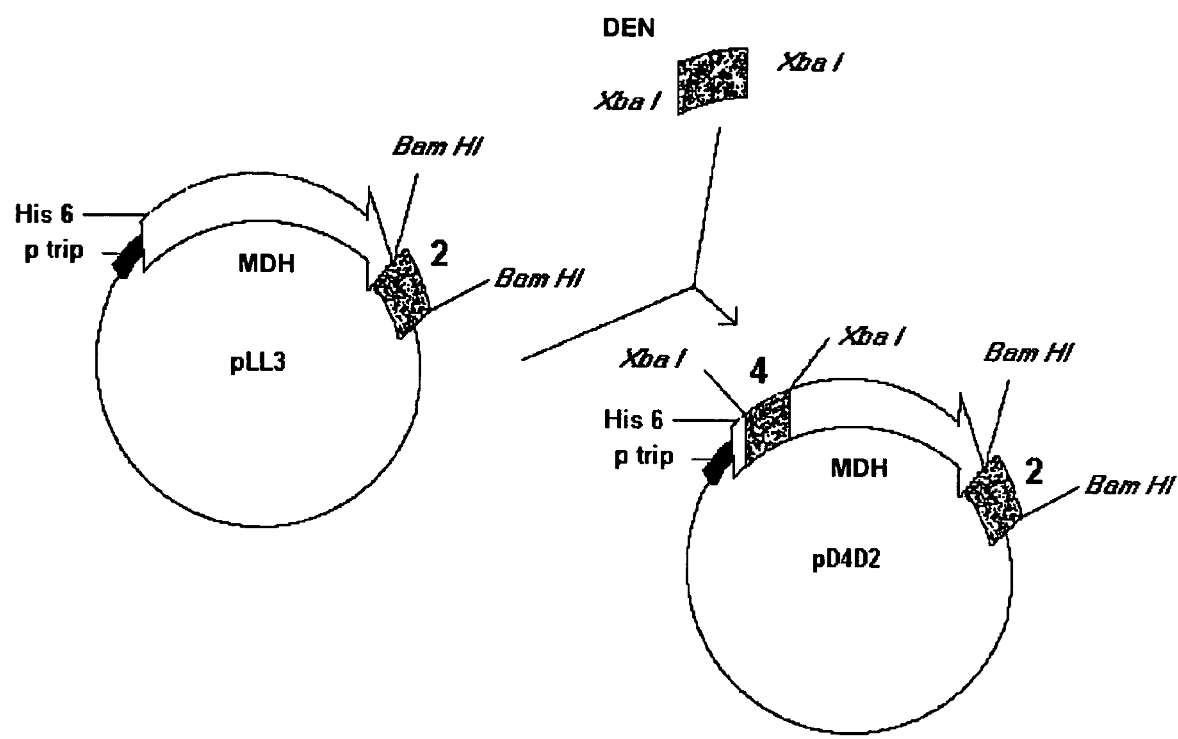

FIG. 13. Cloning strategy to obtain PD4D2.

DENe4: Fragment of the envelope protein of DEN4.

DENe2: Fragment of the envelope protein of DEN-2.

MDH: dehydrogenase mutant.

EXAMPLES

Example 1

Obtaining of PLL1

The nucleotide sequence that codifies for the amino acids from 286 to 426 of the envelope protein from the DEN-2 virus (Sec. Id. No. 22) was amplified with the oligonucleotides identified in the list of sequences as Sequence No.1 and Sequence No. 2 from the DEN-2 virus strain genotype Jamaica (Deubel V., Kinney R. M., Trent D. W. Nucleotide sequence and deduced amino acid sequence of the nonstructural proteins of Dengue type 2 virus, Jamaica genotype: Comparative analysis of the full-length genome. Virology 1988.165:234-244).

Figure 1:
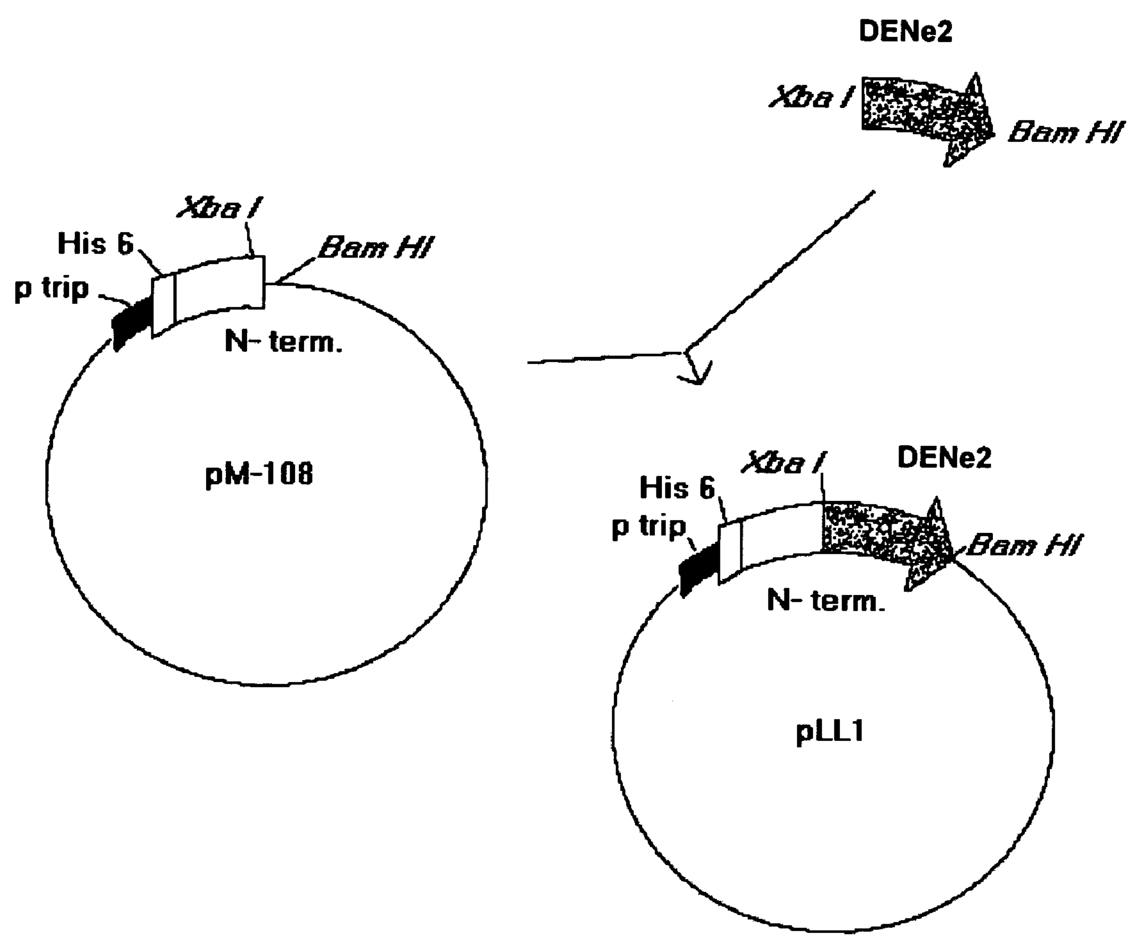
FIG. 1. Cloning strategy of the E2 fragment to obtain PLL1.

The vector was created by digestion of the pM108 His plasmid with Xba I/Bam HI, which contains the nucleotide sequence that codifies for the N-terminal region of the MDH and for a sequence of 6 histidines (Sequence No. 23). Upon ligation, the potential recombinants were analyzed by restriction enzyme digestion and positive clones were sequenced to check up the junctions. Competent cells W3110 (Hill C. W., Harnish B. W. 1982. Transposition of a chromosomal segment bounded by redundant rRNA genes in *Escherichia coli*. J Bacteriology. 149:449-457) were transformed with the selected clone, called pLL1 (FIG. 1 and Sequence No. 24). Upon growing the colony in Luria Bertani (LB) medium, a SDS-PAGE of the cellular lysate was done. As a result a 25 kDA band was obtained, which accounted for 10% of the total cellular proteins. The size of the protein obtained corresponded to the sum of the N-terminal region from the MDH protein and the DENe protein fragment from the DEN-2 virus. The protein was recognized in Immunoblotting by polyclonal antibodies (PA) anti-DEN-2 contained in the HMAF. This protein was denominated PLL1 (Sequence No. 25).

Example 2

Purification of the PLL1 Protein

The biomass obtained from the *E. coli* strain transformed with pLL1 and grown at 37° C. was disrupted by French press. The recombinant protein was obtained preponderantly as insoluble form associated to the pellet of the cellular disruption. From the pellet the protein was extracted with urea 6 M and the supernatant, containing the PLL1 protein, was loaded onto a G-25 column to eliminate the chaotropic agent. The fraction obtained was then loaded onto the Chelating-sepharose FF column (Pharmacia, UK), in the presence of $Cu^{++}$ ions. The protein was eluted with Imidazole 50 mM and the obtained volume was loaded onto a G-25 column to finally obtain the protein in the formulation buffer NaCl 100 mM, $KCl_2$ 2 mM, $Na_2HPO_4$ 10 mM, pH 7.2, $KH_2PO_4$ 1 mM (PBS). This preparation was used for immunological studies.

Example 3

Antigenic characterization of PLL1

The purified fraction of PLL1 was characterized either by its recognition by different polyclonal sera and/or murine monoclonal antibodies, as well as by positive human sera to Dengue (table 1).

TABLE 1

Reactivity of PLL1 protein to monoclonal and polyclonal antibodies.

| Abs** | Specificity*** | PLL1* |
|---|---|---|
| HMAF | DEN-1 | + |
| HMAF | DEN-2 | ++ |
| HMAF | DEN-3 | − |
| HMAF | DEN-4 | − |
| HMAF | EEE | − |
| HMAF | YFV | − |
| HMAF | SLV | − |
| Mab 3H5 | NT | + |

*A total of 10 μg of purified PLL1 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

The highest recognitions in Dot blotting were obtained with the HMAF anti-DEN-2. This result coincides with the fact that the cloned region belongs to serotype 2. The recognition by HMAF against the other serotypes was less than in the case of serotype 2, in decreasing order: DEN-1, DEN-3 and DEN4. The antibodies generated by other flavivirus like the Yellow Fever virus and the Saint Louis Encephalitis virus had not any recognition at all. On the other hand, the Mab 3H5 had reactivity indeed. This recognition by Western blotting relied on disulphide bond since when the sample was reduced the signal was lost. Finally, the reactivity against three human sera of high titers and three of low titers against DEN-2 was measured, achieving a substantial signal in both cases by Western blotting and Dot blotting.

Example 4

Characterization of the Antibody Response Generated by PLL1

A total of 25 Balb/c mice were i.p immunized with 35 ug of purified PLL1 in Freund adjuvant; 10 animals were bled after four doses and the antibodies anti-DEN were evaluated by ELISA. High antibody titers against DEN-2 were obtained while, no reactivity was obtained against the rest of the serotypes (table 2 and table 5). In addition, the hemagglutination inhibition assay (HIA) was done and only positive titers were found against DEN-2 (table 3 and table 5). Finally, the in vitro neutralization assay was done and neutralization titers of 1:320 against DEN-2 were obtained. However, no neutralization of the viral infection was found against the rest of the serotypes (table 4 and table 5). These results indicate the high serotype-specificity of the antibodies elicited by PLL1.

TABLE 2

Antibody titers against DEN-2 from the sera obtained upon immunization of mice with PLL1.

| Mouse | Titers anti-DEN-2 PLL1 | Titers anti-DEN-2 PBSControl (−) |
|---|---|---|
| 1 | 1/128000 | <1:100 |
| 2 | 1/64000 | <1:100 |
| 3 | 1/64000 | <1:100 |
| 4 | 1/128000 | <1:100 |
| 5 | 1/32000 | <1:100 |
| 6 | 1/32000 | <1:100 |
| 7 | 1/64000 | <1:100 |
| 8 | 1/32000 | <1:100 |
| 9 | 1/128000 | <1:100 |
| 10 | 1/512000 | <1:100 |

TABLE 3

Titers by HI of the sera from the animals immunized with PLL1.

| Mouse | Titers by HI* anti-DEN-2 PLL1 | Titers by HI anti-DEN-2 PBS C(−) |
|---|---|---|
| 1 | <1:5 | <1:5 |
| 2 | >1:640 | <1:5 |
| 3 | 1:320 | <1:5 |
| 4 | 1:320 | <1:5 |
| 5 | >1:640 | <1:5 |
| 6 | >1:640 | <1:5 |
| 7 | >1:640 | <1:5 |
| 8 | 1:320 | <1:5 |
| 9 | >1:640 | <1:5 |
| 10 | <1:5 | <1:5 |

*The HI titers were defined as the highest dilution capable of inhibiting the hemagglutination of goose's erythrocytes against 8 hemagglutination viral units.

TABLE 4

| Viral neutralization assay with the sera of animals immunized with PLL1. | | |
|---|---|---|
| Mouse | Neutralizing titers* anti-DEN-2 PLL1 | Neutralizing titers anti-DEN-2 PBS C(−) |
| 1 | 1:320 | <1:5 |
| 2 | 1:320 | <1:5 |
| 3 | 1:320 | <1:5 |
| 4 | 1:320 | <1:5 |
| 5 | 1:80 | <1:5 |
| 6 | 1:160 | <1:5 |
| 7 | 1:320 | <1:5 |
| 8 | 1:40 | <1:5 |
| 9 | 1:160 | <1:5 |
| 10 | 1:320 | <1:5 |

*The neutralizing titers were defined as the highest dilution of serum having 50% reduction of the number of viral plaques.

TABLE 5

| Cross-reactivity assay against all the viral serotypes by ELISA, HI and viral neutralization with the sera of animals immunized with PLL1. | | | | |
|---|---|---|---|---|
| Mixture of sera* | ELISA (anti-DEN-1) | ELISA (anti DEN-2) | ELISA (anti-DEN-3) | ELISA (anti-DEN-4) |
| 1 (PLL1) | <1/100 | >1:128000 | <1/100 | <1/100 |
| 2 (PLL1) | <1/100 | 1:128000 | <1/100 | <1/100 |
| Mixture of sera* | HI** anti-DEN-1 | HI anti-DEN-2 | HI anti-DEN-3 | HI anti-DEN-4 |
| PLL1 | <1/5 | >1/320 | <1/5 | <1/5 |
| Mixture of sera* | Neutralizing titers*** anti-DEN-1 | Neutralizing titers anti-DEN-2 | Neutralizing titers anti-DEN-3 | Neutralizing titers anti-DEN-4 |
| 1 (PLL1) | <1:5 | 1:320 | <1:5 | <1:5 |
| 2 (PLL1) | <1:5 | 1:160 | <1:5 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 5

Obtaining of PLL2

The nucleotide sequence that codifies for the amino acids from 286 to 426 of the envelope protein from the DEN-2 virus (Sec. Id. No. 22) was amplified with the oligonucleotides identified in the list of sequences as Sequence No. 1 and Sequence No. 3 from the DEN-2 virus strain genotype Jamaica (Deubel V., Kinney R. M., Trent D. W. Nucleotide sequence and deduced amino acid sequence of the nonstructural proteins of Dengue type 2 virus, Jamaica genotype: Comparative analysis of the full-length genome. Virology 1988.165:234–244).

The vector was created by digestion of the pM84 His plasmid with Xba I/Eco RI, which contains the nucleotide sequence that codifies for the MDH protein and for a sequence of 6 histidines (Sequence No. 26). This digestion permits the insertion of the amplified fragment by PCR within the coding region for a structural domain of the MDH protein.

Upon ligation, the potential recombinants were analyzed by restriction enzyme digestion and positive clones were sequenced to check up the junctions. Competent cells MM294 (Hanahan D. 1983. Studies on transformation of *Escherichia coli* with plasmids. J. Mol. Biol. 166:557–580) were transformed with the selected clone, called pLL2 (FIG. 2 and Sequence No. 27). Upon growing the colony in LB medium, a SDS-PAGE of the cellular lysate was done. As a result a 80 kDA band was obtained, which accounted for 10% of the total cellular proteins. The size of the protein obtained corresponded to the sum of the size of the MDH protein and the DENe protein fragment from the DEN-2 virus. The protein was recognized in Immunoblotting by a HMAF anti-DEN-2 and was denominated PLL2 (Sequence No. 28).

Example 6

Purification of the PLL2 Protein

The biomass obtained from the *E. coli* strain transformed with pLL2 and grown at 37° C. was disrupted by French press. The recombinant protein was obtained in both forms: soluble and insoluble. From the soluble fraction a metal ions-affinity chromatography was done using the Chelating-sepharose FF column previously coupled with $Cu^{++}$ ions. The column was washed using Imidazolee 15 mM and the protein was eluted with Imidazolee 100 mM. On the other hand, the protein associated to the insoluble fraction was extracted using Urea 8 M, and the supernatant, containing the PLL2 protein, was loaded onto a G-25 column to eliminate the chaotropic agent. The fraction obtained was then loaded onto the Chelating-sepharose FF column (Pharmacia, UK), in the presence of $Cu^{++}$ ions. The protein was eluted with Imidazolee 100 mM. Finally, the pure fraction of each form of the protein were loaded onto a G-25 column to obtain the protein in the formulation buffer NaCl 100 mM, $KCl_2$ 2 mM, $Na_2HPO_4$ 10 mM, pH 7.2, $KH_2PO_4$ 1 mM (PBS). This preparations were used for immunological studies.

Example 7

Antigenic characterization of PLL2

The purified fraction of PLL2 was characterized either by its recognition by different polyclonal sera and/or murine monoclonal antibodies, as well as by positive human sera to Dengue (table 6).

The highest recognitions in Dot blotting were obtained with the HMAF anti-DEN-2. The recognition by HMAF against the other serotypes was less than in the case of serotype 2, in decreasing order: DEN-1, DEN-3 and DEN4. The antibodies generated by other flavivirus like the Yellow Fever virus and the Saint Louis Encephalitis virus had not any recognition at all. Nevertheless, related to the Mab 3H5, a great reactivity was observed (even higher than those obtained with the PLL1) either by Dot blot and Western blot. Contrariously to the PLL1 results, the recognition with the Mab 3H5 was the same when the reducing agents are present in the sample, indicating a possible conformational difference between both proteins. Finally, the reactivity against three human sera of high titers and three of low titers against DEN-2 was measured, achieving a substantial signal in both cases by Western blotting and Dot blotting.

TABLE 6

Reactivity of PLL2 protein to monoclonal and polyclonal antibodies.

| Abs** | Specificity*** | PLL2 sol, ins* |
|---|---|---|
| HMAF | DEN-1 | ++ |
| HMAF | DEN-2 | +++ |
| HMAF | DEN-3 | – |
| HMAF | DEN-4 | – |
| HMAF | EEE | – |
| HMAF | YFV | – |
| HMAF | SLV | – |
| Mab 3H5 | NT | +++ |

*A total of 10 μg of purified PLL2 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 8

Characterization of the Antibody Response Generated by PLL2

A total of 25 Balb/c mice were i.p immunized with 35 ug of purified PLL2 in Freund adjuvant; 10 animals were bled after four doses and the antibodies anti-DEN were evaluated by ELISA. High antibody titers against DEN-2 were obtained while, no reactivity was obtained against the rest of the serotypes (table 7 and table 10). In addition, the hemagglutination inhibition assay (HI) was done and only positive titers were found against DEN-2 (table 8 and table 10). Finally, the in vitro neutralization assay was done and neutralization titers of 1: 1280 against DEN-2 were obtained. Similarly to the results obtained with PLL1, no neutralization of the viral infection was found against the rest of the serotypes (table 9 and table 10). On the other hand, the results obtained with both variants of PLL2 were similar, indicating that the solubility status of the protein do not influece in the capacity of generating functional antibodies.

TABLE 7

Antibody titers against DEN-2 from the sera obtained upon immunization of mice with PLL2 soluble and insoluble.

| | Titers anti-DEN-2 (PLL2) | | Titers anti-DEN-2 |
|---|---|---|---|
| Mouse | PLL2 s | PLL2 ins | PBS C(−) |
| 1 | >1:128000 | 1:64000 | <1:100 |
| 2 | 1:128000 | >1:128000 | <1:100 |
| 3 | >1:128000 | 1:128000 | <1:100 |
| 4 | >1:128000 | >1:128000 | <1:100 |
| 5 | 1:64000 | >1:128000 | <1:100 |
| 6 | >1:128000 | 1:128000 | <1:100 |
| 7 | 1:64000 | >1:128000 | <1:100 |
| 8 | >1:128000 | 1:64000 | <1:100 |
| 9 | >1:128000 | 1:64000 | <1:100 |
| 10 | 1:128000 | >1:128000 | <1:100 |

TABLE 8

Titers by HI of the sera from the animals immunized with PLL2 soluble and insoluble.

| | Titers by HI* anti-DEN-2 (PLL2) | | Titers by HI anti-DEN-2 |
|---|---|---|---|
| Mouse | PLL2 s | PLL2 ins | PBS C(−) |
| 1 | >1:640 | >1:640 | <1:5 |
| 2 | >1:640 | >1:640 | <1:5 |
| 3 | 1:320 | >1:640 | <1:5 |
| 4 | >1:640 | 1:320 | <1:5 |
| 5 | 1:320 | <1:5 | <1:5 |
| 6 | >1:640 | >1:640 | <1:5 |
| 7 | >1:640 | 1:320 | <1:5 |
| 8 | <1:5 | 1:320 | <1:5 |
| 9 | 1:320 | >1:640 | <1:5 |
| 10 | >1:640 | >1:640 | <1:5 |

*The HI titers were defined as the highest dilution capable of inhibiting the hemagglutination of goose's erythrocytes against 8 hemagglutination viral units.

TABLE 9

Viral neutralization assay with the sera of animals immunized with PLL2 soluble and insoluble.

| | Neutralizing titers* anti-DEN-2 (PLL2) | | Neutralizing titers anti-DEN-2 |
|---|---|---|---|
| Mouse | PLL2 s | PLL2 ins | PBS C(−) |
| 1 | >1:1280 | >1:1280 | >1:1280 |
| 2 | >1:1280 | >1:1280 | <1:5 |
| 3 | >1:1280 | 1:640 | <1:5 |
| 4 | 1:640 | >1:1280 | <1:5 |
| 5 | 1:640 | 1:640 | <1:5 |
| 6 | >1:1280 | >1:1280 | <1:5 |
| 7 | >1:1280 | >1:1280 | <1:5 |
| 8 | >1:1280 | >1:1280 | <1:5 |
| 9 | >1:1280 | >1:1280 | <1:5 |
| 10 | >1:1280 | >1:1280 | <1:5 |

*The neutralizing titers were defined as the highest dilution of serum having 50% reduction of the number of viral plaques.

TABLE 10

Cross-reactivity assay against all the viral serotypes by ELISA, HI and viral neutralization with the sera of animals immunized with PLL2 soluble and insoluble.

| Mixture of sera* | ELISA (anti-DEN-1) | ELISA (anti DEN-2) | ELISA (anti-DEN-3) | ELISA (anti-DEN-4) |
|---|---|---|---|---|
| 1 (PLL2 sol.) | <1/100 | >1:128000 | <1/100 | <1/100 |
| 2 (PLL2 sol.) | <1/100 | 1:64000 | <1/100 | <1/100 |
| 1 (PLL2 ins.) | <1/100 | 1:64000 | <1/100 | <1/100 |
| 2 (PLL2 ins.) | <1/100 | >1:128000 | <1/100 | <1/100 |
| **Mixture of sera*** | **HI** anti-DEN-1** | **HI anti-DEN-2** | **HI anti-DEN-3** | **HI anti-DEN-4** |
| PLL2 sol. | <1/5 | >1/320 | <1/5 | <1/5 |
| PLL2 ins. | <1/5 | >1/320 | <1/5 | <1/5 |

TABLE 10-continued

Cross-reactivity assay against all the viral serotypes by ELISA, HI and viral neutralization with the sera of animals immunized with PLL2 soluble and insoluble.

| Mixture of sera* | Neutralizing titers*** anti-DEN-1 | Neutralizing titers anti-DEN-2 | Neutralizing titers anti-DEN-3 | Neutralizing titers anti-DEN-4 |
|---|---|---|---|---|
| 1 (PLL2) | <1:5 | 1:320 | <1:5 | <1:5 |
| 2 (PLL2) | <1:5 | 1:160 | <1:5 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 9

Obtaining of pLL3

The nucleotide sequence that codifies for the amino acids from 286 to 426 of the envelope protein from the DEN-2 virus (Sec. Id. No. 22) was amplified with the oligonucleotides identified in the list of sequences as Sequence No.4 and Sequence No.5 from the DEN-2 virus strain genotype Jamaica (Deubel V., Kinney R. M., Trent D. W. Nucleotide sequence and deduced amino acid sequence of the nonstructural proteins of Dengue type 2 virus, Jamaica genotype: Comparative analysis of the full-length genome. Virology 1988.165:234–244).

The vector was created by digestion of the pD4 plasmid with Bam HI/Bam HI which contains the nucleotide sequence that codifies for the MDH protein and for a sequence of 6 histidines without stop codon (Sequence No. 29). This digestion permits to the fusion of the amplified fragment by PCR after the C-terminal region for the MDH protein. Upon ligation, the potential recombinants were analyzed by restriction enzyme digestion and positive clones were sequenced to check up the junctions. Competent cells W3110 were transformed with the selected clone, called pLL3 (FIG. 3 and Sequence No. 30). Upon growing the colony in LB medium, a SDS-PAGE of the cellular lysate was done. As a result a 80 kDA band was obtained, which accounted for 20% of the total cellular proteins. The size of the protein obtained corresponded to the sum of the size of the MDH protein and the DENe protein fragment from the DEN-2 virus. The protein was recognized in Immunoblotting by a HMAFI anti-DEN-2 and was denominated PLL3 (Sequence No. 31).

Example 10

Purification of the PLL3 Protein

The biomass obtained from the *E. coli* strain transformed with pLL2 and grown at 37° C. was disrupted by French press. The recombinant protein was obtained in both forms: soluble and insoluble. From the insoluble fraction, the protein was extracted using Urea 6 M, and the supernatant, containing the PLL3 protein, was loaded onto a G-25 column to eliminate the chaotropic agent. The fraction obtained was then loaded onto the Chelating-Sepharose FF column (Pharmacia, UK), in the presence of $Cu^{++}$ ions. The colum was washed with Imidazolee 30 mM and the protein was eluted with Imidazole 100 mM. Finally, the pure fraction of the protein was loaded onto a G-25 column to obtain the protein in the formulation buffer (PBS). This preparation was used for immunological studies.

Example 11

Antigenic Characterization of PLL3

The purified fraction of PLL3 was characterized either by its recognition by different polyclonal sera and/or murine monoclonal antibodies, as well as by positive human sera to Dengue (table 11).

The highest recognitions in Dot blotting were obtained with the HMAF anti-DEN-2. The recognition by HMAF against the other serotypes was lower than in the case of serotype 2, in decreasing order: DEN-1, DEN-3 and DEN-4. The antibodies generated by other flavivirus like the Yellow Fever virus and the Saint Louis Encephalitis virus had not any recognition at all. Nevertheless, related to the Mab 3H5, a great reactivity was observed (similar to those obtained with the PLL2) either by Dot blot and Western blot. Contrariously to the PLL1 results, the recognition with the Mab 3H5 was the same when the reducing agents are present in the sample, indicating a possible conformational difference between both proteins. Finally, the reactivity against three human sera of high titers and three of low titers against DEN-2 was measured, achieving a substantial signal in both cases by Western blotting and Dot blotting. These results were similar to those obtained with PLL2.

TABLE 11

Reactivity of PLL3 protein to monoclonal and polyclonal antibodies.

| Abs** | Specificity*** | PLL3* |
|---|---|---|
| HMAF | DEN-1 | ++ |
| HMAF | DEN-2 | +++ |
| HMAF | DEN-3 | − |
| HMAF | DEN-4 | − |
| HMAF | EEE | − |
| HMAF | YFV | − |
| HMAF | SLV | − |
| Mab 3H5 | NT | +++ |

*A total of 10 μg of purified PLL3 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 12

Characterization of the Antibody Response Generated by PLL3

A total of 25 Balb/c mice were i.p immunized with 35 ug of purified PLL3 in Freund adjuvant; 10 animals were bled after four doses and the antibodies anti-DEN were evaluated by ELISA. High antibody titers against DEN-2 were obtained while, no reactivity was obtained against the rest of the serotypes (table 12 and table 15). In addition, the hemagglutination inhibition (HI) assay was done and only positive titers were found against DEN-2 (table 13 and table 15). Finally, the in vitro neutralization assay was done and neutralization titers of 1: 1280 against DEN-2 were obtained (table 14). No neutralization of the viral infection was found against the rest of the serotypes (table 15). Using the three tests, high levels of serotype-specific antibodies were detected, similar of those obtained after the immunization with the PLL2 protein.

TABLE 12

Antibody titers against DEN-2 from the sera obtained upon immunization of mice with PLL3.

| Mouse | Titers anti-DEN-2 (PLL3) | Titers anti-DEN-2 PBS C(−) |
|---|---|---|
| 1 | 1:128000 | <1:100 |
| 2 | >1:128000 | <1:100 |
| 3 | >1:128000 | <1:100 |
| 4 | 1:64000 | <1:100 |
| 5 | >1:128000 | <1:100 |
| 6 | 1:64000 | <1:100 |
| 7 | >1:128000 | <1:100 |
| 8 | >1:128000 | <1:100 |
| 9 | 1:128000 | <1:100 |
| 10 | >1:128000 | <1:100 |

TABLE 13

Titers by HI of the sera from the animals immunized with PLL3.

| Mouse | Titers by HI* anti-DEN-2 (PLL3) | Titers by HI anti-DEN-2 PBS C(−) |
|---|---|---|
| 1 | >1:640 | <1:5 |
| 2 | 1:320 | <1:5 |
| 3 | 1:320 | <1:5 |
| 4 | >1:640 | <1:5 |
| 5 | 1:320 | <1:5 |
| 6 | >1:640 | <1:5 |
| 7 | >1:640 | <1:5 |
| 8 | >1:640 | <1:5 |
| 9 | 1:320 | <1:5 |
| 10 | >1:640 | <1:5 |

*The HI titers were defined as the highest dilution capable of inhibiting the hemagglutination of goose's erythrocytes against 8 hemagglutination viral units.

TABLE 14

Viral neutralization assay with the sera of animals immunized with PLL3.

| Mouse | Neutralizing titers anti-DEN-2 PLL3 | Neutralizing titers anti-DEN-2 PBS C(−) |
|---|---|---|
| 1 | >1:1280 | <1:5 |
| 2 | >1:1280 | <1:5 |
| 3 | >1:1280 | <1:5 |
| 4 | 1:640 | <1:5 |
| 5 | >1:1280 | <1:5 |
| 6 | >1:1280 | <1:5 |
| 7 | >1:1280 | <1:5 |
| 8 | >1:1280 | <1:5 |
| 9 | 1:640 | <1:5 |
| 10 | >1:1280 | <1:5 |

*The neutralizing titers were defined as the highest dilution of serum having 50% reduction of the number of viral plaques.

TABLE 15

Cross-reactivity assay against all the viral serotypes by ELISA, HI and viral neutralization with the sera of animals immunized with PLL3.

| Mixture of sera* | ELISA (anti-DEN-1) | ELISA (anti DEN-2) | ELISA (anti-DEN-3) | ELISA (anti-DEN-4) |
|---|---|---|---|---|
| 1(PLL3) | <1/100 | >1:128000 | <1/100 | <1/100 |
| 2(PLL3) | <1/100 | >1:128000 | <1/100 | <1/100 |
| **Mixture of sera*** | **HI** anti-DEN-1** | **HI anti-DEN-2** | **HI anti-DEN-3** | **HI anti-DEN-4** |
| PLL3 | <1/5 | >1/320 | <1/5 | <1/5 |
| **Mixture of sera*** | **Neutralizing titers*** anti-DEN-1** | **Neutralizing titers*** anti-DEN-2** | **Neutralizing titers*** anti-DEN-3** | **Neutralizing titers*** anti-DEN-4** |
| 1(PLL3) | <1:5 | >1:1280 | <1:5 | <1:5 |
| 2(PLL3) | <1:5 | >1:1280 | <1:5 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 13

Obtaining of pLH1

The nucleotide sequence that codifies for the amino acids from 286 to 426 of the envelope protein from the DEN-1 virus (Sec. Id. No. 32) was amplified with the oligonucleotides identified in the list of sequences as Sequence No.6 and Sequence No.7 from the DEN-1 virus strain genotype (Chu M. C., O'Rourke E. J., Trent D. W. Genetic relatedness among structural protein genes of dengue 1 virus strains. J. Gen. Virol. 1989. 70:1701–1712).

The vector was created by digestion of the pM108 His plasmid with Xba I/Bam HI, which contains the nucleotide sequence that codifies for the N-terminal region of the MDH and for a sequence of 6 histidines (Sequence No. 23). Upon ligation, the potential recombinants were analyzed by restriction enzyme digestion and positive clones were sequenced to check up the junctions. Competent cells W3110 were transformed with the selected clone, called pLH1 (FIG. 4 and Sequence No.33). Upon growing the colony in Luria Bertani (LB) medium, a SDS-PAGE of the cellular lysate was done. As a result a 25 kDA band was obtained, which accounted for 10% of the total cellular proteins. The size of the protein obtained corresponded to the sum of the N-terminal region from the MDH protein and the DENe protein fragment from the DEN-1 virus. The protein was recognized in Immunoblotting by polyclonal antibodies (PA) anti-DEN-1 contained in the HMAF. This protein was denominated PLH1 (Sequence No.34).

Example 14

Purification of the Protein PLH1

The biomass obtained from the *E. coli* strain transformed with pLH1 and grown at 37° C. was disrupted by French press. The recombinant protein was obtained preponderantly as insoluble form associated to the pellet of the cellular disruption. From the pellet, the protein was extracted with urea 7 M and the supernatant, containing the PLH1 protein, was loaded onto a G-25 column to eliminate the chaotropic agent. The fraction obtained was then loaded onto the Chelating-sepharose FF column (Pharmacia, UK), in the presence of $Cu^{++}$ ions. The protein was eluted with Imidazolee 60 mM and the obtained volume was loaded onto a G-25 column to finally obtain the protein in the formulation buffer (PBS). This preparation was used for immunological studies.

Example 15

Antigenic Characterization of PLH1

The purified fraction of PLH1 was characterized either by its recognition by different polyclonal sera and/or murine monoclonal antibodies, as well as by positive human sera to Dengue (table 16).

The highest recognitions in Dot blotting were obtained with the HMAF anti-DEN-1. The recognition by HMAF against the other serotypes was lower than in the case of serotype 1. The antibodies generated by other flavivirus like the Yellow Fever virus and the Saint Louis Encephalitis virus had not any recognition at all. Finally, the reactivity against three human sera of high titers and three of low titers against DEN-1 was measured, achieving a substantial signal in both cases by Western blotting and Dot blotting.

TABLE 16

Reactivity of PLH1 protein to monoclonal and polyclonal antibodies

| Abs** | Specificity*** | PLH1 |
|---|---|---|
| HMAF | DEN-1 | ++ |
| HMAF | DEN-2 | + |
| HMAF | DEN-3 | − |
| HMAF | DEN-4 | − |
| HMAF | EEE | − |
| HMAF | YFV | − |
| HMAF | SLV | − |
| Mab 3H5 | NT | − |

*A total of 10 μg of purified PLH1 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 16

Characterization of the Antibody Response Generated by PLH1

A total of 25 Balb/c mice were i.p immunized with 35 ug of purified PLH1 in Freund adjuvant; 10 animals were bled after four doses and the antibodies anti-DEN were evaluated by ELISA. High antibody titers against DEN-1 were obtained while, no reactivity was obtained against the rest of the serotypes (table 17 and table 20). In addition, the HI assay was done and only positive titers were found against DEN-1 (table 18 and table 20). Finally, the in vitro neutralization assay was done and neutralization titers of 1:320 against DEN-1 were obtained. However, no neutralization of the viral infection was found against the rest of the serotypes (table 19 and table 20). These results indicate the high serotype-specificity of the antibodies elicited by PLH1.

TABLE 17

Antibody titers against DEN-1 from the sera obtained upon immunization of mice with PLH1.

| Mouse | Titers anti-DEN-1 (PLH1) | Titers anti-DEN-1 PBS C(−) |
|---|---|---|
| 1 | 1/64000 | <1:100 |
| 2 | 1/128000 | <1:100 |
| 3 | 1/64000 | <1:100 |
| 4 | 1/32000 | <1:100 |
| 5 | 1/32000 | <1:100 |
| 6 | 1/64000 | <1:100 |
| 7 | 1/128000 | <1:100 |
| 8 | 1/64000 | <1:100 |
| 9 | 1/128000 | <1:100 |
| 10 | 1/128000 | <1:100 |

TABLE 18

Titers by HI of the sera from the animals immunized with PLH1.

| Mouse | Titers by HI* anti-DEN-1 (PLH1) | Titers by HI* anti-DEN-1 PBS C(−) |
|---|---|---|
| 1 | >1:640 | <1:5 |
| 2 | 1:320 | <1:5 |
| 3 | >1:640 | <1:5 |
| 4 | >1:640 | <1:5 |
| 5 | >1:640 | <1:5 |
| 6 | 1:320 | <1:5 |
| 7 | 1:40 | <1:5 |
| 8 | 1:320 | <1:5 |
| 9 | >1:640 | <1:5 |
| 10 | <1:5 | <1:5 |

*The HI titers were defined as the highest dilution capable of inhibiting the hemagglutination of goose's erythrocytes against 8 hemagglutination viral units.

TABLE 19

Viral neutralization assay with the sera of animals immunized with PLH1.

| Mouse | Neutralizing titers* anti-DEN-1 (PLH1) | Neutralizing titers* anti-DEN-1 PBS C(−) |
|---|---|---|
| 1 | 1:80 | <1:5 |
| 2 | 1:320 | <1:5 |
| 3 | 1:40 | <1:5 |
| 4 | 1:320 | <1:5 |
| 5 | 1:80 | <1:5 |
| 6 | 1:160 | <1:5 |
| 7 | 1:320 | <1:5 |
| 8 | 1:320 | <1:5 |
| 9 | 1:320 | <1:5 |
| 10 | 1:320 | <1:5 |

*The neutralizing titers were defined as the highest dilution of serum having 50% reduction of the number of viral plaques.

TABLE 20

Cross-reactivity assay against all the viral serotypes by ELISA, HI and viral neutralization with the sera of animals immunized with PLH1.

| Mixture of sera* | ELISA (anti-DEN-1) | ELISA (anti DEN-2) | ELISA (anti-DEN-3) | ELISA (anti-DEN-4) |
|---|---|---|---|---|
| 1 (PLH1) | 1:128000 | <1/100 | <1/100 | <1/100 |
| 2 (PLH1) | >1:128000 | <1/100 | <1/100 | <1/100 |
| **Mixture of sera*** | **HI** anti-DEN-1** | **HI anti-DEN-2** | **HI anti-DEN-3** | **HI anti-DEN-4** |
| PLH1 | >1:320 | <1/5 | <1/5 | <1/5 |
| **Mixture of sera*** | **Neutralizing titers*** anti-DEN-1** | **Neutralizing titers*** anti-DEN-2** | **Neutralizing titers*** anti-DEN-3** | **Neutralizing titers*** anti-DEN-4** |
| 1(PLH1) | 1:160 | <1:5 | <1:5 | <1:5 |
| 2(PLH1) | 1:320 | <1:5 | <1:5 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 17

Obtaining of pLH2

The nucleotide sequence that codifies for the amino acids from 286 to 426 of the envelope protein from the DEN-1 virus (Sequence No. 32) was amplified with the oligonucleotides identified in the list of sequences as Sequence No.6 and Sequence No.8 from a DEN-1 viral strain (Chu M. C., O'Rourke E. J., Trent D. W. Genetic relatedness among structural protein genes of dengue 1 virus strains. J. Gen. Virol. 1989. 70:1701-1712).

The vector was created by digestion of the pM84 His plasmid with Xba I/Eco RI, which contains the nucleotide sequence that codifies for the MDH protein and for a sequence of 6 histidines (Sequence No. 26). This digestion permits the insertion of the amplified fragment by PCR within the coding region for a structural domain of the MDH protein. Upon ligation, the potential recombinants were analyzed by restriction enzyme digestion and positive clones were sequenced to check up the junctions. Competent cells MM294 were transformed with the selected clone, called pLH2 (FIG. 5 and Sequence No.35). Upon growing the colony in LB medium, a SDS-PAGE of the cellular lysate was done. As a result a 80 kDA band was obtained, which accounted for 20% of the total cellular proteins. The size of the protein obtained corresponded to the sum of the size of the MDH protein and the DENe protein fragment from the DEN-1 virus. The protein was recognized in Immunoblotting by a HMAF anti-DEN-1 and was denominated PLH2 (Sequence No.36).

Example 18

Purification of the PLH2 Protein

The biomass obtained from the *E. coli* strain transformed with pLH2 and grown at 37° C. was disrupted by French press. The recombinant protein was obtained in both forms: soluble and insoluble. The protein associated to the insoluble fraction was extracted using Urea 7 M, and the supernatant, containing the PLH2 protein, was loaded onto a G-25 column to eliminate the chaotropic agent. The fraction obtained was then loaded onto the Chelating-sepharose FF column (Pharmacia, UK), in the presence of $Cu^{++}$ ions. The column was washed with Imidazolee 40 mM and the protein was eluted with Imidazole 100 mM. Finally, the pure fraction was loaded onto a G-25 column to obtain the protein in the formulation (PBS). This preparation was used for immunological studies.

Example 19

Antigenic Characterization of PLH2

The purified fraction of PLH2 was characterized either by its recognition by different polyclonal sera and/or murine monoclonal antibodies, as well as by positive human sera to Dengue (table 21).

The highest recognitions in Dot blotting were obtained with the HMAF anti-DEN-1 (higher than those obtained with PLH1). The recognition by HMAF against the other serotypes was lower than in the case of serotype 1. The antibodies generated by other flavivirus like the Yellow Fever virus and the Saint Louis Encephalitis virus had not any recognition at all. Finally, the reactivity against five human sera of high titers and three of low titers against DEN-1 was measured, achieving a substantial signal in both cases by Western blotting and Dot blotting.

TABLE 21

Reactivity of PLH2 protein to monoclonal and polyclonal antibodies.

| Abs** | Specificity*** | PLH2 |
|---|---|---|
| HMAF | DEN-1 | +++ |
| HMAF | DEN-2 | + |
| HMAF | DEN-3 | − |
| HMAF | DEN-4 | − |
| HMAF | EEE | − |
| HMAF | YFV | − |
| HMAF | SLV | − |
| Mab 3H5 | NT | − |

*A total of 10 μg of purified PLH2 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 20

Characterization of the Antibody Response Generated by PLH2

A total of 25 Balb/c mice were i.p immunized with 20 ug of purified PLH2 in Freund adjuvant; 10 animals were bled after four doses and the antibodies anti-DEN were evaluated by ELISA. High antibody titers against DEN-1 were obtained while, no reactivity was obtained against the rest of the serotypes (table 22 and table 25). In addition, the HI assay was done and only positive titers were found against DEN-1 (table 23 and table 25). Finally, the in vitro neutralization assay was done and neutralization titers of 1: 1280 against DEN-1 were obtained (table 24). No neutralization of the viral infection was found against the rest of the serotypes. (table 25).

TABLE 22

Antibody titers against DEN-1 from the sera obtained upon immunization of mice with PLH2.

| Mouse | Titers anti-DEN-1 (PLH2) | Titers anti-DEN-1 PBS C(−) |
|---|---|---|
| 1 | 1:128000 | <1:100 |
| 2 | >1:128000 | <1:100 |
| 3 | 1:64000 | <1:100 |
| 4 | >1:128000 | <1:100 |
| 5 | 1:128000 | <1:100 |
| 6 | 1:64000 | <1:100 |
| 7 | >1:128000 | <1:100 |
| 8 | 1:128000 | <1:100 |
| 9 | >1:128000 | <1:100 |
| 10 | >1:128000 | <1:100 |

TABLE 23

Titers by HI of the sera from the animals immunized with PLH2.

| Mouse | Titers by HI* anti-DEN-1 (PLH2) | Titers by HI anti-DEN-1 PBS C(−) |
|---|---|---|
| 1 | <1:5 | <1:5 |
| 2 | >1:640 | <1:5 |
| 3 | 1:320 | <1:5 |
| 4 | 1:320 | <1:5 |
| 5 | >1:640 | <1:5 |
| 6 | >1:640 | <1:5 |
| 7 | >1:640 | <1:5 |
| 8 | 1:320 | <1:5 |
| 9 | >1:640 | <1:5 |
| 10 | <1:5 | <1:5 |

*The HI titers were defined as the highest dilution capable of inhibiting the hemagglutination of goose's erythrocytes against 8 hemagglutination viral units.

TABLE 24

Viral neutralization assay with the sera of animals immunized with PLH2.

| Mouse | Neutralizing titers* anti-DEN-1 (PLH2) | Neutralizing titers* anti-DEN-1. C(−) |
|---|---|---|
| 1 | >1:1280 | <1:5 |
| 2 | >1:1280 | <1:5 |
| 3 | >1:1280 | <1:5 |
| 4 | >1:1280 | <1:5 |
| 5 | >1:1280 | <1:5 |
| 6 | >1:1280 | <1:5 |
| 7 | >1:1280 | <1:5 |
| 8 | >1:1280 | <1:5 |
| 9 | 1:640 | <1:5 |
| 10 | >1:1280 | <1:5 |

*The neutralizing titers were defined as the highest dilution of serum having 50% reduction of the number of viral plaques.

TABLE 25

Cross-reactivity assay against all the viral serotypes by ELISA, HI and viral neutralization with the sera of animals immunized with PLH2.

| Mixture of sera* | ELISA (anti-DEN-1) | ELISA (anti DEN-2) | ELISA (anti-DEN-3) | ELISA (anti-DEN-4) |
|---|---|---|---|---|
| 1 (PLH2) | 1:64000 | <1/100 | <1/100 | <1/100 |
| 2 (PLH2) | >1:128000 | <1/100 | <1/100 | <1/100 |
| **Mixture of sera*** | **HI** anti-DEN-1** | **HI anti-DEN-2** | **HI anti-DEN-3** | **HI anti-DEN-4** |
| PLH2 | >1/320 | <1/5 | <1/5 | <1/5 |
| **Mixture of sera*** | **Neutralizing titers*** anti-DEN-1** | **Neutralizing titers anti-DEN-2** | **Neutralizing titers anti-DEN-3** | **Neutralizing titers anti-DEN-4** |
| 1(PLH2) | >1:1280 | <1:5 | <1:5 | <1:5 |
| 2(PLH2) | >1:1280 | <1:5 | <1:5 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 21

Obtaining of pLH3

The nucleotide sequence that codifies for the amino acids from 286 to 426 of the envelope protein from the DEN-1 virus (Sec. Id. No. 32) was amplified with the oligonucleotides identified in the list of sequences as Sequence No.9 and Sequence No.10 from the DEN-1 virus strain (Chu M. C., O'Rourke E. J., Trent D. W. Genetic relatedness among structural protein genes of dengue 1 virus strain. J. Gen. Virol.1989. 70:1701-1712).

The vector was created by digestion of the pD4 plasmid with Bam HI/Bam HI which contains the nucleotide sequence that codifies for the MDH protein and for a sequence of 6 histidines without stop codon (Sequence No.29). This digestion permits the fusion of the amplified fragment by PCR after the C-terminal region for the MDH protein. Upon ligation, the potential recombinants were analyzed by restriction enzyme digestion and positive clones were sequenced to check up the junctions. Competent cells W3110 were transformed with the selected clone, called pLH3 (FIG. 6 and Sequence No.37). Upon growing the colony in LB medium, a SDS-PAGE of the cellular lysate was done. As a result a 80 kDA band was obtained, which accounted for 20% of the total cellular proteins. The size of the protein obtained corresponded to the sum of the size of the MDH protein and the DENe protein fragment from the DEN-1 virus. The protein was recognized in Immunoblotting by a HMAF anti-DEN-1 and was denominated PLH3 (Sequence No.38).

Example 22

Purification of the PLH3 Protein

The biomass obtained from the *E. coli* strain transformed with pLH3 and grown at 37° C. was disrupted by French press. The recombinant protein was obtained in both forms: soluble and insoluble. From the insoluble fraction, the protein was extracted using Urea 6 M, and the supernatant, containing the PLH3 protein, was loaded onto a G-25 column to eliminate the chaotropic agent. The fraction obtained was then loaded onto the Chelating-Sepharose FF column (Pharmacia, UK), in the presence of $Cu^{++}$ ions. The colum was washed with Imidazolee 30 mM and the protein was eluted with Imidazole 250 mM. Finally, the pure fraction of the protein was loaded onto a G-25 column to obtain the protein in the formulation buffer (PBS). This preparation was used for immunological studies.

Example 23

Antigenic characterization of PLH3

The purified fraction of PLH3 was characterized either by its recognition by different polyclonal sera and/or murine monoclonal antibodies, as well as by positive human sera to Dengue (table 26).

The highest recognitions in Dot blotting were obtained with the HMAF anti-DEN-1. The recognition by HMAF against the other serotypes was lower than in the case of serotype 1. The antibodies generated by other flavivirus like the Yellow Fever virus and the Saint Louis Encephalitis virus had not any recognition at all. Finally, the reactivity against three human sera of high titers and three of low titers against DEN-1 was measured, achieving a substantial signal in both cases by Dot blotting and Western blotting.

TABLE 26

Reactivity of PLH3 protein to monoclonal and polyclonal antibodies.

| Abs** | Specificity*** | PLH3 |
|---|---|---|
| HMAF | DEN-1 | +++ |
| HMAF | DEN-2 | + |
| HMAF | DEN-3 | − |
| HMAF | DEN-4 | − |
| HMAF | EEE | − |
| HMAF | YFV | − |
| HMAF | SLV | − |
| Mab 3H5 | NT | − |

*A total of 10 μg of purified PLH3 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 24

Characterization of the Antibody Response Generated by PLH3

A total of 25 Balb/c mice were i.p immunized with 20 ug of purified PLH3 in Freund adjuvant; 10 animals were bled after four doses and the antibodies anti-DEN were evaluated by ELISA. High antibody titers against DEN-1 were obtained while, no reactivity was obtained against the rest of the serotypes (table 27 and table 30). In addition, the HI assay was done and only positive titers were found against DEN-1 (table 28 and table 30). Finally, the in vitro neutralization assay was done and neutralization titers of 1: 1280 against DEN-1 were obtained (table 29). No neutralization of the viral infection was found against the rest of the serotypes (table 30).

TABLE 27

Antibody titers against DEN-1 from the sera obtained upon immunization of mice with PLH3.

| Mouse | Titers anti-DEN-1 PLH3 | Titers anti-DEN-1 PBSControl (−) |
|---|---|---|
| 1 | 1:64000 | <1:100 |
| 2 | >1:128000 | <1:100 |
| 3 | 1:64000 | <1:100 |
| 4 | >1:128000 | <1:100 |
| 5 | 1:128000 | <1:100 |
| 6 | 1:128000 | <1:100 |
| 7 | 1:128000 | <1:100 |
| 8 | >1:128000 | <1:100 |
| 9 | 1:64000 | <1:100 |
| 10 | >1:128000 | <1:100 |

TABLE 28

Titers by HI of the sera from the animals immunized with PLH3.

| Mouse | Titers by HI* anti-DEN-1 PLH3 | Titers by HI anti-DEN-1 PBS C(−) |
|---|---|---|
| 1 | 1:320 | <1:5 |
| 2 | >1:640 | <1:5 |
| 3 | >1:640 | <1:5 |
| 4 | 1:320 | <1:5 |
| 5 | 1:320 | <1:5 |
| 6 | >1:640 | <1:5 |
| 7 | 1:320 | <1:5 |
| 8 | <1:5 | <1:5 |
| 9 | >1:640 | <1:5 |
| 10 | >1:640 | <1:5 |

*The HI titers were defined as the highest dilution capable of inhibiting the hemagglutination of goose's erythrocytes against 8 hemagglutination viral units.

TABLE 29

Viral neutralization assay with the sera of animals immunized with PLH3.

| Mouse | Neutralizing titers* anti-DEN-1 PLH3 | Neutralizing titers* anti-DEN-1 PBS C(−) |
|---|---|---|
| 1 | >1:1280 | <1:5 |
| 2 | >1:1280 | <1:5 |
| 3 | >1:1280 | <1:5 |
| 4 | 1:640 | <1:5 |
| 5 | 1:640 | <1:5 |
| 6 | >1:1280 | <1:5 |
| 7 | >1:1280 | <1:5 |
| 8 | >1:1280 | <1:5 |
| 9 | >1:1280 | <1:5 |
| 10 | >1:1280 | <1:5 |

*The neutralizing titers were defined as the highest dilution of serum having 50% reduction of the number of viral plaques.

TABLE 30

Cross-reactivity assay against all the viral serotypes by ELISA, HI and viral neutralization with the sera of animals immunized with PLH3.

| Mixture of sera* | ELISA (anti-DEN-1) | ELISA anti DEN-2) | ELISA anti-DEN-3) | ELISA (anti-DEN- 4) |
|---|---|---|---|---|
| 1(PLH3) | 1:128000 | <1/100 | <1/100 | <1/100 |
| 2(PLH3) | >1:128000 | <1/100 | <1/100 | <1/100 |
| Mixture of sera* | HI** anti-DEN-1 | HI anti-DEN-2 | HI anti-DEN-3 | HI anti-DEN-4 |
| PLH3 | >1/320 | <1/5 | <1/5 | <1/5 |
| Mixture of sera* | Neutralizing titers*** anti-DEN-1 | Neutralizing titers anti-DEN-2 | Neutralizing titers anti-DEN-3 | Neutralizing titers anti-DEN-4 |
| 1(PLH3) | >1:1280 | <1:5 | <1:5 | <1:5 |
| 2(PLH3) | >1:1280 | <1:5 | <1:5 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 25

Obtaining of pAZ1

The nucleotide sequence that codifies for the amino acids from 286 to 426 of the envelope protein from the DEN-3 virus (Seq. 39) was amplified with the oligonucleotides identified in the list of sequences as Sequence No. 11 and Sequence No.12 from the DEN-3 virus strain genotype (Osatomi K., Sumiyoshi H. Complete nucleotide sequence of dengue type 3 virus genome RNA. Virology.1990. 176 (2):643-647).

The vector was created by digestion of the pM108 His plasmid with Xba I/Bam HI, which contains the nucleotide sequence that codifies for the N-terminal region of the MDH and for a sequence of 6 histidines (Sequence No. 23). Upon ligation, the potential recombinants were analyzed by restriction enzyme digestion and positive clones were sequenced to check up the junctions. Competent cells W3110 were transformed with the selected clone, called pAZ1 (FIG. 7 and Sequence No.40). Upon growing the colony in Luria Bertani (LB) medium, a SDS-PAGE of the cellular lysate was done. As a result a 25 kDA band was obtained, which accounted for 10% of the total cellular proteins. The size of the protein obtained corresponded to the sum of the N-terminal region from the MDH protein and the DENe protein fragment from the DEN-3 virus. The protein was recognized in Immunoblotting by polyclonal antibodies (PA) anti-DEN-3 contained in the HMAF. This protein was denominated PAZ1 (Sequence No.41).

Example 26

Purification of the Protein PAZ1

The biomass obtained from the *E. coli* strain transformed with pAZ1 and grown at 37° C. was disrupted by French press. The recombinant protein was obtained preponderantly as insoluble form associated to the pellet of the cellular disruption. From the pellet, the protein was extracted with urea 7 M and the supernatant, containing the PLH1 protein, was loaded onto a G-25 column to eliminate the chaotropic agent. The fraction obtained was then loaded onto the Chelating-sepharose FF column (Pharmacia, UK), in the presence of $Cu^{++}$ ions. The protein was eluted with Imidazolee 60 mM and the obtained volume was loaded onto a G-25 column to finally obtain the protein in the formulation buffer (PBS). This preparation was used for immunological studies.

Example 27

Antigenic Characterization of PAZ1

The purified fraction of PAZ1 was characterized either by its recognition by different polyclonal sera and/or murine monoclonal antibodies, as well as by positive human sera to Dengue (table 31).

The highest recognitions in Dot blotting were obtained with the HMAF anti-DEN-3. The recognition by HMAF against the other serotypes was lower than in the case of serotype 3. The antibodies generated by other flavivirus like the Yellow Fever virus and the Saint Louis Encephalitis virus had not any recognition at all. Finally, the reactivity against three human sera of high titers and three of low titers against DEN-3 was measured, achieving a substantial signal in both cases by Dot blotting Western blotting.

TABLE 31

Reactivity of PAZ1 protein to monoclonal and polyclonal antibodies.

| Abs** | Specificity*** | PAZ1 |
|---|---|---|
| HMAF | DEN-1 | − |
| HMAF | DEN-2 | + |
| HMAF | DEN-3 | ++ |
| HMAF | DEN-4 | + |
| HMAF | EEE | − |
| HMAF | YFV | − |
| HMAF | SLV | − |
| Mab 3H5 | NT | − |

*A total of 10 μg of purified PAZ1 was applied. The intensity of the signal obtained was evaluated from + to ++.
**HMAF were used 1:100 while the Mab 3H5 was used in dilution 1:1000.
***EEE: Equine Encephalitis virus.
YFV: Yellow Fever virus.
SLV: Saint Louis Encephalitis virus.
NT: Neutralizing specific-serotype.

Example 28

Characterization of the Antibody Response Generated by PAZ1

A total of 25 Balb/c mice were i.p immunized with 35 ug of purified PAZ1 in Freund adjuvant; 10 animals were bled after four doses and the antibodies anti-DEN were evaluated by ELISA. High antibody titers against DEN-1 were obtained while, no reactivity was obtained against the rest of the serotypes (table 32 and table 35). In addition, the HI assay was done and only positive titers were found against DEN-3 (table 33 and table 35). Finally, the in vitro neutralization assay was done and neutralization titers of 1:320 against DEN-3 were obtained. However, no neutralization of the viral infection was found against the rest of the serotypes (table 34 and table 35). These results indicate the high serotype-specificity of the antibodies elicited by PAZ1.

TABLE 32

Antibody titers against DEN-3 from the sera obtained upon immunization of mice with PAZ1.

| Mouse | Titers anti-DEN-3 PAZ1 | Titers anti-DEN-3 PBSControl (−) |
|---|---|---|
| 1 | 1/64000 | <1:100 |
| 2 | 1/128000 | <1:100 |
| 3 | 1/32000 | <1:100 |
| 4 | 1/64000 | <1:100 |
| 5 | 1/64000 | <1:100 |
| 6 | 1/128000 | <1:100 |
| 7 | 1/64000 | <1:100 |
| 8 | 1/64000 | <1:100 |
| 9 | 1/128000 | <1:100 |
| 10 | 1/128000 | <1:100 |

TABLE 33

Titers by HI of the sera from the animals immunized with PAZ1.

| Mouse | Titers by HI* anti-DEN-3 PAZ1 | Titers by HI anti-DEN-3 PBS C(−) |
|---|---|---|
| 1 | >1:640 | <1:5 |
| 2 | 1:320 | <1:5 |
| 3 | 1:320 | <1:5 |
| 4 | 1:640 | <1:5 |
| 5 | <1/5 | <1:5 |
| 6 | 1:320 | <1:5 |
| 7 | <1/5 | <1:5 |
| 8 | 1:320 | <1:5 |
| 9 | >1:640 | <1:5 |
| 10 | >1:640 | <1:5 |

*The HI titers were defined as the highest dilution capable of inhibiting the hemagglutination of goose's erythrocytes against 8 hemagglutination viral units.

TABLE 34

Viral neutralization assay with the sera of animals immunized with PAZ1.

| Mouse | Neutralizing titers anti-DEN-3 PAZ1 | Neutralizing titers anti-DEN-3 PBS C(−) |
|---|---|---|
| 1 | 1:160 | <1:5 |
| 2 | 1:320 | <1:5 |
| 3 | 1:320 | <1:5 |
| 4 | 1:320 | <1:5 |
| 5 | 1:40 | <1:5 |
| 6 | 1:40 | <1:5 |
| 7 | 1:320 | <1:5 |
| 8 | 1:320 | <1:5 |
| 9 | 1:160 | <1:5 |
| 10 | 1:320 | <1:5 |

*The neutralizing titers were defined as the highest dilution of serum having 50% reduction of the number of viral plaques.

TABLE 35

Cross-reactivity assay against all the viral serotypes by ELISA, HI and viral neutralization with the sera of animals immunized with PAZ1.

| Mixture of sera* | ELISA (anti-DEN-1) | ELISA (anti-DEN-2) | ELISA (anti-DEN-3) | ELISA (anti-DEN-4) |
|---|---|---|---|---|
| 1 (PAZ1) | <1/100 | <1/100 | 1:64000 | <1/100 |
| 2 (PAZ1) | <1/100 | <1/100 | >1:128000 | <1/100 |
| **Mixture of sera*** | **HI** anti-DEN-1** | **HI anti-DEN-2** | **HI anti-DEN-3** | **HI anti-DEN-4** |
| PAZ1 | <1/5 | <1/5 | >1:320 | <1/5 |
| **Mixture of sera*** | **Neutralizing titers*** anti-DEN-1** | **Neutralizing titers anti-DEN-2** | **Neutralizing titers anti-DEN-3** | **Neutralizing titers anti-DEN-4** |
| 1(PAZ1) | <1:5 | <1:5 | 1:320 | <1:5 |
| 2(PAZ1) | <1:5 | <1:5 | 1:320 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 29

Obtaining of pAZ2

The nucleotide sequence that codifies for the amino acids from 286 to 426 of the envelope protein from the DEN-3 virus (Sequence No.39) was amplified with the oligonucleotides identified in the list of sequences as Sequence No.11 and Sequence No.13 from a DEN-3 viral strain (Osatomi K., Sumiyoshi H. Complete nucleotide sequence of dengue type 3 virus genome RNA. Virology. 1990.176(2):643–647).

The vector was created by digestion of the pM84 His plasmid with Xba I/Eco RI, which contains the nucleotide sequence that codifies for the MDH protein and for a sequence of 6 histidines (Sequence No. 26). This digestion permits the insertion of the amplified fragment by PCR within the coding region for a structural domain of the MDH protein. Upon ligation, the potential recombinants were analyzed by restriction enzyme digestion and positive clones were sequenced to check up the junctions. Competent cells MM294 were transformed with the selected clone, called pAZ2 (FIG. 8 and Sequence No.42). Upon growing the colony in LB medium, a SDS-PAGE of the cellular lysate was done. As a result a 80 kDA band was obtained, which accounted for 20% of the total cellular proteins. The size of the protein obtained corresponded to the sum of the size of the MDH protein and the DENe protein fragment from the DEN-3 virus. The protein was recognized in Immunoblotting by a HMAF anti-DEN-3 and was denominated PAZ2 (Sequence No.43).

Example 30

Purification of the PAZ2 Protein

The biomass obtained from the *E. coli* strain transformed with pAZ2 and grown at 37° C. was disrupted by French press. The recombinant protein was obtained in both forms: soluble and insoluble. The protein associated to the insoluble fraction was extracted using Urea 7 M, and the supernatant, containing the PAZ2 protein, was loaded onto a G-25 column to eliminate the chaotropic agent. The fraction obtained was then loaded onto the Chelating-sepharose FF column (Pharmacia, UK), in the presence of $Cu^{++}$ ions. The column was washed with Imidazolee 40 mM and the protein was eluted with Imidazole 100 mM. Finally, the pure fraction was loaded onto a G-25 column to obtain the protein in the formulation (PBS). This preparation was used for immunological studies.

Example 31

Antigenic Characterization of PAZ2

The purified fraction of PAZ2 was characterized either by its recognition by different polyclonal sera and/or murine monoclonal antibodies, as well as by positive human sera to Dengue (table 36).

The highest recognitions in Dot blotting were obtained with the HMAF anti-DEN-3 (higher than those obtained with PAZ1). The recognition by HMAF against the other serotypes was lower than in the case of serotype 3. The antibodies generated by other flavivirus like the Yellow Fever virus and the Saint Louis Encephalitis virus had not any recognition at all. Finally, the reactivity against five human sera of high titers and three of low titers against DEN-3 was measured, achieving a substantial signal in both cases by Western blotting and Dot blotting.

TABLE 36

Reactivity of PAZ2 protein to monoclonal and polyclonal antibodies.

| Abs** | Specificity*** | PAZ2 |
|---|---|---|
| HMAF | DEN-1 | – |
| HMAF | DEN-2 | – |
| HMAF | DEN-3 | +++ |
| HMAF | DEN-4 | + |
| HMAF | EEE | – |
| HMAF | YFV | – |
| HMAF | SLV | – |
| Mab 3H5 | NT | – |

*A total of 10 μg of purified PAZ2 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype

Example 32

Characterization of the Antibody Response Generated by PAZ2

A total of 25 Balb/c mice were i.p immunized with 20 ug of purified PAZ2 in Freund adjuvant; 10 animals were bled after four doses and the antibodies anti-DEN were evaluated by ELISA. High antibody titers against DEN-3 were obtained while, no reactivity was obtained against the rest of the serotypes (table 37 and table 40). In addition, the HI assay was done and only positive titers were found against DEN-3 (table 38 and table 40). Finally, the in vitro neutralization assay was done and neutralization titers of 1: 1280 against DEN-3 were obtained (table 39). No neutralization of the viral infection was found against the rest of the serotypes (table 40).

TABLE 37

Antibody titers against DEN-3 from the sera obtained upon immunization of mice with PAZ2.

| Mouse | Titers anti-DEN-3 PAZ2 | Titers anti-DEN-3 PBS Control (–) |
|---|---|---|
| 1 | >1:128000 | <1:100 |
| 2 | 1:128000 | <1:100 |
| 3 | >1:128000 | <1:100 |
| 4 | >1:128000 | <1:100 |
| 5 | 1:128000 | <1:100 |
| 6 | >1:128000 | <1:100 |
| 7 | 1:64000 | <1:100 |
| 8 | >1:128000 | <1:100 |
| 9 | 1:64000 | <1:100 |
| 10 | >1:128000 | <1:100 |

TABLE 38

Titers by HI of the sera from the animals immunized with PAZ2.

| Mouse | Titers anti-DEN-3 PAZ2 | Titers anti-DEN-3 PBS |
|---|---|---|
| 1 | >1:640 | <1:5 |
| 2 | 1:320 | <1:5 |
| 3 | >1:640 | <1:5 |
| 4 | >1:640 | <1:5 |
| 5 | >1:640 | <1:5 |
| 6 | 1:320 | <1:5 |
| 7 | <1:5 | <1:5 |
| 8 | 1:320 | <1:5 |
| 9 | >1:640 | <1:5 |
| 10 | >1:640 | <1:5 |

*The HI titers were defined as the highest dilution capable of inhibiting the hemagglutination of goose's erythrocytes against 8 hemagglutination viral units.

TABLE 39

Viral neutralization assay with the sera of animals immunized with PAZ2.

| Mouse | Neutralizing titers anti-DEN-3 PAZ2 | Neutralizing titers anti-DEN-3 PBS C(–) |
|---|---|---|
| 1 | >1:1280 | <1:5 |
| 2 | >1:1280 | <1:5 |
| 3 | >1:1280 | <1:5 |
| 4 | >1:1280 | <1:5 |
| 5 | >1:1280 | <1:5 |
| 6 | 1:640 | <1:5 |
| 7 | >1:1280 | <1:5 |
| 8 | 1:640 | <1:5 |
| 9 | >1:1280 | <1:5 |
| 10 | 1:640 | <1:5 |

*The neutralizing titers were defined as the highest dilution of serum having 50% reduction of the number of viral plaques.

TABLE 40

Cross-reactivity assay against all the viral serotypes by ELISA, HI and viral neutralization with the sera of animals immunized with PAZ2.

| Mixture of sera* | ELISA (anti-DEN-1) | ELISA (anti DEN-2) | ELISA (anti-DEN-3) | ELISA (anti-DEN-4) |
|---|---|---|---|---|
| 1(PAZ2) | <1/100 | <1/100 | >1:128000 | <1/100 |
| 2(PAZ2) | <1/100 | <1/100 | >1:128000 | <1/100 |
| **Mixture of sera*** | **HI** anti-DEN-1** | **HI anti-DEN-2** | **HI anti-DEN-3** | **HI anti-DEN-4** |
| PAZ2 | <1/5 | <1/5 | >1/320 | <1/5 |
| **Mixture of sera*** | **Neutralizing titers*** anti-DEN-1** | **Neutralizing titers anti-DEN-2** | **Neutralizing titers anti-DEN-3** | **Neutralizing titers anti-DEN-4** |
| 1(PAZ2) | <1:5 | <1:5 | >1:1280 | <1:5 |
| 2(PAZ2) | <1:5 | <1:5 | >1:1280 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 33

Obtaining of pAZ3

The nucleotide sequence that codifies for the amino acids from 286 to 426 of the envelope protein from the DEN-3 virus (Seq. 39) was amplified with the oligonucleotides identified in the list of sequences as Sequence No.14 and Sequence No.15 from the DEN-3 viral strain (Osatomi K., Sumiyoshi H. Complete nucleotide sequence of dengue type 3 virus genome RNA. Virology.1990. 176(2):643–647).

The vector was created by digestion of the pD4 plasmid with Bam HI/Bam HI which contains the nucleotide sequence that codifies for the MDH protein and for a sequence of 6 histidines without stop codon (Sequence No.29). This digestion permits the fusion of the amplified fragment by PCR after the C-terminal region for the MDH protein. Upon ligation, the potential recombinants were analyzed by restriction enzyme digestion and positive clones were sequenced to check up the junctions. Competent cells W3110 were transformed with the selected clone, called pAZ3 (FIG. 9 and Sequence No.44). Upon growing the colony in LB medium, a SDS-PAGE of the cellular lysate was done. As a result a 80 kDA band was obtained, which accounted for 20% of the total cellular proteins. The size of the protein obtained corresponded to the sum of the size of the MDH protein and the DENe protein fragment from the DEN-3 virus. The protein was recognized in Immunoblotting by a HMAF anti-DEN-3 and was denominated PAZ3 (Sequence No.45).

Example 34

Purification of the PAZ3 Protein

The biomass obtained from the *E. coli* strain transformed with pAZ3 and grown at 37° C. was disrupted by French press. The recombinant protein was obtained in both forms: soluble and insoluble. From the insoluble fraction, the protein was extracted using Urea 7 M, and the supernatant, containing the PAZ3 protein, was loaded onto a G-25 column to eliminate the chaotropic agent. The fraction obtained was then loaded onto the Chelating-Sepharose FF column (Pharmacia, UK), in the presence of $Cu^{++}$ ions. The colum was washed with Imidazolee 45 mM and the protein was eluted with Imidazole 230 mM. Finally, the pure fraction of the protein was loaded onto a G-25 column to obtain the protein in the formulation buffer (PBS). This preparation was used for immunological studies.

Example 35

Antigenic Characterization of PAZ3

The purified fraction of PAZ3 was characterized either by its recognition by different polyclonal sera and/or murine monoclonal antibodies, as well as by positive human sera to Dengue (table 26).

The highest recognitions in Dot blotting were obtained with the HMAF anti-DEN-3. The recognition by HMAF against the other serotypes was lower than in the case of serotype 3. The antibodies generated by other flavivirus like the Yellow Fever virus and the Saint Louis Encephalitis virus had not any recognition at all. Finally, the reactivity against three human sera of high titers and three of low titers against DEN-3 was measured, achieving a substantial signal in both cases by Dot blotting and Western blotting.

TABLE 41

Reactivity of PAZ3 protein to monoclonal and polyclonal antibodies.

| Abs** | Specificity*** | PAZ3 |
|---|---|---|
| HMAF | DEN-1 | – |
| HMAF | DEN-2 | – |
| HMAF | DEN-3 | +++ |
| HMAF | DEN-4 | + |
| HMAF | EEE | – |
| HMAF | YFV | – |
| HMAF | SLV | – |
| Mab 3H5 | NT | – |

*A total of 10 μg of purified PAZ3 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 36

Characterization of the Antibody Response Generated by PAZ3

A total of 25 Balb/c mice were i.p immunized with 20 ug of purified PAZ3 in Freund adjuvant; 10 animals were bled after four doses and the antibodies anti-DEN were evaluated by ELISA. High antibody titers against DEN-3 were obtained while, no reactivity was obtained against the rest of the serotypes (table 42 and table 45). In addition, the HI assay was done and only positive titers were found against DEN-3 (table 43 and table 45). Finally, the in vitro neutralization assay was done and neutralization titers of 1: 1280 against DEN-3 were obtained (table 44). No neutralization of the viral infection was found against the rest of the serotypes (table 45).

TABLE 42

Antibody titers against DEN-3 from the sera obtained upon immunization of mice with PAZ3.

| Mouse | Titers anti-DEN-3 PAZ3 | Titers anti-DEN-3 PBSControl (−) |
|---|---|---|
| 1 | >1:128000 | <1:100 |
| 2 | 1:128000 | <1:100 |
| 3 | >1:128000 | <1:100 |
| 4 | 1:128000 | <1:100 |
| 5 | 1:128000 | <1:100 |
| 6 | >1:128000 | <1:100 |
| 7 | >1:128000 | <1:100 |
| 8 | 1:128000 | <1:100 |
| 9 | 1:128000 | <1:100 |
| 10 | >1:128000 | <1:100 |

TABLE 43

Titers by HI of the sera from the animals immunized with PAZ3.

| Mouse | Titers by HI* anti-DEN-3 PAZ3 | Titers by HI anti-DEN-3 PBS C(−) |
|---|---|---|
| 1 | >1:640 | <1:5 |
| 2 | >1:640 | <1:5 |
| 3 | 1:320 | <1:5 |
| 4 | <1:5 | <1:5 |
| 5 | >1:640 | <1:5 |
| 6 | <1:5 | <1:5 |
| 7 | 1:320 | <1:5 |
| 8 | >1:640 | <1:5 |
| 9 | >1:640 | <1:5 |
| 10 | 1:320 | <1:5 |

*The HI titers were defined as the highest dilution capable of inhibiting the hemagglutination of goose's erythrocytes against 8 hemagglutination viral units.

TABLE 44

Viral neutralization assay with the sera of animals immunized with PAZ3.

| Mouse | Neutralizing titers anti-DEN-3 PAZ3 | Neutralizing titers anti-DEN-3 PBS C(−) |
|---|---|---|
| 1 | >1:1280 | <1:5 |
| 2 | 1:640 | <1:5 |
| 3 | >1:1280 | <1:5 |
| 4 | >1:1280 | <1:5 |
| 5 | >1:1280 | <1:5 |
| 6 | >1:1280 | <1:5 |
| 7 | >1:1280 | <1:5 |
| 8 | >1:1280 | <1:5 |
| 9 | >1:1280 | <1:5 |
| 10 | >1:1280 | <1:5 |

*The neutralizing titers were defined as the highest dilution of serum having 50% reduction of the number of viral plaques.

TABLE 45

Cross-reactivity assay against all the viral serotypes by ELISA, HI and viral neutralization with the sera of animals immunized with PAZ3.

| Mixture of sera* | ELISA (anti-DEN-1) | ELISA (anti DEN-2) | ELISA (anti-DEN-3) | ELISA (anti-DEN-4) |
|---|---|---|---|---|
| 1(PAZ3) | <1/100 | <1/100 | >1:128000 | <1/100 |
| 2(PAZ3) | <1/100 | <1/100 | 1:128000 | <1/100 |
| **Mixture of sera*** | **HI** anti-DEN-1** | **HI anti-DEN-2** | **HI anti-DEN-3** | **HI anti-DEN-4** |
| PAZ3 | <1/5 | <1/5 | >1/320 | <1/5 |
| **Mixture of sera*** | **Neutralizing titers*** anti-DEN-1** | **Neutralizing titers anti-DEN-2** | **Neutralizing titers anti-DEN-3** | **Neutralizing titers anti-DEN-4** |
| 1(PAZ3) | <1:5 | <1:5 | >1:1280 | <1:5 |
| 2(PAZ3) | <1:5 | <1:5 | >1:1280 | <1:5 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 37

Obtaining of pID1

The nucleotide sequence that codifies for the amino acids from 286 to 426 of the envelope protein from the DEN-4 virus (Sequence No.46) was amplified with the oligonucleotides identified in the list of sequences as Sequence No.17 and Sequence No.18 from the DEN4 virus strain genotype (Zhao B., Mackow E. R., Buckler-White A. J., Markoff L., Chancock R. M., Lai C. -J., Makino Y. Cloning full-length Dengue type 4 viral DNA sequences: Analysis of genes coding for structural proteins. Virology 1986. 155:77–88).

The vector was created by digestion of the pM108 His plasmid with Xba I/Bam HI, which contains the nucleotide sequence that codifies for the N-terminal region of the MDH and for a sequence of 6 histidines (Sequence No. 23). Upon ligation, the potential recombinants were analyzed by restriction enzyme digestion and positive clones were sequenced to check up the junctions. Competent cells W3110 were transformed with the selected clone, called pID1 (FIG. 10 and Sequence No.47). Upon growing the colony in Luria Bertani (LB) medium, a SDS-PAGE of the cellular lysate was done. As a result a 25 kDA band was obtained, which accounted for 10% of the total cellular proteins. The size of the protein obtained corresponded to the sum of the N-terminal region from the MDH protein and the DENe protein fragment from the DEN-4 virus. The protein was recognized in Immunoblotting by polyclonal antibodies (PA) anti-DEN4 contained in the HMAF. This protein was denominated PID1 (Sequence No.48).

Example 38

Purification of the Protein PID1

The biomass obtained from the *E. coli* strain transformed with pID1 and grown at 37° C. was disrupted by French press. The recombinant protein was obtained preponderantly as insoluble form associated to the pellet of the cellular disruption. From the pellet, the protein was extracted with urea 6 M and the supernatant, containing the PID1 protein, was loaded onto a G-25 column to eliminate the chaotropic agent. The fraction obtained was then loaded onto the Chelating-sepharose FF column (Pharmacia, UK), in the presence of $Cu^{++}$ ions. The protein was eluted with Imidazolee 60 mM and the obtained volume was loaded onto a G-25 column to finally obtain the protein in the formulation buffer (PBS). This preparation was used for immunological studies.

Example 39

Antigenic Characterization of PID1

The purified fraction of PID1 was characterized either by its recognition by different polyclonal sera and/or murine monoclonal antibodies, as well as by positive human sera to Dengue (table 46).

The highest recognitions in Dot blotting were obtained with the HMAF anti-DEN4. The recognition by HMAF against the other serotypes was lower than in the case of serotype 4. The antibodies generated by other flavivirus like the Yellow Fever virus and the Saint Louis Encephalitis virus had not any recognition at all. Finally, the reactivity against three human sera of high titers and three of low titers against DEN4 was measured, achieving a substantial signal in both cases by Dot blotting Western blotting.

TABLE 46

Reactivity of PID1 protein to monoclonal and polyclonal antibodies.

| Abs** | Specificity*** | PID1 |
|---|---|---|
| HMAF | DEN-1 | – |
| HMAF | DEN-2 | – |
| HMAF | DEN-3 | + |
| HMAF | DEN-4 | ++ |
| HMAF | EEE | – |
| HMAF | YFV | – |
| HMAF | SLV | – |
| Mab 3H5 | NT | – |

*A total of 10 μg of purified PID1 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 40

Characterization of the Antibody Response Generated by PID1

A total of 25 Balb/c mice were i.p immunized with 35 ug of purified PID1 in Freund adjuvant; 10 animals were bled after four doses and the antibodies anti-DEN were evaluated by ELISA. High antibody titers against DEN-1 were obtained while, no reactivity was obtained against the rest of the serotypes (table 47 and table 50). In addition, the HI assay was done and only positive titers were found against DEN-4 (table 48 and table 50). Finally, the in vitro neutralization assay was done and neutralization titers of 1:320 against DEN-4 were obtained. However, no neutralization of the viral infection was found against the rest of the serotypes (table 49 and table 50). These results indicate the high serotype-specificity of the antibodies elicited by PID1.

TABLE 47

Antibody titers against DEN-4 from the sera obtained upon immunization of mice with PID1.

| Mouse | Titers anti-DEN-4 PID1 | Titers anti-DEN-4 PBS Control (–) |
|---|---|---|
| 1 | 1/128000 | <1:100 |
| 2 | 1/128000 | <1:100 |
| 3 | 1/64000 | <1:100 |
| 4 | 1/64000 | <1:100 |
| 5 | 1/128000 | <1:100 |
| 6 | 1/32000 | <1:100 |
| 7 | 1/128000 | <1:100 |
| 8 | 1/32000 | <1:100 |
| 9 | 1/128000 | <1:100 |
| 10 | 1/128000 | <1:100 |

TABLE 48

Titers by HI of the sera from the animals immunized with PID1.

| Mouse | Titers by HI* anti-DEN-4 PID1 | Titers by HI anti-DEN-4 PBS C(–) |
|---|---|---|
| 1 | 1:320 | <1:5 |
| 2 | 1:320 | <1:5 |
| 3 | 1:640 | <1:5 |
| 4 | 1:40 | <1:5 |
| 5 | <1/5 | <1:5 |
| 6 | 1:320 | <1:5 |
| 7 | 1:640 | <1:5 |
| 8 | 1:640 | <1:5 |
| 9 | 1:40 | <1:5 |
| 10 | 1:320 | <1:5 |

*The HI titers were defined as the highest dilution capable of inhibiting the hemagglutination of goose's erythrocytes against 8 hemagglutination viral units.

TABLE 49

Viral neutralization assay with the sera of animals immunized with PID1.

| Mouse | Neutralizing titers anti-DEN-4 PID1 | Neutralizing titers anti-DEN-4 PBS C(–) |
|---|---|---|
| 1 | 1:320 | <1:5 |
| 2 | 1:80 | <1:5 |
| 3 | 1:320 | <1:5 |
| 4 | 1:320 | <1:5 |
| 5 | 1:160 | <1:5 |
| 6 | 1:320 | <1:5 |
| 7 | 1:320 | <1:5 |
| 8 | 1:320 | <1:5 |
| 9 | 1:160 | <1:5 |
| 10 | 1:40 | <1:5 |

*The neutralizing titers were defined as the highest dilution of serum having 50% reduction of the number of viral plaques.

TABLE 50

Cross-reactivity assay against all the viral serotypes by ELISA, HI and viral neutralization with the sera of animals immunized with PID1.

| Mixture of sera* | ELISA (anti-DEN-1) | ELISA (anti DEN-2) | ELISA (anti-DEN-3) | ELISA (anti-DEN-4) |
|---|---|---|---|---|
| 1(PID1) | <1/100 | <1/100 | <1/100 | 1:64000 |
| 2(PID1) | <1/100 | <1/100 | <1/100 | >1:128000 |
| **Mixture of sera*** | **HI** anti-DEN-1** | **HI anti-DEN-2** | **HI anti-DEN-3** | **HI anti-DEN-4** |
| PID1 | <1/5 | <1/5 | <1/5 | >1:320 |
| **Mixture of sera*** | **Neutralizing titers*** anti-DEN-1** | **Neutralizing titers anti-DEN-2** | **Neutralizing titers anti-DEN-3** | **Neutralizing titers anti-DEN-4** |
| 1(PID1) | <1:5 | <1:5 | <1:5 | 1:160 |
| 2(PID1) | <1:5 | <1:5 | <1:5 | 1:320 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 41

Obtaining of pID2

The nucleotide sequence that codifies for the amino acids from 286 to 426 of the envelope protein from the DEN-4 virus (Sequence No.46) was amplified with the oligonucleotides identified in the list of sequences as Sequence No.16 and Sequence No.18 from a DEN-4 viral strain (Zhao B., Mackow E. R., Buckler-White A. J., Markoff L., Chancock R. M., Lai C. -J., Makino Y. Cloning full-length Dengue type 4 viral DNA sequences: Analysis of genes coding for structural proteins. Virology 1986.155:77–88. The vector was created by digestion of the pM84 His plasmid with Xba I/Eco RI, which contains the nucleotide sequence that codifies for the MDH protein and for a sequence of 6 histidines (Sequence No. 26). This digestion permits the insertion of the amplified fragment by PCR within the coding region for a structural domain of the MDH protein. Upon ligation, the potential recombinants were analyzed by restriction enzyme digestion and positive clones were sequenced to check up the junctions. Competent cells MM294 were transformed with the selected clone, called pID2 (FIG. 11 and Sequence No.49). Upon growing the colony in LB medium, a SDS-PAGE of the cellular lysate was done. As a result a 80 kDA band was obtained, which accounted for 20% of the total cellular proteins. The size of the protein obtained corresponded to the sum of the size of the MDH protein and the DENe protein fragment from the DEN-4 virus. The protein was recognized in Immunoblotting by a HMAF anti-DEN4 and was denominated PID2 (Sequence No.50).

Example 42

Purification of the PID2 Protein

The biomass obtained from the *E. coli* strain transformed with pID2 and grown at 37° C. was disrupted by French press. The recombinant protein was obtained in both forms: soluble and insoluble. The protein associated to the insoluble fraction was extracted using Urea 6 M, and the supernatant, containing the PID2 protein, was loaded onto a G-25 column to eliminate the chaotropic agent. The fraction obtained was then loaded onto the Chelating-sepharose FF column (Pharmacia, UK), in the presence of $Cu^{++}$ ions. The column was washed with Imidazolee 30 mM and the protein was eluted with Imidazole 250 mM. Finally, the pure fraction was loaded onto a G-25 column to obtain the protein in the formulation (PBS). This preparation was used for immunological studies.

Example 43

Antigenic Characterization of PID2

The purified fraction of PID2 was characterized either by its recognition by different polyclonal sera and/or murine monoclonal antibodies, as well as by positive human sera to Dengue (table 51).

The highest recognitions in Dot blotting were obtained with the HMAF anti-DEN4 (higher than those obtained with PID1). The recognition by HMAF against the other serotypes was lower than in the case of serotype 4. The antibodies generated by other flavivirus like the Yellow Fever virus and the Saint Louis Encephalitis virus had not any recognition at all. Finally, the reactivity against five human sera of high titers and three of low titers against DEN-3 was measured, achieving a substantial signal in both cases by Western blotting and Dot blotting.

TABLE 51

Reactivity of PID2 protein to monoclonal and polyclonal antibodies.

| Abs** | Specificity*** | PID2 |
|---|---|---|
| HMAF | DEN-1 | − |
| HMAF | DEN-2 | − |
| HMAF | DEN-3 | + |
| HMAF | DEN-4 | +++ |
| HMAF | EEE | − |
| HMAF | YFV | − |
| HMAF | SLV | − |
| Mab 3H5 | NT | − |

*A total of 10 μg of purified PID2 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 44

Characterization of the Antibody Response Generated by PID2

A total of 25 Balb/c mice were i.p immunized with 20 ug of purified PID2 in Freund adjuvant; 10 animals were bled after four doses and the antibodies anti-DEN were evaluated by ELISA. High antibody titers against DEN-4 were obtained while, no reactivity was obtained against the rest of the serotypes (table 52 and table 55). In addition, the HI assay was done and only positive titers were found against DEN-4 (table 53 and table 55). Finally, the in vitro neutralization assay was done and neutralization titers of 1: 1280 against DEN-4 were obtained (table 54). No neutralization of the viral infection was found against the rest of the serotypes (table 55).

TABLE 52

Antibody titers against DEN-4 from the sera obtained upon immunization of mice with PID2.

| Mouse | Titers anti-DEN-4 PID2 | Titers anti-DEN-4 PBSControl (−) |
|---|---|---|
| 1 | 1:64000 | <1:100 |
| 2 | >1:128000 | <1:100 |
| 3 | 1:128000 | <1:100 |
| 4 | >1:128000 | <1:100 |
| 5 | 1:64000 | <1:100 |
| 6 | >1:128000 | <1:100 |
| 7 | >1:128000 | <1:100 |
| 8 | >1:128000 | <1:100 |
| 9 | >1:128000 | <1:100 |
| 10 | 1:128000 | <1:100 |

TABLE 53

Titers by HI of the sera from the animals immunized with PID2.

| Mouse | Titers by HI* anti-DEN-4 (PID2) | Titers by HI anti-DEN-4 PBS C(−) |
|---|---|---|
| 1 | 1:320 | <1:5 |
| 2 | 1:320 | <1:5 |
| 3 | 1:640 | <1:5 |
| 4 | 1:40 | <1:5 |
| 5 | <1/5 | <1:5 |
| 6 | 1:320 | <1:5 |
| 7 | 1:640 | <1:5 |
| 8 | 1:640 | <1:5 |
| 9 | 1:40 | <1:5 |
| 10 | 1:320 | <1:5 |

*The HI titers were defined as the highest dilution capable of inhibiting the hemagglutination of goose's erythrocytes against 8 hemagglutination viral units.

TABLE 54

Viral neutralization assay with the sera of animals immunized with PID2.

| Mouse | Neutralizing titers anti-DEN-4 PID2 | Neutralizing titers anti-DEN-4 PBS C(−) |
|---|---|---|
| 1 | >1:1280 | <1:5 |
| 2 | >1:1280 | <1:5 |
| 3 | >1:1280 | <1:5 |
| 4 | >1:1280 | <1:5 |
| 5 | 1:640 | <1:5 |
| 6 | >1:1280 | <1:5 |
| 7 | >1:1280 | <1:5 |
| 8 | >1:1280 | <1:5 |
| 9 | 1:640 | <1:5 |
| 10 | >1:1280 | <1:5 |

*The neutralizing titers were defined as the highest dilution of serum having 50% reduction of the number of viral plaques.

TABLE 55

Cross-reactivity assay against all the viral serotypes by ELISA, HI and viral neutralization with the sera of animals immunized with PID2.

| Mixture of sera* | ELISA (anti-DEN-1) | ELISA (anti DEN-2) | ELISA (anti-DEN-3) | ELISA (anti-DEN-4) |
|---|---|---|---|---|
| 1(PID2) | <1/100 | <1/100 | <1/100 | >1:128000 |
| 2(PID2) | <1/100 | <1/100 | <1/100 | 1:64000 |
| **Mixture of sera*** | **HI** anti-DEN-1** | **HI anti-DEN-2** | **HI anti-DEN-3** | **HI anti-DEN-4** |
| PID2 | <1/5 | <1/5 | <1/5 | >1/320 |
| **Mixture of sera*** | **Neutralizing titers*** anti-DEN-1** | **Neutralizing titers anti-DEN-2** | **Neutralizing titers anti-DEN-3** | **Neutralizing titers anti-DEN-4** |
| 1(PID2) | <1:5 | <1:5 | <1:5 | >1:1280 |
| 2(PID2) | <1:5 | <1:5 | <1:5 | >1:1280 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 45

Obtaining of pID3

The nucleotide sequence that codifies for the amino acids from 286 to 426 of the envelope protein from the DEN4 virus (Sequence No.46) was amplified with the oligonucleotides identified in the list of sequences as Sequence No.19 and Sequence No.20 from the DEN4 viral strain (Zhao B., Mackow E. R., Buckler-White A. J., Markoff L., Chancock R. M., Lai C. -J., Makino Y. Cloning full-length Dengue type 4 viral DNA sequences: Analysis of genes coding for structural proteins. Virology 1986.155:77–88).

The vector was created by digestion of the pD4 plasmid with Bam HI/Bam HI which contains the nucleotide sequence that codifies for the MDH protein and for a sequence of 6 histidines without stop codon (Sequence No.29). This digestion permits the fusion of the amplified fragment by PCR after the C-terminal region for the MDH protein. Upon ligation, the potential recombinants were analyzed by restriction enzyme digestion and positive clones were sequenced to check up the junctions. Competent cells W3110 were transformed with the selected clone, called pID3 (FIG. 12 and Sequence No.51). Upon growing the colony in LB medium, a SDS-PAGE of the cellular lysate was done. As a result a 80 kDA band was obtained, which accounted for 20% of the total cellular proteins. The size of the protein obtained corresponded to the sum of the size of the MDH protein and the DENe protein fragment from the DEN4 virus. The protein was recognized in Immunoblotting by a HMAF anti-DEN-4 and was denominated PID3 (Sequence No.52).

Example 46

Purification of the Protein PID3

The biomass obtained from the *E. coli* strain transformed with pID3 and grown at 37° C. was disrupted by French press. The recombinant protein was obtained in both forms:

soluble and insoluble. From the insoluble fraction, the protein was extracted using Urea 6 M, and the supernatant, containing the PID3 protein, was loaded onto a G-25 column to eliminate the chaotropic agent. The fraction obtained was then loaded onto the Chelating-Sepharose FF column (Pharmacia, UK), in the presence of $Cu^{++}$ ions. The colum was washed with Imidazolee 45 mM and the protein was eluted with Imidazole 200 mM. Finally, the pure fraction of the protein was loaded onto a G-25 column to obtain the protein in the formulation buffer (PBS). This preparation was used for immunological studies.

Example 47

Antigenic Characterization of PID3

The purified fraction of PID3 was characterized either by its recognition by different polyclonal sera and/or murine monoclonal antibodies, as well as by positive human sera to Dengue (table 56).

The highest recognitions in Dot blotting were obtained with the HMAF anti-DEN4. The recognition by HMAF against the other serotypes was lower than in the case of serotype 4. The antibodies generated by other flavivirus like the Yellow Fever virus and the Saint Louis Encephalitis virus had not any recognition at all. Finally, the reactivity against three human sera of high titers and three of low titers against DEN4 was measured, achieving a substantial signal in both cases by Dot blotting and Western blotting.

TABLE 56

Reactivity of PID3 protein to monoclonal and polyclonal antibodies.

| Abs** | Specificity*** | PID3 |
|---|---|---|
| HMAF | DEN-1 | – |
| HMAF | DEN-2 | – |
| HMAF | DEN-3 | + |
| HMAF | DEN-4 | +++ |
| HMAF | EEE | – |
| HMAF | YFV | – |
| HMAF | SLV | – |
| Mab 3H5 | NT | – |

*A total of 10 μg of purified PID3 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 48

Characterization of the Antibody Response Generated by PID3

A total of 25 Balb/c mice were i.p immunized with 20 ug of purified PAZ3 in Freund adjuvant; 10 animals were bled after four doses and the antibodies anti-DEN were evaluated by ELISA. High antibody titers against DEN-4 were obtained while, no reactivity was obtained against the rest of the serotypes (table 57 and table 60). In addition, the HI assay was done and only positive titers were found against DEN4 (table 58 and table 60). Finally, the in vitro neutralization assay was done and neutralization titers of 1: 1280 against DEN4 were obtained (table 59). No neutralization of the viral infection was found against the rest of the serotypes (table 60).

TABLE 57

Antibody titers against DEN-4 from the sera obtained upon immunization of mice with PID3.

| Mouse | Titers anti-DEN-4 (PID3) | Titers anti-DEN-4 PBSControl (–) |
|---|---|---|
| 1 | >1:128000 | <1:100 |
| 2 | >1:128000 | <1:100 |
| 3 | >1:128000 | <1:100 |
| 4 | 1:64000 | <1:100 |
| 5 | 1:64000 | <1:100 |
| 6 | >1:128000 | <1:100 |
| 7 | 1:128000 | <1:100 |
| 8 | >1:128000 | <1:100 |
| 9 | 1:128000 | <1:100 |
| 10 | >1:128000 | <1:100 |

TABLE 58

Titers by HI of the sera from the animals immunized with PID3.

| Mouse | Titers by HI* anti-DEN-4 PID3 | Titers by HI anti-DEN-4 PBS C(–) |
|---|---|---|
| 1 | >1:640 | <1:5 |
| 2 | 1:320 | <1:5 |
| 3 | >1:640 | <1:5 |
| 4 | >1:640 | <1:5 |
| 5 | <1:5 | <1:5 |
| 6 | >1:640 | <1:5 |
| 7 | 1:320 | <1:5 |
| 8 | >1:640 | <1:5 |
| 9 | 1:320 | <1:5 |
| 10 | >1:640 | <1:5 |

*The HI titers were defined as the highest dilution capable of inhibiting the hemagglutination of goose's erythrocytes against 8 hemagglutination viral units.

TABLE 59

Viral neutralization assay with the sera of animals immunized with PID3.

| Mouse | Neutralizing titers* anti-DEN-4 PID3 | Neutralizing titers anti-DEN-4 PBS C(–) |
|---|---|---|
| 1 | >1:1280 | <1:5 |
| 2 | >1:1280 | <1:5 |
| 3 | >1:1280 | <1:5 |
| 4 | >1:1280 | <1:5 |
| 5 | >1:1280 | <1:5 |
| 6 | >1:1280 | <1:5 |
| 7 | >1:1280 | <1:5 |
| 8 | 1:640 | <1:5 |
| 9 | >1:1280 | <1:5 |
| 10 | >1:1280 | <1:5 |

*The neutralizing titers were defined as the highest dilution of serum having 50% reduction of the number of viral plaques.

TABLE 60

Cross-reactivity assay against all the viral serotypes by ELISA, HI and viral neutralization with the sera of animals immunized with PID3.

| Mixture of sera* | ELISA (anti-DEN-1) | ELISA (anti DEN-2) | ELISA (anti-DEN-3) | ELISA (anti-DEN-4) |
|---|---|---|---|---|
| 1(PID3) | <1/100 | <1/100 | <1/100 | >1:128000 |
| 2(PID3) | <1/100 | <1/100 | <1/100 | 1:128000 |
| **Mixture of sera*** | **HI** anti-DEN-1** | **HI anti-DEN-2** | **HI anti-DEN-3** | **HI anti-DEN-4** |
| PID3 | <1/5 | <1/5 | <1/5 | >1/320 |
| **Mixture of sera*** | **Neutralizing titers*** anti-DEN-1** | **Neutralizing titers anti-DEN-2** | **Neutralizing titers anti-DEN-3** | **Neutralizing titers anti-DEN-4** |
| 1(PID3) | <1:5 | <1:5 | <1:5 | >1:1280 |
| 2(PID3) | <1:5 | <1:5 | <1:5 | >1/1280 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 49

Obtaining of pD4D2

The nucleotide sequence that codifies for the amino acids 286 to 426 of the E protein from the DEN-4 virus (Sequence No.46) was amplified with the oligonuclotides identified in the sequencing list as Sequence No.16 and Sequence No.21 from the viral strain of DEN-4 (Zhao B., Mackow E. R., Buckler-White A. J., Markoff L., Chancock R. M., Lai C. -J., Makino Y. Cloning full-length Dengue type 4 viral DNA sequences: Analysis of genes coding for structural proteins. Virology 1986. 155:77-88).

The vector was created by digestion Xba/Xba I of the pLL3 plasmid, which contains the MDH gene plus a sequence of 6 histidines in the 3' region of the gene and the sequence of the E fragment from DEN-2 in the 3' end. As result, two regions of the E protein from serotypes 2 and 4 were obtained, fused to the same MDH gene. Upon ligation, the potential recombinants were analyzed by restriction enzyme digestion and positive clones were sequenced to check up the junctions. Competent cells MM294 were transformed with the selected clone, called pD4D2 (FIG. 13 and Sequence No.53). Upon growing the colony in LB medium, a SDS-PAGE of the cellular lysate was done. As a result a 110 kDa band was obtained, which accounted for 20% of the total cellular proteins. The size of the protein obtained corresponded to the sum of the MDH protein and the two fragments of the DENe protein from Dengue virus. This protein was recognized by polyclonal antibodies anti-DEN-2 and anti-DEN-4 contained in the HMAF. This protein was denominated PD4D2 (Sequence No.54).

Example 50

Purification of the PD4D2 Protein

The biomass obtained from the *E. coli* strain transformed with pD4D2 and grown at 37° C. was disrupted by French press. The recombinant protein was obtained either soluble or insoluble. From the pellet the protein was extracted with urea 6 M and the supernatant, containing the PD4D2 protein, was loaded onto a G-25 column to eliminate the chaotropic agent. The fraction obtained was then loaded onto the Chelating-sepharose FF column (Pharmacia, UK), in the presence of $Cu^{++}$ ions. A washing step was done with Imidazolee 30 mM and the protein was eluted with Imidazole 250 mM. Finally, the pure preparation was loaded onto a G-25 column to obtain the protein in the formulation buffer and use it for immunological studies.

Example 51

Antigenic Characterization of PD4D2

The purified fraction of PD4D2 was characterized either by its recognition by different polyclonal sera and/or murine monoclonal antibodies, as well as by positive human sera to Dengue (table 61).

The highest recognitions in Dot blotting were obtained with the HMAF anti-DEN-2 and anti-DEN-4. The recognition of the two other serotypes was less than for the case of serotypes 2 and 4. The antibodies generated by other flavivirus like the Yellow Fever virus and the Saint Louis Encephalitis virus had not any recognition at all. On the other hand, the Mab 3H5 had reactivity indeed, similar to that obtained for PLL2 and PLL3.

Finally, the reactivity against human sera of high and low titers against DEN-2 and DEN-4 was measured, achieving a substantial signal for both cases by Western blotting and Dot blotting.

TABLE 61

Reactivity of PD4D2 protein against monoclonal and polyclonal antibodies.

| Abs** | Specificity*** | PD4D2 |
|---|---|---|
| HMAF | DEN-1 | – |
| HMAF | DEN-2 | +++ |
| HMAF | DEN-3 | – |
| HMAF | DEN-4 | +++ |
| HMAF | EEE | – |
| HMAF | YFV | – |
| HMAF | SLV | – |
| Mab 3H5 | NT | – |

*A total of 10 μg of purified PD4D2 was applied. The intensity of the signal obtained was evaluated from + to ++.
**HMAF were used 1:100 while the Mab 3H5 was used in dilution 1:1000.
***EEE: Equine Encephalitis virus. YFV: Yellow Fever virus. SLV: Saint Louis Encephalitis virus. NT: Neutralizing specific-serotype.

Example 52

Characterization of the Antibody Response Generated by PD4D2

A total of 25 Balb/c mice were i.p immunized with 20 ug of purified PD4D2 in Freund adjuvant; 10 animals were bled after four doses and the antibodies anti-DEN were evaluated by ELISA. High antibody titers against DEN-2 and DEN4 were obtained while, no reactivity was obtained against the rest of the serotypes (table 62 and table 65). In addition, the hemagglutination inhibition assay (HI) was done and only positive titers were found against DEN-2 and DEN-4 (table 63 and table 65). Finally, the in vitro neutralization assay was done and neutralization titers of >1:1280 against DEN-2 and >1:1280 against DEN-4 were obtained (table 64). No neutralization of the viral infection was found against the rest of the serotypes (table 65).

TABLE 62

Antibody titers against DEN-2 and DEN-4 from the sera obtained upon immunization of mice with PD4D2.

| | Titers by ELISA (PD4D2) | | Titers by ELISA PBS C(−) | |
|---|---|---|---|---|
| Mouse | Anti-DEN-4 | Anti-DEN-2 | Anti-DEN-4 | Anti-DEN-2 |
| 1 | >1:128000 | >1:128000 | <1:100 | <1:100 |
| 2 | 1:128000 | 1:128000 | <1:100 | <1:100 |
| 3 | >1:128000 | >1:128000 | <1:100 | <1:100 |
| 4 | >1:128000 | >1:128000 | <1:100 | <1:100 |
| 5 | 1:64000 | >1:128000 | <1:100 | <1:100 |
| 6 | >1:128000 | 1:128000 | <1:100 | <1:100 |
| 7 | 1:64000 | >1:128000 | <1:100 | <1:100 |
| 8 | >1:128000 | >1:128000 | <1:100 | <1:100 |
| 9 | >1:128000 | 1:128000 | <1:100 | <1:100 |
| 10 | 1:128000 | >1:128000 | <1:100 | <1:100 |

TABLE 63

Titers by HI of the sera from the animals immunized with PD4D2.

| | Titers by HI (PD4D2) | | Titers by HI PBS C(−) | |
|---|---|---|---|---|
| Mouse | Anti-DEN-4 | Anti-DEN-2 | Anti-DEN-4 | Anti-DEN-2 |
| 1 | >1:640 | >1:640 | <1:5 | <1:5 |
| 2 | >1:640 | >1:640 | <1:5 | <1:5 |
| 3 | >1:640 | 1:320 | <1:5 | <1:5 |
| 4 | >1:640 | >1:640 | <1:5 | <1:5 |
| 5 | 1:320 | 1:640 | <1:5 | <1:5 |
| 6 | >1:640 | >1:640 | <1:5 | <1:5 |
| 7 | >1:640 | >1:640 | <1:5 | <1:5 |
| 8 | 1:320 | 1:320 | <1:5 | <1:5 |
| 9 | 1:320 | 1:320 | <1:5 | <1:5 |
| 10 | >1:640 | >1:640 | <1:5 | <1:5 |

*The HI titers were defined as the highest dilution capable of inhibiting the hemagglutination of goose's erythrocytes against 8 hemagglutination viral units.

TABLE 64

Viral neutralization assay with the sera of animals immunized with PD4D2.

| | Neutralizing titers* (PD4D2) | | Neutralizing titers PBS C(−) | |
|---|---|---|---|---|
| Mouse | Anti-DEN-4 | Anti-DEN-2 | Anti-DEN-4 | Anti-DEN-2 |
| 1 | >1:1280 | >1:1280 | <1:5 | <1:5 |
| 2 | >1:1280 | >1:1280 | <1:5 | <1:5 |
| 3 | 1:1280 | 1:1280 | <1:5 | <1:5 |
| 4 | >1:1280 | >1:1280 | <1:5 | <1:5 |
| 5 | 1:640 | 1:1280 | <1:5 | <1:5 |
| 6 | >1:1280 | >1:1280 | <1:5 | <1:5 |
| 7 | >1:1280 | >1:1280 | <1:5 | <1:5 |
| 8 | 1:640 | >1:1280 | <1:5 | <1:5 |
| 9 | >1:1280 | >1:1280 | <1:5 | <1:5 |
| 10 | >1:1280 | >1:1280 | <1:5 | <1:5 |

*The neutralizing titers were defined as the highest dilution of serum having 50% reduction of the number of viral plaques.

TABLE 65

Cross-reactivity assay against all the viral serotypes by ELISA, HI and viral neutralization with the sera of animals immunized with PD4D2.

| Mixture of sera* | ELISA (anti-DEN-1) | ELISA (anti DEN-2) | ELISA (anti-DEN-3) | ELISA (anti-DEN-4) |
|---|---|---|---|---|
| 1(PD4D2) | <1/100 | >1:128000 | <1/100 | 1:64000 |
| 2(PD4D2) | <1/100 | >1:128000 | <1/100 | >1:128000 |
| **Mixture of sera*** | **HI** anti-DEN-1** | **HI anti-DEN-2** | **HI anti-DEN-3** | **HI anti-DEN-4** |
| PD4D2 | <1:5 | >1:320 | <1:5 | >1:320 |
| **Mixture of sera*** | **Neutralizing titers*** anti-DEN-1** | **Neutralizing titers anti-DEN-2** | **Neutralizing titers anti-DEN-3** | **Neutralizing titers anti-DEN-4** |
| 1(PD4D2) | <1:5 | >1:1280 | <1:5 | >1:1280 |
| 2(PD4D2) | <1:5 | >1:1280 | <1:5 | >1:1280 |

*Each mixture was formed by three sera.
**The HI titers were defined as the highest dilution capable of inhibiting the hemagglutination of goose's erythrocytes against 8 hemagglutination viral units.
***The neutralizing titers were defined as the highest dilution of serum having 50% reduction of the number of viral plaques.

Example 53

Protection Assay

For the evaluation of the protection conferred to mice immunized with all the assayed variants upon challenge with homologous lethal DEN, 15 mice of each group were used. Each animal received one dose of 100 $LD_{50}$ of lethal DEN by intracraneal inoculation and they were observed during 21 days to study the percentage of lethality. As positive controls, groups of 15 mice immunized with the four viral preparations (DEN-1, DEN-2, DEN-3 and DEN-4) were used. All the mice of these control groups survived while mice from the negative control group become sick between 7–11 days after challenge; therefore, achieving a 100% of mortality. Finally, groups immunized with the fusion proteins under study had between an 80% and 100% of protection and in all the cases, significant differences with respect to the control group were found (table 66).

TABLE 66

Percentage of survival in mice immunized with the protein variants assayed upon challenge with the homologous lethal Dengue virus.

| Immunogen | Percentage of survival* |
|---|---|
| PBS | 0 |
| DEN-1 | 100 |
| DEN-2 | 100 |
| DEN-3 | 100 |
| DEN-4 | 100 |
| PLL1 | 86 |
| PLL2 | 100 |
| PLL3 | 100 |
| PLH1 | 80 |
| PLH2 | 100 |
| PLH3 | 100 |
| PAZ1 | 80 |

TABLE 66-continued

Percentage of survival in mice immunized with the protein variants assayed upon challenge with the homologous lethal Dengue virus.

| Immunogen | Percentage of survival* |
|---|---|
| PAZ2 | 100 |
| PAZ3 | 100 |
| PID1 | 86 |
| PID2 | 100 |
| PID3 | 100 |
| PD4D2 | 100 (DEN-4) |
| | 100 (DEN-2) |

*It was calculated: (# of mice survived)/(# total of mice). Data of survivors were taken 21 after challenge. In the case of mice immunized with pD4D2, 15 were challenged with DEN-4 and 15 with DEN-2.

Example 54

Lymphoproliferative Response

Animals from different groups immunized with the chimeric proteins containing the E fragment from DEN-2 (PLL1, PLL2 and PLL3), and a placebo group, were sacrified 15 days after the last dose. Then, the spleen of the animals was harvested and the lymphoproliferative response against the four serotypes of Dengue virus was studied. Table 67 shows the results of the stimulation indexes obtained, which demonstrate that a serotype specific response was achieved.

TABLE 67

Stimulation indexes, against the four Dengue viral serotypes, of lymphocytes from mice immunized with PLL1, PLL2 and PLL3.

| | PLL1 | PLL2 | PLL3 | C(−) |
|---|---|---|---|---|
| DEN-1 | 1.3* | 1.0 | 0.8 | 1.2 |
| DEN-2 | 12.5 | 10.3 | 8.9 | 1.4 |
| DEN-3 | 1.0 | 1.6 | 1.8 | 1.4 |
| DEN-4 | 1.7 | 1.5 | 1.7 | 1.1 |
| Control Antigen | 1.1 | 1.0 | 1.3 | 0.9 |
| PHA** | 13.3 | 16.5 | 11.1 | 12.0 |

*Stimulation index: cocient of the counts per minute of the samples between the counts per minute of the control of the spontaneous synthesis of DNA.

**mitogen: Phytohemagglutinin.

What is claimed is:

1. A recombinant chimeric proteins comprising (i) a fragment of the E protein from Flavivirus and (ii) the amino acid sequence encoded by SEQ. ID. NO: 29, wherein the chimeric protein is capable of inducing a humoral immune response of neutralizing and protective antibodies in a recipient, serotype-specific against each serotype of Dengue virus, when the protein is present in a pharmaceutical preparation.

2. A recombinant chimeric protein comprising: (i) a fragment of the E protein from Flavivirus and (ii) the amino acid sequence encoded by SEQ. ID. NO: 29, wherein the chimeric protein is capable of inducing a humoral immune response of neutralizing and protective antibodies in a recipient, specific against a homologous serotype of Dengue virus.

3. A chimeric protein PLL3 comprising SEQ. ID. NO: 31.

4. A pharmaceutical preparation comprising a chimeric protein described in claim 1 and a pharmacological vehicle, wherein the preparation is capable of inducing a protective immune response against Dengue virus in a recipient.

5. A pharmaceutical preparation according to claim 4, wherein said preparation is a protective or therapeutic agent against the Dengue viruses, for oral, intramuscular, subcutaneous, mucosal or intravenous use.

6. A diagnostic composition comprising a protein described in claim 1 useful for the diagnosis and serotyping of Dengue virus.

7. A chimeric protein PLL3 according to claim 3, wherein SEQ. ID. NO: 31 is the expression product of SEQ. ID. NO: 30.

* * * * *

SEQUENCE LISTING

```
<160> NUMBER OF SEQ ID NOS: 54

<210> SEQ ID NO 1
<211> LENGTH: 25
<212> TYPE: DNA
<213> ORGANISM: Escherichia coli
<220> FEATURE:
<221> NAME/KEY: primer_bind
<222> LOCATION: (1)..(25)
<223> OTHER INFORMATION: Sequence of the Xba-I primer for the
      amplification of DENe-2 fragment

<400> SEQUENCE: 1

cttctagaca ggctgcgcat ggaca                                  25


<210> SEQ ID NO 2
<211> LENGTH: 29
<212> TYPE: DNA
<213> ORGANISM: Escherichia coli
<220> FEATURE:
<221> NAME/KEY: primer_bind
<222> LOCATION: (1)..(29)
<223> OTHER INFORMATION: Sequence of the Bam-HI primer for the
      amplification of DENe-2 fragment

<400> SEQUENCE: 2

gtggatcctt accctcccag gcttccaaa                              29


<210> SEQ ID NO 3
<211> LENGTH: 25
<212> TYPE: DNA
<213> ORGANISM: Escherichia coli
<220> FEATURE:
<221> NAME/KEY: primer_bind
<222> LOCATION: (1)..(25)
<223> OTHER INFORMATION: Sequence of the Eco-RI primer for the
      amplification of DENe-2 fragment
```

```
<400> SEQUENCE: 3

atgaattcac gcctcccaga gatcc                                          25


<210> SEQ ID NO 4
<211> LENGTH: 21
<212> TYPE: DNA
<213> ORGANISM: Escherichia coli
<220> FEATURE:
<221> NAME/KEY: primer_bind
<222> LOCATION: (1)..(21)
<223> OTHER INFORMATION: Sequence of the Bam-HI primer for the
      amplification of DENe-2 fragment

<400> SEQUENCE: 4

cttggatcca ggctgagaat g                                              21


<210> SEQ ID NO 5
<211> LENGTH: 31
<212> TYPE: DNA
<213> ORGANISM: Escherichia coli
<220> FEATURE:
<221> NAME/KEY: primer_bind
<222> LOCATION: (1)..(31)
<223> OTHER INFORMATION: Sequence of the Bam-HI primer for the
      amplification of DENe-2 fragment

<400> SEQUENCE: 5

gaggatcctt aaccacccag agacccaaaa t                                   31


<210> SEQ ID NO 6
<211> LENGTH: 25
<212> TYPE: DNA
<213> ORGANISM: Escherichia coli
<220> FEATURE:
<221> NAME/KEY: primer_bind
<222> LOCATION: (1)..(25)
<223> OTHER INFORMATION: Sequence of the Xba-I primer for the
      amplification of DENe-1 fragment

<400> SEQUENCE: 6

cttctagaca ggctcaaaat ggata                                          25


<210> SEQ ID NO 7
<211> LENGTH: 28
<212> TYPE: DNA
<213> ORGANISM: Escherichia coli
<220> FEATURE:
<221> NAME/KEY: primer_bind
<222> LOCATION: (1)..(28)
<223> OTHER INFORMATION: Sequence of the Bam-HI primer for the
      amplification of DENe-1 fragment

<400> SEQUENCE: 7

gaggatcctt acccgccaat agaaccga                                       28


<210> SEQ ID NO 8
<211> LENGTH: 25
<212> TYPE: DNA
<213> ORGANISM: Escherichia coli
<220> FEATURE:
<221> NAME/KEY: primer_bind
<222> LOCATION: (1)..(25)
<223> OTHER INFORMATION: Sequence of the Eco-RI primer for the
      amplification of DENe-1 fragment

<400> SEQUENCE: 8

acgaattcac ccctcctata gatcc                                          25
```

-continued

```
<210> SEQ ID NO 9
<211> LENGTH: 24
<212> TYPE: DNA
<213> ORGANISM: Escherichia coli
<220> FEATURE:
<221> NAME/KEY: primer_bind
<222> LOCATION: (1)..(24)
<223> OTHER INFORMATION: Sequence of the Bam-HI primer for the
      amplification of DENe-1 fragment

<400> SEQUENCE: 9

acaccttgga tccagactaa aaat                                          24


<210> SEQ ID NO 10
<211> LENGTH: 26
<212> TYPE: DNA
<213> ORGANISM: Escherichia coli
<220> FEATURE:
<221> NAME/KEY: primer_bind
<222> LOCATION: (1)..(26)
<223> OTHER INFORMATION: Sequence of the Bam-HI primer for the
      amplification of DENe-1 fragment

<400> SEQUENCE: 10

ccggatccgt gaattaccca cctata                                        26


<210> SEQ ID NO 11
<211> LENGTH: 29
<212> TYPE: DNA
<213> ORGANISM: Escherichia coli
<220> FEATURE:
<221> NAME/KEY: primer_bind
<222> LOCATION: (1)..(29)
<223> OTHER INFORMATION: Sequence of the Xba-I primer for the
      amplification of DENe-3 fragment

<400> SEQUENCE: 11

tttctagata gactcaagat ggacaaatt                                     29


<210> SEQ ID NO 12
<211> LENGTH: 28
<212> TYPE: DNA
<213> ORGANISM: Escherichia coli
<220> FEATURE:
<221> NAME/KEY: primer_bind
<222> LOCATION: (1)..(28)
<223> OTHER INFORMATION: Sequence of the Bam-HI primer for the
      amplification of DENe-3 fragment

<400> SEQUENCE: 12

gaggatcctt aaccacccac tgaaccaa                                      28


<210> SEQ ID NO 13
<211> LENGTH: 25
<212> TYPE: DNA
<213> ORGANISM: Escherichia coli
<220> FEATURE:
<221> NAME/KEY: primer_bind
<222> LOCATION: (1)..(25)
<223> OTHER INFORMATION: Sequence of the Eco-RI primer for the
      amplification of DENe-3 fragment

<400> SEQUENCE: 13

aagaattcac accacccaca gatcc                                         25


<210> SEQ ID NO 14
<211> LENGTH: 23
```

```
<212> TYPE: DNA
<213> ORGANISM: Escherichia coli
<220> FEATURE:
<221> NAME/KEY: primer_bind
<222> LOCATION: (1)..(23)
<223> OTHER INFORMATION: Sequence of the Bam-HI primer for the
      amplification of DENe-3 fragment

<400> SEQUENCE: 14

acttaggatc cagactcaag atg                                          23


<210> SEQ ID NO 15
<211> LENGTH: 26
<212> TYPE: DNA
<213> ORGANISM: Escherichia coli
<220> FEATURE:
<221> NAME/KEY: primer_bind
<222> LOCATION: (1)..(26)
<223> OTHER INFORMATION: Sequence of the Bam-HI primer for the
      amplification of DENe-3 fragment

<400> SEQUENCE: 15

gaggatcctt aaccacccac tgaacc                                       26


<210> SEQ ID NO 16
<211> LENGTH: 30
<212> TYPE: DNA
<213> ORGANISM: Escherichia coli
<220> FEATURE:
<221> NAME/KEY: primer_bind
<222> LOCATION: (1)..(30)
<223> OTHER INFORMATION: Sequence of the Xba-I primer for the
      amplification of DENe-4 fragment

<400> SEQUENCE: 16

cttctagaca aagtgcgtat ggagaaattg                                   30


<210> SEQ ID NO 17
<211> LENGTH: 28
<212> TYPE: DNA
<213> ORGANISM: Escherichia coli
<220> FEATURE:
<221> NAME/KEY: primer_bind
<222> LOCATION: (1)..(28)
<223> OTHER INFORMATION: Sequence of the Bam-HI primer for the
      amplification of DENe-4 fragment

<400> SEQUENCE: 17

gaggatcctt aaccaccaac agaaccaa                                     28


<210> SEQ ID NO 18
<211> LENGTH: 25
<212> TYPE: DNA
<213> ORGANISM: Escherichia coli
<220> FEATURE:
<221> NAME/KEY: primer_bind
<222> LOCATION: (1)..(25)
<223> OTHER INFORMATION: Sequence of the Eco-RI primer for the
      amplification of DENe-4 fragment

<400> SEQUENCE: 18

atgaattcag tccaccaacg ctacc                                        25


<210> SEQ ID NO 19
<211> LENGTH: 27
<212> TYPE: DNA
<213> ORGANISM: Escherichia coli
<220> FEATURE:
<221> NAME/KEY: primer_bind
```

<222> LOCATION: (1)..(27)
<223> OTHER INFORMATION: Sequence of the Bam-HI primer for the amplification of DENe-4 fragment

<400> SEQUENCE: 19
ggccatctag gatccaaagt gcgtatg 27

<210> SEQ ID NO 20
<211> LENGTH: 28
<212> TYPE: DNA
<213> ORGANISM: Escherichia coli
<220> FEATURE:
<221> NAME/KEY: primer_bind
<222> LOCATION: (1)..(28)
<223> OTHER INFORMATION: Sequence of the Bam-HI primer for the amplification of DENe-4 fragment

<400> SEQUENCE: 20
gaggatcctt agccaccaac cgaaccaa 28

<210> SEQ ID NO 21
<211> LENGTH: 26
<212> TYPE: DNA
<213> ORGANISM: Escherichia coli
<220> FEATURE:
<221> NAME/KEY: primer_bind
<222> LOCATION: (1)..(26)
<223> OTHER INFORMATION: Sequence of the primer Xba-I for the amplification of DENe-4 fragment

<400> SEQUENCE: 21
attctagaag accaccaacg gaacca 26

<210> SEQ ID NO 22
<211> LENGTH: 429
<212> TYPE: DNA
<213> ORGANISM: Escherichia coli
<220> FEATURE:
<221> NAME/KEY: gene
<222> LOCATION: (1)..(426)
<223> OTHER INFORMATION: Nucleotidic sequence coding for the aminoacids 286 to 426 of DEN-2 envelope protein

<400> SEQUENCE: 22
gacaggctga gaatggacaa actacagctc aaaggaatgt catactctat gtgtacagga 60
aagtttaaaa ttgtgaagga aatagcagaa acacaacatg gaacaatagt tatcagagta 120
caatatgaag gggacggctc tccatgtaag atcccttttg agataatgga tttggaaaaa 180
agacacgtct taggtcgcct gattacagtt aacccgatcg taacagaaaa agatagccca 240
gtcaacatag aagcagaacc tccattcgga gacagctaca tcatcatagg agtagagccg 300
ggacaattga aactcaactg gtttaagaaa ggaagttcca tcggccaaat gtttgagaca 360
acaatgagag gagcgaagag aatggccatt ttaggtgaca cagcctggga ttttggatcc 420
ctgggagga 429

<210> SEQ ID NO 23
<211> LENGTH: 168
<212> TYPE: DNA
<213> ORGANISM: Escherichia coli
<220> FEATURE:
<221> NAME/KEY: gene
<222> LOCATION: (1)..(168)
<223> OTHER INFORMATION: Nucleotidic sequence coding for the first 45 aminoacids of the MDH.

<400> SEQUENCE: 23

-continued

```
atgggccacc accaccacca ccacgccatg gtagataaaa gaatggcttt agttgaattg     60

aaagtgcccg acattggcgg aacagaaaat gtagatatta tcgcggttga agtaaacgtg    120

ggcgacacta ttgctgtgga cgataccctg attactttgg atctagac                 168


<210> SEQ ID NO 24
<211> LENGTH: 603
<212> TYPE: DNA
<213> ORGANISM: Escherichia coli
<220> FEATURE:
<221> NAME/KEY: gene
<222> LOCATION: (1)..(603)
<223> OTHER INFORMATION: Nucleotidic sequence coding for the quimeric
      protein in the plasmid pLL1

<400> SEQUENCE: 24

atgggccacc accaccacca ccacgccatg gtagataaaa gaatggcttt agttgaattg     60

aaagtgcccg acattggcgg aacagaaaat gtagatatta tcgcggttga agtaaacgtg    120

ggcgacacta ttgctgtgga cgataccctg attactttgg atctagacag gctgcgcatg    180

gacaaactac agctcaaagg aatgtcatac tctatgtgta caggaaagtt taaaattgtg    240

aaggaaatag cagaaacaca acatggaaca atagttatca gagtacaata tgaaggggac    300

ggctctccat gtaagatccc ttttgagata atggatttgg aaaaaagaca cgtcttaggt    360

cgcctgatta cagttaaccc gatcgtaaca gaaaaagata gcccagtcaa catagaagca    420

gaacctccat tcggagacag ctacatcatc ataggagtag agccgggaca attgaaactc    480

aactggttta agaaaggaag ttccatcggc caaatgtttg agacaacaat gagaggagcg    540

aagagaatgg ccattttagg tgacacagcc tgggattttg gaagcctggg agggtaagga    600

tcc                                                                  603


<210> SEQ ID NO 25
<211> LENGTH: 195
<212> TYPE: PRT
<213> ORGANISM: Escherichia coli
<220> FEATURE:
<221> NAME/KEY: CHAIN
<222> LOCATION: (1)..(195)
<223> OTHER INFORMATION: Aminoacidic sequence of the PLL1 protein

<400> SEQUENCE: 25

His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
         35                  40                  45

Thr Leu Asp Leu Asp Arg Leu Arg Met Asp Lys Leu Gln Leu Lys Gly
     50                  55                  60

Met Ser Tyr Ser Met Cys Thr Gly Lys Phe Lys Ile Val Lys Glu Ile
 65                  70                  75                  80

Ala Glu Thr Gln His Gly Thr Ile Val Ile Arg Val Gln Tyr Glu Gly
                 85                  90                  95

Asp Gly Ser Pro Cys Lys Ile Pro Phe Glu Ile Met Asp Leu Glu Lys
            100                 105                 110

Arg His Val Leu Gly Arg Leu Ile Thr Val Asn Pro Ile Val Thr Glu
        115                 120                 125

Lys Asp Ser Pro Val Asn Ile Glu Ala Glu Pro Pro Phe Gly Asp Ser
```

```
    130                 135                 140

Tyr Ile Ile Ile Gly Val Glu Pro Gly Gln Leu Lys Leu Asn Trp Phe
145                 150                 155                 160

Lys Lys Gly Ser Ser Ile Gly Gln Met Phe Glu Thr Thr Met Arg Gly
                165                 170                 175

Ala Lys Arg Met Ala Ile Leu Gly Asp Thr Ala Trp Asp Phe Gly Ser
            180                 185                 190

Leu Gly Gly
        195
```

```
<210> SEQ ID NO 26
<211> LENGTH: 1851
<212> TYPE: DNA
<213> ORGANISM: Escherichia coli
<220> FEATURE:
<221> NAME/KEY: gene
<222> LOCATION: (1)..(1851)
<223> OTHER INFORMATION: Nucleotidic sequence of the MDH in the plasmid
      pM84 His.

<400> SEQUENCE: 26

atgggccacc accaccacca ccacgccatg gtagataaaa gaatggcttt agttgaattg      60

aaagtgcccg acattggcgg aacagaaaat gtagatatta tcgcggttga agtaaacgtg     120

ggcgacacta ttgctgtgga cgataccctg attactttgg atctagattt ggatctagaa     180

gaactagtgg atcccccggg ctgcaggaat tcgatgaatt cgatggacgt acctgctgaa     240

gttgcaggcg tagtcaaaga agttaaagtt aaagtcggcg acaaaatctc tgaaggtggt     300

ttgattgtcg tcgttgaagc tgaaggcacg gcagccgctc ctaaagccga agcggctgcc     360

gccccggcgc aagaagcccc taaagctgcc gctcctgctc cgcaagccgc gcaattcggc     420

ggttctgccg atgccgagta cgacgtggtc gtattgggtg gcggtcccgg cggttactcc     480

gctgcatttg ccgctgccga tgaaggcttg aaagtcgcca tcgtcgaacg ttacaaaact     540

ttgggcggcg tttgcctgaa cgtcggctgt atcccttcca aagccttgtt gcacaatgcc     600

gccgttatcg acgaagtgcg ccacttggct gccaacggta tcaaataccc cgagccggaa     660

ctcgacatcg atatgcttcg cgcctacaaa gacggcgtag tttcccgcct cacgggcggt     720

ttggcaggta tggcgaaaag ccgtaaagtg gacgttatcc aaggcgacgg gcaattctta     780

gatccgcacc acttggaagt gtcgctgact gccggcgacg cgtacgaaca ggcagcccct     840

accggcgaga aaaaaatcgt tgccttcaaa aactgtatca ttgcagcagg cagccgcgta     900

accaaactgc ctttcattcc tgaagatccg cgcatcatcg attccagcgg cgcattggct     960

ctgaaagaag taccgggcaa actgctgatt atcggcggcg gcattatcgg cctcgagatg    1020

ggtacggttt acagcacgct gggttcgcgt ttggatgtgg ttgaaatgat ggacggcctg    1080

atgcaaggcg cagaccgcga tttggtaaaa gtatggcaaa aacaaaacga ataccgtttt    1140

gacaacatta tggtcaacac caaaaccgtt gcagttgagc cgaaagaaga cggcgtttac    1200

gttacctttg aaggcgcgaa cgcgcctaaa gagccgcaac gctacgatgc cgtattggtt    1260

gccgccggcc gcgcgcccaa cggcaaactc atcagcgcgg aaaaagcagg cgttgccgta    1320

accgatcgcg gcttcatcga agtggacaaa caaatgcgta ccaatgtgcc gcacatctac    1380

gccatcggcg acatcgtcgg tcagccgatg ttggcgcaca aagccgttca cgaaggccac    1440

gttgccgccg aaaactgcgc cggccacaaa gcctacttcg acgcacgcgt gattccgggc    1500

gttgcctaca cttcccccga agtggcgtgg gtgggcgaaa ccgaactgtc cgccaaagcc    1560
```

-continued

```
tccggccgca aaatcaccaa agccaacttc ccgtgggcgg cttccggccg tgcgattgcc   1620

aacggttgcg acaagccgtt taccaagctg atttttgatg ccgaaaccgg ccgcatcatc   1680

ggcggcggca ttgtcggtcc gaacggtggc gatatgatcg gcgaagtctg ccttgccatc   1740

gaaatgggct gcgacgcggc agacatcggc aaaaccatcc acccgcaccc gggcgaatcc   1800

atcggtatgg cggcggaagt ggcattgggt acttgtaccg acaaaaaaaa a            1851
```

<210> SEQ ID NO 27
<211> LENGTH: 2253
<212> TYPE: DNA
<213> ORGANISM: Escherichia coli
<220> FEATURE:
<221> NAME/KEY: gene
<222> LOCATION: (1)..(2253)
<223> OTHER INFORMATION: Nucleotidic sequence of the quimeric protein in the plasmid pLL2.

<400> SEQUENCE: 27

```
atgggccacc accaccacca ccacgccatg gtagataaaa gaatggcttt agttgaattg     60

aaagtgcccg acattggcgg aacagaaaat gtagatatta tcgcggttga agtaaacgtg    120

ggcgacacta ttgctgtgga cgataccctg attactttgg atctagattt ggatctagac    180

aggctgcgca tggacaaact acagctcaaa ggaatgtcat actctatgtg tacaggaaag    240

tttaaaattg tgaaggaaat agcagaaaca caacatggaa caatagttat cagagtacaa    300

tatgaagggg acggctctcc atgtaagatc ccttttgaga taatggattt ggaaaaaaga    360

cacgtcttag gtcgcctgat tacagttaac ccgatcgtaa cagaaaaaga tagcccagtc    420

aacatagaag cagaacctcc attcggagac agctacatca tcataggagt agagccggga    480

caattgaaac tcaactggtt taagaaagga agttccatcg gccaaatgtt tgagacaaca    540

atgagaggag cgaagagaat ggccatttta ggtgacacag cctgggattt tggatctctg    600

ggaggcgtga attcgatgaa ttcgatggac gtacctgctg aagttgcagg cgtagtcaaa    660

gaagttaaag ttaaagtcgg cgacaaaatc tctgaaggtg gtttgattgt cgtcgttgaa    720

gctgaaggca cggcagccgc tcctaaagcc gaagcggctg ccgcccccgc gcaagaagcc    780

cctaaagctg ccgctcctgc tccgcaagcc gcgcaattcg gcggttctgc cgatgccgag    840

tacgacgtgg tcgtattggg tggcggtccc ggcggttact ccgctgcatt tgccgctgcc    900

gatgaaggct tgaaagtcgc catcgtcgaa cgttacaaaa ctttgggcgg cgtttgcctg    960

aacgtcggct gtatcccttc caaagccttg ttgcacaatg ccgccgttat cgacgaagtg   1020

cgccacttgg ctgccaacgg tatcaaatac cccgagccgg aactcgacat cgatatgctt   1080

cgcgcctaca aagacggcgt agtttcccgc ctcacgggcg gtttggcagg tatggcgaaa   1140

agccgtaaag tggacgttat ccaaggcgac gggcaattct tagatccgca ccacttggaa   1200

gtgtcgctga ctgccggcga cgcgtacgaa caggcagccc ctaccggcga gaaaaaaatc   1260

gttgccttca aaaactgtat cattgcagca ggcagccgcg taaccaaact gcctttcatt   1320

cctgaagatc cgcgcatcat cgattccagc ggcgcattgg ctctgaaaga agtaccgggc   1380

aaactgctga ttatcggcgg cggcattatc ggcctcgaga tgggtacggt ttacagcacg   1440

ctgggttcgc gtttggatgt ggttgaaatg atggacggcc tgatgcaagg cgcagaccgc   1500

gatttggtaa aagtatggca aaaacaaaac gaataccgtt ttgacaacat tatggtcaac   1560

accaaaaccg ttgcagttga gccgaaagaa gacggcgttt acgttacctt tgaaggcgcg   1620

aacgcgccta aagagccgca acgctacgat gccgtattgg ttgccgccgg ccgcgcgccc   1680
```

```
aacggcaaac tcatcagcgc ggaaaaagca ggcgttgccg taaccgatcg cggcttcatc   1740

gaagtggaca aacaaatgcg taccaatgtg ccgcacatct acgccatcgg cgacatcgtc   1800

ggtcagccga tgttggcgca caaagccgtt cacgaaggcc acgttgccgc cgaaaactgc   1860

gccggccaca aagcctactt cgacgcacgc gtgattccgg gcgttgccta cacttccccc   1920

gaagtggcgt gggtgggcga aaccgaactg tccgccaaag cctccggccg caaaatcacc   1980

aaagccaact tcccgtgggc ggcttccggc cgtgcgattg ccaacggttg cgacaagccg   2040

tttaccaagc tgatttttga tgccgaaacc ggccgcatca tcggcggcgg cattgtcggt   2100

ccgaacggtg gcgatatgat cggcgaagtc tgccttgcca tcgaaatggg ctgcgacgcg   2160

gcagacatcg gcaaaaccat ccacccgcac ccgggcgaat ccatcggtat ggcggcggaa   2220

gtggcattgg gtacttgtac cgacaaaaaa aaa                                2253
```

<210> SEQ ID NO 28
<211> LENGTH: 748
<212> TYPE: PRT
<213> ORGANISM: Escherichia coli
<220> FEATURE:
<221> NAME/KEY: CHAIN
<222> LOCATION: (1)..(748)
<223> OTHER INFORMATION: Aminoacidic sequence of PLL2.

<400> SEQUENCE: 28

```
His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
         35                  40                  45

Thr Leu Asp Leu Asp Arg Leu Arg Met Asp Lys Leu Gln Leu Lys Gly
     50                  55                  60

Met Ser Tyr Ser Met Cys Thr Gly Lys Phe Lys Ile Val Lys Glu Ile
 65                  70                  75                  80

Ala Glu Thr Gln His Gly Thr Ile Val Ile Arg Val Gln Tyr Glu Gly
                 85                  90                  95

Asp Gly Ser Pro Cys Lys Ile Pro Phe Glu Ile Met Asp Leu Glu Lys
            100                 105                 110

Arg His Val Leu Gly Arg Leu Ile Thr Val Asn Pro Ile Val Thr Glu
        115                 120                 125

Lys Asp Ser Pro Val Asn Ile Glu Ala Glu Pro Pro Phe Gly Asp Ser
    130                 135                 140

Tyr Ile Ile Ile Gly Val Glu Pro Gly Gln Leu Lys Leu Asn Trp Phe
145                 150                 155                 160

Lys Lys Gly Ser Ser Ile Gly Gln Met Phe Glu Thr Thr Met Arg Gly
                165                 170                 175

Ala Lys Arg Met Ala Ile Leu Gly Asp Thr Ala Trp Asp Phe Gly Ser
            180                 185                 190

Leu Gly Gly Val Asn Ser Met Asn Ser Met Asp Val Pro Ala Glu Val
        195                 200                 205

Ala Gly Val Val Lys Glu Val Lys Val Lys Val Gly Asp Lys Ile Ser
    210                 215                 220

Glu Gly Gly Leu Ile Val Val Val Glu Ala Glu Gly Thr Ala Ala Ala
225                 230                 235                 240

Pro Lys Ala Glu Ala Ala Ala Ala Pro Ala Gln Glu Ala Pro Lys Ala
                245                 250                 255
```

-continued

```
Ala Ala Pro Ala Pro Gln Ala Ala Gln Phe Gly Gly Ser Ala Asp Ala
            260                 265                 270

Glu Tyr Asp Val Val Val Leu Gly Gly Gly Pro Gly Gly Tyr Ser Ala
        275                 280                 285

Ala Phe Ala Ala Ala Asp Glu Gly Leu Lys Val Ala Ile Val Glu Arg
    290                 295                 300

Tyr Lys Thr Leu Gly Gly Val Cys Leu Asn Val Gly Cys Ile Pro Ser
305                 310                 315                 320

Lys Ala Leu Leu His Asn Ala Ala Val Ile Asp Glu Val Arg His Leu
                325                 330                 335

Ala Ala Asn Gly Ile Lys Tyr Pro Glu Pro Glu Leu Asp Ile Asp Met
            340                 345                 350

Leu Arg Ala Tyr Lys Asp Gly Val Val Ser Arg Leu Thr Gly Gly Leu
        355                 360                 365

Ala Gly Met Ala Lys Ser Arg Lys Val Asp Val Ile Gln Gly Asp Gly
    370                 375                 380

Gln Phe Leu Asp Pro His His Leu Glu Val Ser Leu Thr Ala Gly Asp
385                 390                 395                 400

Ala Tyr Glu Gln Ala Ala Pro Thr Gly Glu Lys Lys Ile Val Ala Phe
                405                 410                 415

Lys Asn Cys Ile Ile Ala Ala Gly Ser Arg Val Thr Lys Leu Pro Phe
            420                 425                 430

Ile Pro Glu Asp Pro Arg Ile Ile Asp Ser Ser Gly Ala Leu Ala Leu
        435                 440                 445

Lys Glu Val Pro Gly Lys Leu Leu Ile Ile Gly Gly Gly Ile Ile Gly
    450                 455                 460

Leu Glu Met Gly Thr Val Tyr Ser Thr Leu Gly Ser Arg Leu Asp Val
465                 470                 475                 480

Val Glu Met Met Asp Gly Leu Met Gln Gly Ala Asp Arg Asp Leu Val
                485                 490                 495

Lys Val Trp Gln Lys Gln Asn Glu Tyr Arg Phe Asp Asn Ile Met Val
            500                 505                 510

Asn Thr Lys Thr Val Ala Val Glu Pro Lys Glu Asp Gly Val Tyr Val
        515                 520                 525

Thr Phe Glu Gly Ala Asn Ala Pro Lys Glu Pro Gln Arg Tyr Asp Ala
    530                 535                 540

Val Leu Val Ala Ala Gly Arg Ala Pro Asn Gly Lys Leu Ile Ser Ala
545                 550                 555                 560

Glu Lys Ala Gly Val Ala Val Thr Asp Arg Gly Phe Ile Glu Val Asp
                565                 570                 575

Lys Gln Met Arg Thr Asn Val Pro His Ile Tyr Ala Ile Gly Asp Ile
            580                 585                 590

Val Gly Gln Pro Met Leu Ala His Lys Ala Val His Glu Gly His Val
        595                 600                 605

Ala Ala Glu Asn Cys Ala Gly His Lys Ala Tyr Phe Asp Ala Arg Val
    610                 615                 620

Ile Pro Gly Val Ala Tyr Thr Ser Pro Glu Val Ala Trp Val Gly Glu
625                 630                 635                 640

Thr Glu Leu Ser Ala Lys Ala Ser Gly Arg Lys Ile Thr Lys Ala Asn
                645                 650                 655

Phe Pro Trp Ala Ala Ser Gly Arg Ala Ile Ala Asn Gly Cys Asp Lys
            660                 665                 670
```

-continued

```
Pro Phe Thr Lys Leu Ile Phe Asp Ala Glu Thr Gly Arg Ile Ile Gly
        675                 680                 685

Gly Gly Ile Val Gly Pro Asn Gly Gly Asp Met Ile Gly Glu Val Cys
    690                 695                 700

Leu Ala Ile Glu Met Gly Cys Asp Ala Ala Asp Ile Gly Lys Thr Ile
705                 710                 715                 720

His Pro His Pro Gly Glu Ser Ile Gly Met Ala Ala Glu Val Ala Leu
                725                 730                 735

Gly Thr Cys Thr Asp Leu Pro Pro Gln Lys Lys Lys
            740                 745


<210> SEQ ID NO 29
<211> LENGTH: 1821
<212> TYPE: DNA
<213> ORGANISM: Escherichia coli
<220> FEATURE:
<221> NAME/KEY: gene
<222> LOCATION: (1)..(1821)
<223> OTHER INFORMATION: Nucleotidic sequence of the MDH in the plasmid
      pD4

<400> SEQUENCE: 29

atgggccacc accaccacca ccacgccatg gtagataaaa gaatggcttt agttgaattg      60

aaagtgcccg acattggcgg acacgaaaat gtagatatta tcgcggttga agtaaacgtg     120

ggcgacacta ttgctgtgga cgataccctg attactttgg atctagaaat ggacgtacct     180

gctgaagttg caggcgtagt caaagaagtt aaagttaaag tcggcgacaa aatctctgaa     240

ggtggtttga ttgtcgtcgt tgaagctgaa ggcacggcag ccgctcctaa agccgaagcg     300

gctgccgccc cggcgcaaga agcccctaaa gctgccgctc ctgctccgca agccgcgcaa     360

ttcggcggtt ctgccgatgc cgagtacgac gtggtcgtat tgggtggcgg tcccggcggt     420

tactccgctg catttgccgc tgccgatgaa ggcttgaaag tcgccatcgt cgaacgttac     480

aaaactttgg gcggcgtttg cctgaacgtc ggctgtatcc cttccaaagc cttgttgcac     540

aatgccgccg ttatcgacga agtgcgccac ttggctgcca acggtatcaa ataccccgag     600

ccggaactcg acatcgatat gcttcgcgcc tacaaagacg gcgtagtttc ccgcctcacg     660

ggcggtttgg caggtatggc gaaaagccgt aaagtggacg ttatccaagg cgacgggcaa     720

ttcttagatc cgcaccactt ggaagtgtcg ctgactgccg gcgacgcgta cgaacaggca     780

gcccctaccg gcgagaaaaa aatcgttgcc ttcaaaaact gtatcattgc agcaggcagc     840

cgcgtaacca aactgccttt cattcctgaa gatccgcgca tcatcgattc cagcggcgca     900

ttggctctga aagaagtacc gggcaaactg ctgattatcg gcggcggcat tatcggcctc     960

gagatgggta cggtttacag cacgctgggt tcgcgtttgg atgtggttga aatgatggac    1020

ggcctgatgc aaggcgcaga ccgcgatttg gtaaaagtat ggcaaaaaca aaacgaatac    1080

cgttttgaca acattatggt caacaccaaa accgttgcag ttgagccgaa agaagacggc    1140

gtttacgtta cctttgaagg cgcgaacgcg cctaaagagc cgcaacgcta cgatgccgta    1200

ttggttgccg ccggccgcgc gcccaacggc aaactcatca gcgcggaaaa agcaggcgtt    1260

gccgtaaccg atcgcggctt catcgaagtg gacaaacaaa tgcgtaccaa tgtgccgcac    1320

atctacgcca tcggcgacat cgtcggtcag ccgatgttgg cgcacaaagc cgttcacgaa    1380

ggccacgttg ccgccgaaaa ctgcgccggc cacaaagcct acttcgacgc acgcgtgatt    1440

ccgggcgttg cctacacttc ccccgaagtg gcgtgggtgg gcgaaaccga actgtccgcc    1500

aaagcctccg gccgcaaaat caccaaagcc aacttcccgt gggcggcttc cggccgtgcg    1560
```

```
attgccaacg gttgcgacaa gccgtttacc aagctgattt ttgatgccga aaccggccgc   1620

atcatcggcg gcggcattgt cggtccgaac ggtggcgata tgatcggcga agtctgcctt   1680

gccatcgaaa tgggctgcga cgcggcagac atcggcaaaa ccatccaccc gcacccgacc   1740

ttgggcgaat ccatcggtat ggcggcggaa gtggcattgg gtacttgtac cgacctgcct   1800

ccgcaaaaga aaaaaggatc c                                              1821
```

<210> SEQ ID NO 30
<211> LENGTH: 2259
<212> TYPE: DNA
<213> ORGANISM: Escherichia coli
<220> FEATURE:
<221> NAME/KEY: gene
<222> LOCATION: (1)..(2259)
<223> OTHER INFORMATION: Nucleotidic sequence coding for the quimeric protein in the plasmid pLL3

<400> SEQUENCE: 30

```
atgggccacc accaccacca ccacgccatg gtagataaaa gaatggcttt agttgaattg     60

aaagtgcccg acattggcgg acacgaaaat gtagatatta tcgcggttga agtaaacgtg    120

ggcgacacta ttgctgtgga cgataccctg attactttgg atctagaaat ggacgtacct    180

gctgaagttg caggcgtagt caaagaagtt aaagttaaag tcggcgacaa aatctctgaa    240

ggtggtttga ttgtcgtcgt tgaagctgaa ggcacggcag ccgctcctaa agccgaagcg    300

gctgccgccc cggcgcaaga agcccctaaa gctgccgctc ctgctccgca agccgcgcaa    360

ttcggcggtt ctgccgatgc cgagtacgac gtggtcgtat tgggtggcgg tcccggcggt    420

tactccgctg catttgccgc tgccgatgaa ggcttgaaag tcgccatcgt cgaacgttac    480

aaaactttgg gcggcgtttg cctgaacgtc ggctgtatcc cttccaaagc cttgttgcac    540

aatgccgccg ttatcgacga agtgcgccac ttggctgcca acggtatcaa ataccccgag    600

ccggaactcg acatcgatat gcttcgcgcc tacaaagacg gcgtagtttc ccgcctcacg    660

ggcggtttgg caggtatggc gaaaagccgt aaagtggacg ttatccaagg cgacgggcaa    720

ttcttagatc cgcaccactt ggaagtgtcg ctgactgccg gcgacgcgta cgaacaggca    780

gcccctaccg gcgagaaaaa aatcgttgcc ttcaaaaact gtatcattgc agcaggcagc    840

cgcgtaacca aactgccttt cattcctgaa gatccgcgca tcatcgattc cagcggcgca    900

ttggctctga aagaagtacc gggcaaactg ctgattatcg gcggcggcat tatcggcctc    960

gagatgggta cggtttacag cacgctgggt tcgcgtttgg atgtggttga aatgatggac   1020

ggcctgatgc aaggcgcaga ccgcgatttg gtaaaagtat ggcaaaaaca aaacgaatac   1080

cgttttgaca acattatggt caacaccaaa accgttgcag ttgagccgaa agaagacggc   1140

gtttacgtta cctttgaagg cgcgaacgcg cctaaagagc cgcaacgcta cgatgccgta   1200

ttggttgccg ccggccgcgc gcccaacggc aaactcatca gcgcggaaaa agcaggcgtt   1260

gccgtaaccg atcgcggctt catcgaagtg gacaaacaaa tgcgtaccaa tgtgccgcac   1320

atctacgcca tcggcgacat cgtcggtcag ccgatgttgg cgcacaaagc cgttcacgaa   1380

ggccacgttg ccgccgaaaa ctgcgccggc cacaaagcct acttcgacgc acgcgtgatt   1440

ccgggcgttg cctacacttc ccccgaagtg gcgtgggtgg gcgaaaccga actgtccgcc   1500

aaagcctccg gccgcaaaat caccaaagcc aacttcccgt gggcggcttc cggccgtgcg   1560

attgccaacg gttgcgacaa gccgtttacc aagctgattt ttgatgccga aaccggccgc   1620

atcatcggcg gcggcattgt cggtccgaac ggtggcgata tgatcggcga agtctgcctt   1680
```

```
gccatcgaaa tgggctgcga cgcggcagac atcggcaaaa ccatccaccc gcacccgacc   1740

ttgggcgaat ccatcggtat ggcggcggaa gtggcattgg gtacttgtac cgacctgcct   1800

ccgcaaaaga aaaaaggatc cgacaggctg agaatggaca aactacagct caaaggaatg   1860

tcatactcta tgtgtacagg aaagtttaaa attgtgaagg aaatagcaga aacacaacat   1920

ggaacaatag ttatcagagt acaatatgaa ggggacggct ctccatgtaa gatccctttt   1980

gagataatgg atttggaaaa aagacacgtc ttaggtcgcc tgattacagt taacccgatc   2040

gtaacagaaa aagatagccc agtcaacata gaagcagaac ctccattcgg agacagctac   2100

atcatcatag gagtagagcc gggacaattg aaactcaact ggtttaagaa aggaagttcc   2160

atcggccaaa tgtttgagac aacaatgaga ggagcgaaga gaatggccat tttaggtgac   2220

acagcctggg attttgggtc tctgggtggt taaggatcc                          2259
```

<210> SEQ ID NO 31
<211> LENGTH: 745
<212> TYPE: PRT
<213> ORGANISM: Escherichia coli
<220> FEATURE:
<221> NAME/KEY: CHAIN
<222> LOCATION: (1)..(745)
<223> OTHER INFORMATION: Aminoacidic sequence of PLL3

<400> SEQUENCE: 31

```
His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
         35                  40                  45

Thr Leu Asp Met Asn Ser Met Asp Val Pro Ala Glu Val Ala Gly Val
     50                  55                  60

Val Lys Glu Val Lys Val Lys Val Gly Asp Lys Ile Ser Glu Gly Gly
 65                  70                  75                  80

Leu Ile Val Val Val Glu Ala Glu Gly Thr Ala Ala Ala Pro Lys Ala
                 85                  90                  95

Glu Ala Ala Ala Ala Pro Ala Gln Glu Ala Pro Lys Ala Ala Ala Pro
            100                 105                 110

Ala Pro Gln Ala Ala Gln Phe Gly Gly Ser Ala Asp Ala Glu Tyr Asp
        115                 120                 125

Val Val Val Leu Gly Gly Gly Pro Gly Gly Tyr Ser Ala Ala Phe Ala
    130                 135                 140

Ala Ala Asp Glu Gly Leu Lys Val Ala Ile Val Glu Arg Tyr Lys Thr
145                 150                 155                 160

Leu Gly Gly Val Cys Leu Asn Val Gly Cys Ile Pro Ser Lys Ala Leu
                165                 170                 175

Leu His Asn Ala Ala Val Ile Asp Glu Val Arg His Leu Ala Ala Asn
            180                 185                 190

Gly Ile Lys Tyr Pro Glu Pro Glu Leu Asp Ile Asp Met Leu Arg Ala
        195                 200                 205

Tyr Lys Asp Gly Val Val Ser Arg Leu Thr Gly Gly Leu Ala Gly Met
    210                 215                 220

Ala Lys Ser Arg Lys Val Asp Val Ile Gln Gly Asp Gly Gln Phe Leu
225                 230                 235                 240

Asp Pro His His Leu Glu Val Ser Leu Thr Ala Gly Asp Ala Tyr Glu
```

-continued

```
                245                 250                 255

Gln Ala Ala Pro Thr Gly Glu Lys Lys Ile Val Ala Phe Lys Asn Cys
            260                 265                 270

Ile Ile Ala Ala Gly Ser Arg Val Thr Lys Leu Pro Phe Ile Pro Glu
        275                 280                 285

Asp Pro Arg Ile Ile Asp Ser Ser Gly Ala Leu Ala Leu Lys Glu Val
    290                 295                 300

Pro Gly Lys Leu Leu Ile Ile Gly Gly Gly Ile Ile Gly Leu Glu Met
305                 310                 315                 320

Gly Thr Val Tyr Ser Thr Leu Gly Ser Arg Leu Asp Val Val Glu Met
                325                 330                 335

Met Asp Gly Leu Met Gln Gly Ala Asp Arg Asp Leu Val Lys Val Trp
            340                 345                 350

Gln Lys Gln Asn Glu Tyr Arg Phe Asp Asn Ile Met Val Asn Thr Lys
        355                 360                 365

Thr Val Ala Val Glu Pro Lys Glu Asp Gly Val Tyr Val Thr Phe Glu
    370                 375                 380

Gly Ala Asn Ala Pro Lys Glu Pro Gln Arg Tyr Asp Ala Val Leu Val
385                 390                 395                 400

Ala Ala Gly Arg Ala Pro Asn Gly Lys Leu Ile Ser Ala Glu Lys Ala
                405                 410                 415

Gly Val Ala Val Thr Asp Arg Gly Phe Ile Glu Val Asp Lys Gln Met
            420                 425                 430

Arg Thr Asn Val Pro His Ile Tyr Ala Ile Gly Asp Ile Val Gly Gln
        435                 440                 445

Pro Met Leu Ala His Lys Ala Val His Glu Gly His Val Ala Ala Glu
    450                 455                 460

Asn Cys Ala Gly His Lys Ala Tyr Phe Asp Ala Arg Val Ile Pro Gly
465                 470                 475                 480

Val Ala Tyr Thr Ser Pro Glu Val Ala Trp Val Gly Glu Thr Glu Leu
                485                 490                 495

Ser Ala Lys Ala Ser Gly Arg Lys Ile Thr Lys Ala Asn Phe Pro Trp
            500                 505                 510

Ala Ala Ser Gly Arg Ala Ile Ala Asn Gly Cys Asp Lys Pro Phe Thr
        515                 520                 525

Lys Leu Ile Phe Asp Ala Glu Thr Gly Arg Ile Ile Gly Gly Gly Ile
    530                 535                 540

Val Gly Pro Asn Gly Gly Asp Met Ile Gly Glu Val Cys Leu Ala Ile
545                 550                 555                 560

Glu Met Gly Cys Asp Ala Ala Asp Ile Gly Lys Thr Ile His Pro His
                565                 570                 575

Pro Gly Glu Ser Ile Gly Met Ala Ala Glu Val Ala Leu Gly Thr Cys
            580                 585                 590

Thr Asp Leu Pro Pro Gln Lys Lys Lys Gly Ser Arg Leu Arg Met Asp
        595                 600                 605

Lys Leu Gln Leu Lys Gly Met Ser Tyr Ser Met Cys Thr Gly Lys Phe
    610                 615                 620

Lys Ile Val Lys Glu Ile Ala Glu Thr Gln His Gly Thr Ile Val Ile
625                 630                 635                 640

Arg Val Gln Tyr Glu Gly Asp Gly Ser Pro Cys Lys Ile Pro Phe Glu
                645                 650                 655

Ile Met Asp Leu Glu Lys Arg His Val Leu Gly Arg Leu Ile Thr Val
            660                 665                 670
```

-continued

```
Asn Pro Ile Val Thr Glu Lys Asp Ser Pro Val Asn Ile Glu Ala Glu
        675                 680                 685

Pro Pro Phe Gly Asp Ser Tyr Ile Ile Ile Gly Val Glu Pro Gly Gln
    690                 695                 700

Leu Lys Leu Asn Trp Phe Lys Lys Gly Ser Ser Ile Gly Gln Met Phe
705                 710                 715                 720

Glu Thr Thr Met Arg Gly Ala Lys Arg Met Ala Ile Leu Gly Asp Thr
                725                 730                 735

Ala Trp Asp Phe Gly Ser Leu Gly Gly
            740                 745
```

<210> SEQ ID NO 32
<211> LENGTH: 429
<212> TYPE: DNA
<213> ORGANISM: Escherichia coli
<220> FEATURE:
<221> NAME/KEY: gene
<222> LOCATION: (1)..(429)
<223> OTHER INFORMATION: Nucleotidic sequence coding for the aminoacids 286 to 426 of the DEN-1 envelope protein

<400> SEQUENCE: 32

```
agactaaaaa tggataaact gactttaaaa ggggtatcat atgtaatgtg cacagggtca     60

ttcaagttag agaaggaagt ggctgagacc cagcatggaa ctgttctagt gcaggttaaa    120

tacgaaggaa cagatgcacc atgcaagatc cccttctcgt cccaagatga gaaaggagta    180

acccagaatg ggagattgat aacagccaac cccatagtca ttgacaaaga aaaaccagtc    240

aacattgaag cggagccacc ttttggtgag agctatattg tggtaggagc aggtgaaaaa    300

gctttgaaac taagctggtt caagaaggga agcagtatag ggaaaatgtt tgaagcaact    360

gcccgtggag cacgaaggat ggccatcctg ggagacaccg catgggactt cggttctata    420

ggagggtaa                                                            429
```

<210> SEQ ID NO 33
<211> LENGTH: 615
<212> TYPE: DNA
<213> ORGANISM: Escherichia coli
<220> FEATURE:
<221> NAME/KEY: gene
<222> LOCATION: (1)..(615)
<223> OTHER INFORMATION: Nucleotidic sequence coding for the quimeric protein in the plasmid pLH1

<400> SEQUENCE: 33

```
atgggccacc accaccacca ccacgccatg gtagataaaa gaatggcttt agttgaattg     60

aaagtgcccg acattggcgg aacagaaaat gtagatatta tcgcggttga agtaaacgtg    120

ggcgacacta ttgctgtgga cgataccctg attactttgg atctagattt ggatctagac    180

aggctcaaaa tggataaact gactttaaaa ggggtatcat atgtaatgtg cacagggtca    240

ttcaagttag agaaggaagt ggctgagacc cagcatggaa ctgttctagt gcaggttaaa    300

tacgaaggaa cagatgcacc atgcaagatc cccttctcgt cccaagatga gaaaggagta    360

acccagaatg ggagattgat aacagccaac cccatagtca ttgacaaaga aaaaccagtc    420

aacattgaag cggagccacc ttttggtgag agctatattg tggtaggagc aggtgaaaaa    480

gctttgaaac taagctggtt caagaaggga agcagtatag ggaaaatgtt tgaagcaact    540

gcccgtggag cacgaaggat ggccatcctg ggagacaccg catgggactt cggttctatt    600

ggcgggtaag gatcc                                                     615
```

<210> SEQ ID NO 34
<211> LENGTH: 174
<212> TYPE: PRT
<213> ORGANISM: Escherichia coli
<220> FEATURE:
<221> NAME/KEY: CHAIN
<222> LOCATION: (1)..(174)
<223> OTHER INFORMATION: Aminoacidic sequence of the PLH1

<400> SEQUENCE: 34

```
His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
         35                  40                  45

Thr Leu Asp Leu Asp Phe Lys Leu Glu Lys Glu Val Ala Glu Thr Gln
     50                  55                  60

His Gly Thr Val Leu Val Gln Val Lys Tyr Gln Gly Thr Asp Ala Pro
 65                  70                  75                  80

Cys Lys Ile Pro Phe Ser Thr Gln Asp Glu Lys Gly Val Thr Gln Asn
                 85                  90                  95

Arg Leu Ile Thr Ala Asn Pro Ile Val Thr Asp Lys Glu Lys Pro Val
            100                 105                 110

Asn Ile Glu Thr Glu Pro Pro Phe Gly Glu Ser Tyr Ile Val Val Gly
        115                 120                 125

Ala Gly Glu Lys Ala Leu Lys Gln Cys Trp Phe Lys Lys Gly Ser Ser
    130                 135                 140

Ile Gly Lys Met Phe Glu Ala Thr Ala Arg Gly Ala Arg Arg Met Ala
145                 150                 155                 160

Ile Leu Gly Asp Thr Ala Trp Asp Phe Gly Ser Ile Gly Gly
                165                 170
```

<210> SEQ ID NO 35
<211> LENGTH: 2253
<212> TYPE: DNA
<213> ORGANISM: Escherichia coli
<220> FEATURE:
<221> NAME/KEY: gene
<222> LOCATION: (1)..(2253)
<223> OTHER INFORMATION: Nucleotidic sequence coding for the quimeric
      protein in the plasmid pLH2

<400> SEQUENCE: 35

```
atgggccacc accaccacca ccacgccatg gtagataaaa gaatggcttt agttgaattg      60

aaagtgcccg acattggcgg aacagaaaat gtagatatta tcgcggttga agtaaacgtg     120

ggcgacacta ttgctgtgga cgataccctg attactttgg atctagattt ggatctagac     180

aggctcaaaa tggataaact gactttaaaa ggggtatcat atgtaatgtg cacagggtca     240

ttcaagttag agaaggaagt ggctgagacc cagcatggaa ctgttctagt gcaggttaaa     300

tacgaaggaa cagatgcacc atgcaagatc cccttctcgt cccaagatga gaaaggagta     360

acccagaatg ggagattgat aacagccaac cccatagtca ttgacaaaga aaaaccagtc     420

aacattgaag cggagccacc ttttggtgag agctatattg tggtaggagc aggtgaaaaa     480

gctttgaaac taagctggtt caagaaggga agcagtatag ggaaaatgtt tgaagcaact     540

gcccgtggag cacgaaggat ggccatcctg ggagacaccg catgggactt cggatctata     600
```

```
ggaggggtga attcgatgaa ttcgatggac gtacctgctg aagttgcagg cgtagtcaaa    660

gaagttaaag ttaaagtcgg cgacaaaatc tctgaaggtg gtttgattgt cgtcgttgaa    720

gctgaaggca cggcagccgc tcctaaagcc gaagcggctg ccgccccggc gcaagaagcc    780

cctaaagctg ccgctcctgc tccgcaagcc gcgcaattcg gcggttctgc cgatgccgag    840

tacgacgtgg tcgtattggg tggcggtccc ggcggttact ccgctgcatt tgccgctgcc    900

gatgaaggct tgaaagtcgc catcgtcgaa cgttacaaaa ctttgggcgg cgtttgcctg    960

aacgtcggct gtatcccttc caaagccttg ttgcacaatg ccgccgttat cgacgaagtg   1020

cgccacttgg ctgccaacgg tatcaaatac cccgagccgg aactcgacat cgatatgctt   1080

cgcgcctaca aagacggcgt agtttcccgc ctcacgggcg gtttggcagg tatggcgaaa   1140

agccgtaaag tggacgttat ccaaggcgac gggcaattct tagatccgca ccacttggaa   1200

gtgtcgctga ctgccggcga cgcgtacgaa caggcagccc ctaccggcga gaaaaaaatc   1260

gttgccttca aaaactgtat cattgcagca ggcagccgcg taaccaaact gcctttcatt   1320

cctgaagatc cgcgcatcat cgattccagc ggcgcattgg ctctgaaaga agtaccgggc   1380

aaactgctga ttatcggcgg cggcattatc ggcctcgaga tgggtacggt ttacagcacg   1440

ctgggttcgc gtttggatgt ggttgaaatg atggacggcc tgatgcaagg cgcagaccgc   1500

gatttggtaa aagtatggca aaaacaaaac gaataccgtt ttgacaacat tatggtcaac   1560

accaaaaccg ttgcagttga gccgaaagaa gacggcgttt acgttacctt tgaaggcgcg   1620

aacgcgccta aagagccgca acgctacgat gccgtattgg ttgccgccgg ccgcgcgccc   1680

aacggcaaac tcatcagcgc ggaaaaagca ggcgttgccg taaccgatcg cggcttcatc   1740

gaagtggaca aacaaatgcg taccaatgtg ccgcacatct acgccatcgg cgacatcgtc   1800

ggtcagccga tgttggcgca caaagccgtt cacgaaggcc acgttgccgc cgaaaactgc   1860

gccggccaca aagcctactt cgacgcacgc gtgattccgg gcgttgccta cacttccccc   1920

gaagtggcgt gggtgggcga aaccgaactg tccgccaaag cctccggccg caaaatcacc   1980

aaagccaact tcccgtgggc ggcttccggc cgtgcgattg ccaacggttg cgacaagccg   2040

tttaccaagc tgatttttga tgccgaaacc ggccgcatca tcggcggcgg cattgtcggt   2100

ccgaacggtg gcgatatgat cggcgaagtc tgccttgcca tcgaaatggg ctgcgacgcg   2160

gcagacatcg gcaaaaccat ccacccgcac ccgggcgaat ccatcggtat ggcggcggaa   2220

gtggcattgg gtacttgtac cgacaaaaaa aaa                                2253
```

<210> SEQ ID NO 36
<211> LENGTH: 727
<212> TYPE: PRT
<213> ORGANISM: Escherichia coli
<220> FEATURE:
<221> NAME/KEY: CHAIN
<222> LOCATION: (1)..(727)
<223> OTHER INFORMATION: Aminoacidic sequence of the PLH2

<400> SEQUENCE: 36

```
His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
         35                  40                  45

Thr Leu Asp Leu Asp Phe Lys Leu Glu Lys Glu Val Ala Glu Thr Gln
     50                  55                  60
```

-continued

```
His Gly Thr Val Leu Val Gln Val Lys Tyr Gln Gly Thr Asp Ala Pro
 65                  70                  75                  80

Cys Lys Ile Pro Phe Ser Thr Gln Asp Glu Lys Gly Val Thr Gln Asn
                 85                  90                  95

Arg Leu Ile Thr Ala Asn Pro Ile Val Thr Asp Lys Glu Lys Pro Val
            100                 105                 110

Asn Ile Glu Thr Glu Pro Pro Phe Gly Glu Ser Tyr Ile Val Val Gly
        115                 120                 125

Ala Gly Glu Lys Ala Leu Lys Gln Cys Trp Phe Lys Lys Gly Ser Ser
    130                 135                 140

Ile Gly Lys Met Phe Glu Ala Thr Ala Arg Gly Ala Arg Arg Met Ala
145                 150                 155                 160

Ile Leu Gly Asp Thr Ala Trp Asp Phe Gly Ser Ile Gly Gly Val Asn
                165                 170                 175

Ser Met Asn Ser Met Asp Val Pro Ala Glu Val Ala Gly Val Val Lys
            180                 185                 190

Glu Val Lys Val Lys Val Gly Asp Lys Ile Ser Glu Gly Gly Leu Ile
        195                 200                 205

Val Val Val Glu Ala Glu Gly Thr Ala Ala Ala Pro Lys Ala Glu Ala
    210                 215                 220

Ala Ala Ala Pro Ala Gln Glu Ala Pro Lys Ala Ala Ala Pro Ala Pro
225                 230                 235                 240

Gln Ala Ala Gln Phe Gly Gly Ser Ala Asp Ala Glu Tyr Asp Val Val
                245                 250                 255

Val Leu Gly Gly Gly Pro Gly Gly Tyr Ser Ala Ala Phe Ala Ala Ala
            260                 265                 270

Asp Glu Gly Leu Lys Val Ala Ile Val Glu Arg Tyr Lys Thr Leu Gly
        275                 280                 285

Gly Val Cys Leu Asn Val Gly Cys Ile Pro Ser Lys Ala Leu Leu His
    290                 295                 300

Asn Ala Ala Val Ile Asp Glu Val Arg His Leu Ala Ala Asn Gly Ile
305                 310                 315                 320

Lys Tyr Pro Glu Pro Glu Leu Asp Ile Asp Met Leu Arg Ala Tyr Lys
                325                 330                 335

Asp Gly Val Val Ser Arg Leu Thr Gly Gly Leu Ala Gly Met Ala Lys
            340                 345                 350

Ser Arg Lys Val Asp Val Ile Gln Gly Asp Gly Gln Phe Leu Asp Pro
        355                 360                 365

His His Leu Glu Val Ser Leu Thr Ala Gly Asp Ala Tyr Glu Gln Ala
    370                 375                 380

Ala Pro Thr Gly Glu Lys Lys Ile Val Ala Phe Lys Asn Cys Ile Ile
385                 390                 395                 400

Ala Ala Gly Ser Arg Val Thr Lys Leu Pro Phe Ile Pro Glu Asp Pro
                405                 410                 415

Arg Ile Ile Asp Ser Ser Gly Ala Leu Ala Leu Lys Glu Val Pro Gly
            420                 425                 430

Lys Leu Leu Ile Ile Gly Gly Gly Ile Ile Gly Leu Glu Met Gly Thr
        435                 440                 445

Val Tyr Ser Thr Leu Gly Ser Arg Leu Asp Val Val Glu Met Met Asp
    450                 455                 460

Gly Leu Met Gln Gly Ala Asp Arg Asp Leu Val Lys Val Trp Gln Lys
465                 470                 475                 480
```

```
Gln Asn Glu Tyr Arg Phe Asp Asn Ile Met Val Asn Thr Lys Thr Val
                485                 490                 495

Ala Val Glu Pro Lys Glu Asp Gly Val Tyr Val Thr Phe Glu Gly Ala
            500                 505                 510

Asn Ala Pro Lys Glu Pro Gln Arg Tyr Asp Ala Val Leu Val Ala Ala
        515                 520                 525

Gly Arg Ala Pro Asn Gly Lys Leu Ile Ser Ala Glu Lys Ala Gly Val
    530                 535                 540

Ala Val Thr Asp Arg Gly Phe Ile Glu Val Asp Lys Gln Met Arg Thr
545                 550                 555                 560

Asn Val Pro His Ile Tyr Ala Ile Gly Asp Ile Val Gly Gln Pro Met
                565                 570                 575

Leu Ala His Lys Ala Val His Glu Gly His Val Ala Ala Glu Asn Cys
            580                 585                 590

Ala Gly His Lys Ala Tyr Phe Asp Ala Arg Val Ile Pro Gly Val Ala
        595                 600                 605

Tyr Thr Ser Pro Glu Val Ala Trp Val Gly Glu Thr Glu Leu Ser Ala
    610                 615                 620

Lys Ala Ser Gly Arg Lys Ile Thr Lys Ala Asn Phe Pro Trp Ala Ala
625                 630                 635                 640

Ser Gly Arg Ala Ile Ala Asn Gly Cys Asp Lys Pro Phe Thr Lys Leu
                645                 650                 655

Ile Phe Asp Ala Glu Thr Gly Arg Ile Ile Gly Gly Gly Ile Val Gly
            660                 665                 670

Pro Asn Gly Gly Asp Met Ile Gly Glu Val Cys Leu Ala Ile Glu Met
        675                 680                 685

Gly Cys Asp Ala Ala Asp Ile Gly Lys Thr Ile His Pro His Pro Gly
    690                 695                 700

Glu Ser Ile Gly Met Ala Ala Glu Val Ala Leu Gly Thr Cys Thr Asp
705                 710                 715                 720

Leu Pro Pro Gln Lys Lys Lys
                725
```

<210> SEQ ID NO 37
<211> LENGTH: 2250
<212> TYPE: DNA
<213> ORGANISM: Escherichia coli
<220> FEATURE:
<221> NAME/KEY: gene
<222> LOCATION: (1)..(2250)
<223> OTHER INFORMATION: Nucleotidic sequence coding for the quimeric protein in the plasmid pLH3

<400> SEQUENCE: 37

```
atgggccacc accaccacca ccacgccatg gtagataaaa gaatggcttt agttgaattg      60

aaagtgcccg acattggcgg acacgaaaat gtagatatta tcgcggttga agtaaacgtg     120

ggcgacacta ttgctgtgga cgataccctg attactttgg atctagaaat ggacgtacct     180

gctgaagttg caggcgtagt caaagaagtt aaagttaaag tcggcgacaa aatctctgaa     240

ggtggtttga ttgtcgtcgt tgaagctgaa ggcacggcag ccgctcctaa agccgaagcg     300

gctgccgccc cggcgcaaga agcccctaaa gctgccgctc ctgctccgca agccgcgcaa     360

ttcggcggtt ctgccgatgc cgagtacgac gtggtcgtat tgggtggcgg tcccggcggt     420

tactccgctg catttgccgc tgccgatgaa ggcttgaaag tcgccatcgt cgaacgttac     480

aaaactttgg gcggcgtttg cctgaacgtc ggctgtatcc cttccaaagc cttgttgcac     540
```

-continued

```
aatgccgccg ttatcgacga agtgcgccac ttggctgcca acggtatcaa ataccccgag    600

ccggaactcg acatcgatat gcttcgcgcc tacaaagacg gcgtagtttc ccgcctcacg    660

ggcggtttgg caggtatggc gaaaagccgt aaagtggacg ttatccaagg cgacgggcaa    720

ttcttagatc cgcaccactt ggaagtgtcg ctgactgccg gcgacgcgta cgaacaggca    780

gcccctaccg gcgagaaaaa aatcgttgcc ttcaaaaact gtatcattgc agcaggcagc    840

cgcgtaacca aactgccttt cattcctgaa gatccgcgca tcatcgattc cagcggcgca    900

ttggctctga aagaagtacc gggcaaactg ctgattatcg gcggcggcat tatcggcctc    960

gagatgggta cggtttacag cacgctgggt tcgcgtttgg atgtggttga aatgatggac   1020

ggcctgatgc aaggcgcaga ccgcgatttg gtaaaagtat ggcaaaaaca aaacgaatac   1080

cgttttgaca acattatggt caacaccaaa accgttgcag ttgagccgaa agaagacggc   1140

gtttacgtta cctttgaagg cgcgaacgcg cctaaagagc cgcaacgcta cgatgccgta   1200

ttggttgccg ccggccgcgc gcccaacggc aaactcatca gcgcggaaaa agcaggcgtt   1260

gccgtaaccg atcgcggctt catcgaagtg gacaaacaaa tgcgtaccaa tgtgccgcac   1320

atctacgcca tcggcgacat cgtcggtcag ccgatgttgg cgcacaaagc cgttcacgaa   1380

ggccacgttg ccgccgaaaa ctgcgccggc cacaaagcct acttcgacgc acgcgtgatt   1440

ccgggcgttg cctacacttc ccccgaagtg gcgtgggtgg gcgaaaccga actgtccgcc   1500

aaagcctccg gccgcaaaat caccaaagcc aacttcccgt gggcggcttc cggccgtgcg   1560

attgccaacg gttgcgacaa gccgtttacc aagctgattt ttgatgccga aaccggccgc   1620

atcatcggcg gcggcattgt cggtccgaac ggtggcgata tgatcggcga agtctgcctt   1680

gccatcgaaa tgggctgcga cgcggcagac atcggcaaaa ccatccaccc gcacccgacc   1740

ttgggcgaat ccatcggtat ggcggcggaa gtggcattgg gtacttgtac cgacctgcct   1800

ccgcaaaaga aaaaaggatc cagactaaaa atggataaac tgactttaaa aggggtatca   1860

tatgtaatgt gcacagggtc attcaagtta gagaaggaag tggctgagac ccagcatgga   1920

actgttctag tgcaggttaa atacgaagga acagatgcac catgcaagat ccccttctcg   1980

tcccaagatg agaaaggagt aacccagaat gggagattga taacagccaa ccccatagtc   2040

attgacaaag aaaaaccagt caacattgaa gcggagccac cttttggtga gagctatatt   2100

gtggtaggag caggtgaaaa agctttgaaa ctaagctggt tcaagaaggg aagcagtata   2160

gggaaaatgt ttgaagcaac tgcccgtgga gcacgaagga tggccatcct gggagacacc   2220

gcatgggact tcggttctat aggtgggtaa                                    2250
```

<210> SEQ ID NO 38
<211> LENGTH: 724
<212> TYPE: PRT
<213> ORGANISM: Escherichia coli
<220> FEATURE:
<221> NAME/KEY: CHAIN
<222> LOCATION: (1)..(724)
<223> OTHER INFORMATION: Aminoacidic sequence of the PLH3

<400> SEQUENCE: 38

```
His His His His His His Met Val Asp Lys Arg Met Ala Leu Val Glu
1               5                   10                  15

Leu Lys Val Pro Asp Ile Gly Gly His Glu Asn Val Asp Ile Ile Ala
            20                  25                  30

Val Glu Val Asn Val Gly Asp Thr Ile Ala Val Asp Asp Thr Leu Ile
        35                  40                  45
```

-continued

```
Thr Leu Asp Met Asn Ser Met Asp Val Pro Ala Glu Val Ala Gly Val
    50                  55                  60

Val Lys Glu Val Lys Val Lys Val Gly Asp Lys Ile Ser Glu Gly Gly
 65                 70                  75                  80

Leu Ile Val Val Val Glu Ala Glu Gly Thr Ala Ala Ala Pro Lys Ala
                85                  90                  95

Glu Ala Ala Ala Ala Pro Ala Gln Glu Ala Pro Lys Ala Ala Ala Pro
            100                 105                 110

Ala Pro Gln Ala Ala Gln Phe Gly Gly Ser Ala Asp Ala Glu Tyr Asp
        115                 120                 125

Val Val Val Leu Gly Gly Gly Pro Gly Gly Tyr Ser Ala Ala Phe Ala
    130                 135                 140

Ala Ala Asp Glu Gly Leu Lys Val Ala Ile Val Glu Arg Tyr Lys Thr
145                 150                 155                 160

Leu Gly Gly Val Cys Leu Asn Val Gly Cys Ile Pro Ser Lys Ala Leu
                165                 170                 175

Leu His Asn Ala Ala Val Ile Asp Glu Val Arg His Leu Ala Ala Asn
            180                 185                 190

Gly Ile Lys Tyr Pro Glu Pro Glu Leu Asp Ile Asp Met Leu Arg Ala
        195                 200                 205

Tyr Lys Asp Gly Val Val Ser Arg Leu Thr Gly Gly Leu Ala Gly Met
    210                 215                 220

Ala Lys Ser Arg Lys Val Asp Val Ile Gln Gly Asp Gly Gln Phe Leu
225                 230                 235                 240

Asp Pro His His Leu Glu Val Ser Leu Thr Ala Gly Asp Ala Tyr Glu
                245                 250                 255

Gln Ala Ala Pro Thr Gly Glu Lys Lys Ile Val Ala Phe Lys Asn Cys
            260                 265                 270

Ile Ile Ala Ala Gly Ser Arg Val Thr Lys Leu Pro Phe Ile Pro Glu
        275                 280                 285

Asp Pro Arg Ile Ile Asp Ser Ser Gly Ala Leu Ala Leu Lys Glu Val
    290                 295                 300

Pro Gly Lys Leu Leu Ile Ile Gly Gly Gly Ile Ile Gly Leu Glu Met
305                 310                 315                 320

Gly Thr Val Tyr Ser Thr Leu Gly Ser Arg Leu Asp Val Val Glu Met
                325                 330                 335

Met Asp Gly Leu Met Gln Gly Ala Asp Arg Asp Leu Val Lys Val Trp
            340                 345                 350

Gln Lys Gln Asn Glu Tyr Arg Phe Asp Asn Ile Met Val Asn Thr Lys
        355                 360                 365

Thr Val Ala Val Glu Pro Lys Glu Asp Gly Val Tyr Val Thr Phe Glu
    370                 375                 380

Gly Ala Asn Ala Pro Lys Glu Pro Gln Arg Tyr Asp Ala Val Leu Val
385                 390                 395                 400

Ala Ala Gly Arg Ala Pro Asn Gly Lys Leu Ile Ser Ala Glu Lys Ala
                405                 410                 415

Gly Val Ala Val Thr Asp Arg Gly Phe Ile Glu Val Asp Lys Gln Met
            420                 425                 430

Arg Thr Asn Val Pro His Ile Tyr Ala Ile Gly Asp Ile Val Gly Gln
        435                 440                 445

Pro Met Leu Ala His Lys Ala Val His Glu Gly His Val Ala Ala Glu
    450                 455                 460

Asn Cys Ala Gly His Lys Ala Tyr Phe Asp Ala Arg Val Ile Pro Gly
```

-continued

```
465                 470                 475                 480

Val Ala Tyr Thr Ser Pro Glu Val Ala Trp Val Gly Glu Thr Glu Leu
                485                 490                 495

Ser Ala Lys Ala Ser Gly Arg Lys Ile Thr Lys Ala Asn Phe Pro Trp
            500                 505                 510

Ala Ala Ser Gly Arg Ala Ile Ala Asn Gly Cys Asp Lys Pro Phe Thr
        515                 520                 525

Lys Leu Ile Phe Asp Ala Glu Thr Gly Arg Ile Ile Gly Gly Gly Ile
    530                 535                 540

Val Gly Pro Asn Gly Gly Asp Met Ile Gly Glu Val Cys Leu Ala Ile
545                 550                 555                 560

Glu Met Gly Cys Asp Ala Ala Asp Ile Gly Lys Thr Ile His Pro His
                565                 570                 575

Pro Gly Glu Ser Ile Gly Met Ala Ala Glu Val Ala Leu Gly Thr Cys
            580                 585                 590

Thr Asp Leu Pro Pro Gln Lys Lys Lys Gly Ser Phe Lys Leu Glu Lys
        595                 600                 605

Glu Val Ala Glu Thr Gln His Gly Thr Val Leu Val Gln Val Lys Tyr
    610                 615                 620

Gln Gly Thr Asp Ala Pro Cys Lys Ile Pro Phe Ser Thr Gln Asp Glu
625                 630                 635                 640

Lys Gly Val Thr Gln Asn Arg Leu Ile Thr Ala Asn Pro Ile Val Thr
                645                 650                 655

Asp Lys Glu Lys Pro Val Asn Ile Glu Thr Glu Pro Pro Phe Gly Glu
            660                 665                 670

Ser Tyr Ile Val Val Gly Ala Gly Glu Lys Ala Leu Lys Gln Cys Trp
        675                 680                 685

Phe Lys Lys Gly Ser Ser Ile Gly Lys Met Phe Glu Ala Thr Ala Arg
    690                 695                 700

Gly Ala Arg Arg Met Ala Ile Leu Gly Asp Thr Ala Trp Asp Phe Gly
705                 710                 715                 720

Ser Ile Gly Gly
```

<210> SEQ ID NO 39
<211> LENGTH: 426
<212> TYPE: DNA
<213> ORGANISM: Escherichia coli
<220> FEATURE:
<221> NAME/KEY: gene
<222> LOCATION: (1)..(426)
<223> OTHER INFORMATION: Nucleotidic sequence coding for the aminoacids 286 to 426 of the DEN-3 envelope protein

<400> SEQUENCE: 39

```
agactcaaga tggacaaatt gaaactcaag gggatgagct atgcaatgtg cttgaatacc     60

tttgtgttga agaaagaagt ctccgaaacg cagcatggga caatactcat taaggttgag    120

tacaaagggg aagatgcacc ctgcaagatt cctttctcca cggaggatgg acaagggaaa    180

gctcacaatg gcagactgat cacagccaat ccagtggtga ccaagaagga ggagcctgtc    240

aacattgagg ctgaacctcc ttttggggaa agtaatatag taattggaat tggagacaaa    300

gccctgaaaa tcaactggta caggaaggga agctcgattg ggaagatgtt cgaggccact    360

gccagaggtg caaggcgcat ggccatcttg ggagacacag cctgggactt tggatcagtg    420

ggtggt                                                               426
```

```
<210> SEQ ID NO 40
<211> LENGTH: 615
<212> TYPE: DNA
<213> ORGANISM: Escherichia coli
<220> FEATURE:
<221> NAME/KEY: gene
<222> LOCATION: (1)..(615)
<223> OTHER INFORMATION: Nucleotidic sequence coding for the quimeric
      protein in the plasmid pAZ1

<400> SEQUENCE: 40

atgggccacc accaccacca ccacgccatg gtagataaaa gaatggcttt agttgaattg     60

aaagtgcccg acattggcgg aacagaaaat gtagatatta tcgcggttga agtaaacgtg    120

ggcgacacta ttgctgtgga cgataccctg attactttgg atctagattt ggatctagat    180

agactcaaga tggacaaatt gaaactcaag ggatgagct atgcaatgtg cttgaatacc    240

tttgtgttga agaaagaagt ctccgaaacg cagcatggga caatactcat taaggttgag    300

tacaaagggg aagatgcacc ctgcaagatt cctttctcca cggaggatgg acaagggaaa    360

gctcacaatg gcagactgat cacagccaat ccagtggtga ccaagaagga ggagcctgtc    420

aacattgagg ctgaacctcc ttttggggaa agtaatatag taattggaat tggagacaaa    480

gccctgaaaa tcaactggta caggaaggga agctcgattg ggaagatgtt cgaggccact    540

gccagaggtg caaggcgcat ggccatcttg ggagacacag cctgggactt tggttcagtg    600

ggtggttaag gatcc                                                     615


<210> SEQ ID NO 41
<211> LENGTH: 194
<212> TYPE: PRT
<213> ORGANISM: Escherichia coli
<220> FEATURE:
<221> NAME/KEY: CHAIN
<222> LOCATION: (1)..(194)
<223> OTHER INFORMATION: Aminoacidic sequence of the PAZ1

<400> SEQUENCE: 41

His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
         35                  40                  45

Thr Leu Asp Leu Asp Arg Leu Lys Met Asp Lys Leu Lys Leu Lys Gly
     50                  55                  60

Met Ser Tyr Ala Met Cys Leu Asn Thr Phe Val Leu Lys Lys Glu Val
 65                  70                  75                  80

Ser Glu Thr His Gly Thr Ile Leu Ile Lys Val Glu Tyr Lys Gly Glu
                 85                  90                  95

Asp Ala Pro Cys Lys Ile Pro Phe Ser Thr Glu Asp Gly Gln Gly Lys
            100                 105                 110

Ala His Asn Gly Arg Leu Ile Thr Ala Asn Pro Val Val Thr Lys Lys
        115                 120                 125

Glu Glu Pro Val Asn Ile Glu Ala Glu Pro Pro Phe Gly Glu Ser Asn
    130                 135                 140

Ile Val Ile Gly Ile Gly Asp Lys Ala Leu Lys Ile Asn Trp Tyr Arg
145                 150                 155                 160

Lys Gly Ser Ser Ile Gly Lys Met Phe Glu Ala Thr Ala Arg Gly Ala
                165                 170                 175
```

-continued

```
Arg Arg Met Ala Ile Leu Gly Asp Thr Ala Trp Asp Phe Gly Ser Val
            180                 185                 190

Gly Gly


<210> SEQ ID NO 42
<211> LENGTH: 2253
<212> TYPE: DNA
<213> ORGANISM: Escherichia coli
<220> FEATURE:
<221> NAME/KEY: gene
<222> LOCATION: (1)..(2253)
<223> OTHER INFORMATION: Nucleotidic sequence coding for the quimeric
      protein in the plasmid pAZ2

<400> SEQUENCE: 42

atgggccacc accaccacca ccacgccatg gtagataaaa gaatggcttt agttgaattg     60

aaagtgcccg acattggcgg aacagaaaat gtagatatta tcgcggttga agtaaacgtg    120

ggcgacacta ttgctgtgga cgataccctg attactttgg atctagattt ggatctagat    180

agactcaaga tggacaaatt gaaactcaag ggatgagct atgcaatgtg cttgaatacc    240

tttgtgttga agaaagaagt ctccgaaacg cagcatggga caatactcat taaggttgag    300

tacaaagggg aagatgcacc ctgcaagatt cctttctcca cggaggatgg acaagggaaa    360

gctcacaatg gcagactgat cacagccaat ccagtggtga ccaagaagga ggagcctgtc    420

aacattgagg ctgaacctcc ttttggggaa agtaatatag taattggaat tggagacaaa    480

gccctgaaaa tcaactggta caggaaggga agctcgattg ggaagatgtt cgaggccact    540

gccagaggtg caaggcgcat ggccatcttg ggagacacag cctgggactt tggatctgtg    600

ggtggtgtga attcgatgaa ttcgatggac gtacctgctg aagttgcagg cgtagtcaaa    660

gaagttaaag ttaaagtcgg cgacaaaatc tctgaaggtg gtttgattgt cgtcgttgaa    720

gctgaaggca cggcagccgc tcctaaagcc gaagcggctg ccgcccccgc gcaagaagcc    780

cctaaagctg ccgctcctgc tccgcaagcc gcgcaattcg gcggttctgc cgatgccgag    840

tacgacgtgg tcgtattggg tggcggtccc ggcggttact ccgctgcatt tgccgctgcc    900

gatgaaggct tgaaagtcgc catcgtcgaa cgttacaaaa ctttgggcgg cgtttgcctg    960

aacgtcggct gtatcccttc caaagccttg ttgcacaatg ccgccgttat cgacgaagtg   1020

cgccacttgg ctgccaacgg tatcaaatac cccgagccgg aactcgacat cgatatgctt   1080

cgcgcctaca aagacggcgt agtttcccgc ctcacgggcg gtttggcagg tatggcgaaa   1140

agccgtaaag tggacgttat ccaaggcgac gggcaattct tagatccgca ccacttggaa   1200

gtgtcgctga ctgccggcga cgcgtacgaa caggcagccc ctaccggcga gaaaaaaatc   1260

gttgccttca aaaactgtat cattgcagca ggcagccgcg taaccaaact gcctttcatt   1320

cctgaagatc cgcgcatcat cgattccagc ggcgcattgg ctctgaaaga agtaccgggc   1380

aaactgctga ttatcggcgg cggcattatc ggcctcgaga tgggtacggt ttacagcacg   1440

ctgggttcgc gtttggatgt ggttgaaatg atggacggcc tgatgcaagg cgcagaccgc   1500

gatttggtaa aagtatggca aaaacaaaac gaataccgtt ttgacaacat tatggtcaac   1560

accaaaaccg ttgcagttga gccgaaagaa gacggcgttt acgttacctt tgaaggcgcg   1620

aacgcgccta aagagccgca acgctacgat gccgtattgg ttgccgccgg ccgcgcgccc   1680

aacggcaaac tcatcagcgc ggaaaaagca ggcgttgccg taaccgatcg cggcttcatc   1740

gaagtggaca aacaaatgcg taccaatgtg ccgcacatct acgccatcgg cgacatcgtc   1800

ggtcagccga tgttggcgca caaagccgtt cacgaaggcc acgttgccgc cgaaaactgc   1860
```

```
gccggccaca aagcctactt cgacgcacgc gtgattccgg gcgttgccta cacttccccc   1920

gaagtggcgt gggtgggcga aaccgaactg tccgccaaag cctccggccg caaaatcacc   1980

aaagccaact tcccgtgggc ggcttccggc cgtgcgattg ccaacggttg cgacaagccg   2040

tttaccaagc tgatttttga tgccgaaacc ggccgcatca tcggcggcgg cattgtcggt   2100

ccgaacggtg gcgatatgat cggcgaagtc tgccttgcca tcgaaatggg ctgcgacgcg   2160

gcagacatcg gcaaaaccat ccacccgcac ccgggcgaat ccatcggtat ggcggcggaa   2220

gtggcattgg gtacttgtac cgacaaaaaa aaa                                2253
```

<210> SEQ ID NO 43
<211> LENGTH: 747
<212> TYPE: PRT
<213> ORGANISM: Escherichia coli
<220> FEATURE:
<221> NAME/KEY: CHAIN
<222> LOCATION: (1)..(747)
<223> OTHER INFORMATION: Aminoacidic sequence of the PAZ2

<400> SEQUENCE: 43

```
His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
         35                  40                  45

Thr Leu Asp Leu Asp Arg Leu Lys Met Asp Lys Leu Lys Leu Lys Gly
     50                  55                  60

Met Ser Tyr Ala Met Cys Leu Asn Thr Phe Val Leu Lys Lys Glu Val
 65                  70                  75                  80

Ser Glu Thr His Gly Thr Ile Leu Ile Lys Val Glu Tyr Lys Gly Glu
                 85                  90                  95

Asp Ala Pro Cys Lys Ile Pro Phe Ser Thr Glu Asp Gly Gln Gly Lys
            100                 105                 110

Ala His Asn Gly Arg Leu Ile Thr Ala Asn Pro Val Val Thr Lys Lys
        115                 120                 125

Glu Glu Pro Val Asn Ile Glu Ala Glu Pro Pro Phe Gly Glu Ser Asn
    130                 135                 140

Ile Val Ile Gly Ile Gly Asp Lys Ala Leu Lys Ile Asn Trp Tyr Arg
145                 150                 155                 160

Lys Gly Ser Ser Ile Gly Lys Met Phe Glu Ala Thr Ala Arg Gly Ala
                165                 170                 175

Arg Arg Met Ala Ile Leu Gly Asp Thr Ala Trp Asp Phe Gly Ser Val
            180                 185                 190

Gly Gly Val Asn Ser Met Asn Ser Met Asp Val Pro Ala Glu Val Ala
        195                 200                 205

Gly Val Val Lys Glu Val Lys Val Lys Val Gly Asp Lys Ile Ser Glu
    210                 215                 220

Gly Gly Leu Ile Val Val Val Glu Ala Glu Gly Thr Ala Ala Ala Pro
225                 230                 235                 240

Lys Ala Glu Ala Ala Ala Ala Pro Ala Gln Glu Ala Pro Lys Ala Ala
                245                 250                 255

Ala Pro Ala Pro Gln Ala Ala Gln Phe Gly Gly Ser Ala Asp Ala Glu
            260                 265                 270

Tyr Asp Val Val Val Leu Gly Gly Gly Pro Gly Gly Tyr Ser Ala Ala
```

```
        275                 280                 285

Phe Ala Ala Ala Asp Glu Gly Leu Lys Val Ala Ile Val Glu Arg Tyr
    290                 295                 300

Lys Thr Leu Gly Gly Val Cys Leu Asn Val Gly Cys Ile Pro Ser Lys
305                 310                 315                 320

Ala Leu Leu His Asn Ala Ala Val Ile Asp Glu Val Arg His Leu Ala
                325                 330                 335

Ala Asn Gly Ile Lys Tyr Pro Glu Pro Glu Leu Asp Ile Asp Met Leu
            340                 345                 350

Arg Ala Tyr Lys Asp Gly Val Val Ser Arg Leu Thr Gly Gly Leu Ala
        355                 360                 365

Gly Met Ala Lys Ser Arg Lys Val Asp Val Ile Gln Gly Asp Gly Gln
    370                 375                 380

Phe Leu Asp Pro His His Leu Glu Val Ser Leu Thr Ala Gly Asp Ala
385                 390                 395                 400

Tyr Glu Gln Ala Ala Pro Thr Gly Glu Lys Lys Ile Val Ala Phe Lys
                405                 410                 415

Asn Cys Ile Ile Ala Ala Gly Ser Arg Val Thr Lys Leu Pro Phe Ile
            420                 425                 430

Pro Glu Asp Pro Arg Ile Ile Asp Ser Ser Gly Ala Leu Ala Leu Lys
        435                 440                 445

Glu Val Pro Gly Lys Leu Leu Ile Ile Gly Gly Gly Ile Ile Gly Leu
    450                 455                 460

Glu Met Gly Thr Val Tyr Ser Thr Leu Gly Ser Arg Leu Asp Val Val
465                 470                 475                 480

Glu Met Met Asp Gly Leu Met Gln Gly Ala Asp Arg Asp Leu Val Lys
                485                 490                 495

Val Trp Gln Lys Gln Asn Glu Tyr Arg Phe Asp Asn Ile Met Val Asn
            500                 505                 510

Thr Lys Thr Val Ala Val Glu Pro Lys Glu Asp Gly Val Tyr Val Thr
        515                 520                 525

Phe Glu Gly Ala Asn Ala Pro Lys Glu Pro Gln Arg Tyr Asp Ala Val
    530                 535                 540

Leu Val Ala Ala Gly Arg Ala Pro Asn Gly Lys Leu Ile Ser Ala Glu
545                 550                 555                 560

Lys Ala Gly Val Ala Val Thr Asp Arg Gly Phe Ile Glu Val Asp Lys
                565                 570                 575

Gln Met Arg Thr Asn Val Pro His Ile Tyr Ala Ile Gly Asp Ile Val
            580                 585                 590

Gly Gln Pro Met Leu Ala His Lys Ala Val His Glu Gly His Val Ala
        595                 600                 605

Ala Glu Asn Cys Ala Gly His Lys Ala Tyr Phe Asp Ala Arg Val Ile
    610                 615                 620

Pro Gly Val Ala Tyr Thr Ser Pro Glu Val Ala Trp Val Gly Glu Thr
625                 630                 635                 640

Glu Leu Ser Ala Lys Ala Ser Gly Arg Lys Ile Thr Lys Ala Asn Phe
                645                 650                 655

Pro Trp Ala Ala Ser Gly Arg Ala Ile Ala Asn Gly Cys Asp Lys Pro
            660                 665                 670

Phe Thr Lys Leu Ile Phe Asp Ala Glu Thr Gly Arg Ile Ile Gly Gly
        675                 680                 685

Gly Ile Val Gly Pro Asn Gly Gly Asp Met Ile Gly Glu Val Cys Leu
    690                 695                 700
```

```
Ala Ile Glu Met Gly Cys Asp Ala Ala Asp Ile Gly Lys Thr Ile His
705                 710                 715                 720

Pro His Pro Gly Glu Ser Ile Gly Met Ala Ala Glu Val Ala Leu Gly
                725                 730                 735

Thr Cys Thr Asp Leu Pro Pro Gln Lys Lys Lys
            740                 745


<210> SEQ ID NO 44
<211> LENGTH: 2256
<212> TYPE: DNA
<213> ORGANISM: Escherichia coli
<220> FEATURE:
<221> NAME/KEY: gene
<222> LOCATION: (1)..(2256)
<223> OTHER INFORMATION: Nucleotidic sequence coding for the quimeric
      protein in the plasmid pAZ3

<400> SEQUENCE: 44

atgggccacc accaccacca ccacgccatg gtagataaaa gaatggcttt agttgaattg     60

aaagtgcccg acattggcgg acacgaaaat gtagatatta tcgcggttga agtaaacgtg    120

ggcgacacta ttgctgtgga cgataccctg attactttgg atctagaaat ggacgtacct    180

gctgaagttg caggcgtagt caaagaagtt aaagttaaag tcggcgacaa aatctctgaa    240

ggtggtttga ttgtcgtcgt tgaagctgaa ggcacggcag ccgctcctaa agccgaagcg    300

gctgccgccc cggcgcaaga agcccctaaa gctgccgctc ctgctccgca agccgcgcaa    360

ttcggcggtt ctgccgatgc cgagtacgac gtggtcgtat tgggtggcgg tcccggcggt    420

tactccgctg catttgccgc tgccgatgaa ggcttgaaag tcgccatcgt cgaacgttac    480

aaaactttgg gcggcgtttg cctgaacgtc ggctgtatcc cttccaaagc cttgttgcac    540

aatgccgccg ttatcgacga agtgcgccac ttggctgcca acggtatcaa ataccccgag    600

ccggaactcg acatcgatat gcttcgcgcc tacaaagacg gcgtagtttc ccgcctcacg    660

ggcggtttgg caggtatggc gaaaagccgt aaagtggacg ttatccaagg cgacgggcaa    720

ttcttagatc cgcaccactt ggaagtgtcg ctgactgccg gcgacgcgta cgaacaggca    780

gcccctaccg gcgagaaaaa aatcgttgcc ttcaaaaact gtatcattgc agcaggcagc    840

cgcgtaacca aactgccttt cattcctgaa gatccgcgca tcatcgattc cagcggcgca    900

ttggctctga aagaagtacc gggcaaactg ctgattatcg gcggcggcat tatcggcctc    960

gagatgggta cggtttacag cacgctgggt tcgcgtttgg atgtggttga aatgatggac   1020

ggcctgatgc aaggcgcaga ccgcgatttg gtaaaagtat ggcaaaaaca aaacgaatac   1080

cgttttgaca acattatggt caacaccaaa accgttgcag ttgagccgaa agaagacggc   1140

gtttacgtta cctttgaagg cgcgaacgcg cctaaagagc cgcaacgcta cgatgccgta   1200

ttggttgccg ccggccgcgc gcccaacggc aaactcatca gcgcggaaaa agcaggcgtt   1260

gccgtaaccg atcgcggctt catcgaagtg gacaaacaaa tgcgtaccaa tgtgccgcac   1320

atctacgcca tcggcgacat cgtcggtcag ccgatgttgg cgcacaaagc cgttcacgaa   1380

ggccacgttg ccgccgaaaa ctgcgccggc cacaaagcct acttcgacgc acgcgtgatt   1440

ccgggcgttg cctacacttc ccccgaagtg gcgtgggtgg gcgaaaccga actgtccgcc   1500

aaagcctccg gccgcaaaat caccaaagcc aacttcccgt gggcggcttc cggccgtgcg   1560

attgccaacg gttgcgacaa gccgtttacc aagctgattt ttgatgccga aaccggccgc   1620

atcatcggcg gcggcattgt cggtccgaac ggtggcgata tgatcggcga agtctgcctt   1680
```

-continued

```
gccatcgaaa tgggctgcga cgcggcagac atcggcaaaa ccatccaccc gcacccgacc   1740

ttgggcgaat ccatcggtat ggcggcggaa gtggcattgg gtacttgtac cgacctgcct   1800

ccgcaaaaga aaaaaggatc cagactcaag atggacaaat tgaaactcaa ggggatgagc   1860

tatgcaatgt gcttgaatac ctttgtgttg aagaaagaag tctccgaaac gcagcatggg   1920

acaatactca ttaaggttga gtacaaaggg gaagatgcac cctgcaagat tcctttctcc   1980

acggaggatg gacaagggaa agctcacaat ggcagactga tcacagccaa tccagtggtg   2040

accaagaagg aggagcctgt caacattgag gctgaacctc cttttgggga aagtaatata   2100

gtaattggaa ttggagacaa agccctgaaa atcaactggt acaggaaggg aagctcgatt   2160

gggaagatgt tcgaggccac tgccagaggt gcaaggcgca tggccatctt gggagacaca   2220

gcctgggact ttggttcagt gggtggttaa ggatcc                              2256
```

<210> SEQ ID NO 45
<211> LENGTH: 744
<212> TYPE: PRT
<213> ORGANISM: Escherichia coli
<220> FEATURE:
<221> NAME/KEY: CHAIN
<222> LOCATION: (1)..(744)
<223> OTHER INFORMATION: Aminoacidic sequence of the PAZ3

<400> SEQUENCE: 45

```
His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
         35                  40                  45

Thr Leu Asp Met Asn Ser Met Asp Val Pro Ala Glu Val Ala Gly Val
     50                  55                  60

Val Lys Glu Val Lys Val Lys Val Gly Asp Lys Ile Ser Glu Gly Gly
 65                  70                  75                  80

Leu Ile Val Val Val Glu Ala Glu Gly Thr Ala Ala Ala Pro Lys Ala
                 85                  90                  95

Glu Ala Ala Ala Ala Pro Ala Gln Glu Ala Pro Lys Ala Ala Ala Pro
            100                 105                 110

Ala Pro Gln Ala Ala Gln Phe Gly Gly Ser Ala Asp Ala Glu Tyr Asp
        115                 120                 125

Val Val Val Leu Gly Gly Gly Pro Gly Gly Tyr Ser Ala Ala Phe Ala
    130                 135                 140

Ala Ala Asp Glu Gly Leu Lys Val Ala Ile Val Glu Arg Tyr Lys Thr
145                 150                 155                 160

Leu Gly Gly Val Cys Leu Asn Val Gly Cys Ile Pro Ser Lys Ala Leu
                165                 170                 175

Leu His Asn Ala Ala Val Ile Asp Glu Val Arg His Leu Ala Ala Asn
            180                 185                 190

Gly Ile Lys Tyr Pro Glu Pro Glu Leu Asp Ile Asp Met Leu Arg Ala
        195                 200                 205

Tyr Lys Asp Gly Val Val Ser Arg Leu Thr Gly Gly Leu Ala Gly Met
    210                 215                 220

Ala Lys Ser Arg Lys Val Asp Val Ile Gln Gly Asp Gly Gln Phe Leu
225                 230                 235                 240

Asp Pro His His Leu Glu Val Ser Leu Thr Ala Gly Asp Ala Tyr Glu
                245                 250                 255
```

-continued

```
Gln Ala Ala Pro Thr Gly Glu Lys Lys Ile Val Ala Phe Lys Asn Cys
            260                 265                 270

Ile Ile Ala Ala Gly Ser Arg Val Thr Lys Leu Pro Phe Ile Pro Glu
        275                 280                 285

Asp Pro Arg Ile Ile Asp Ser Ser Gly Ala Leu Ala Leu Lys Glu Val
    290                 295                 300

Pro Gly Lys Leu Leu Ile Ile Gly Gly Gly Ile Ile Gly Leu Glu Met
305                 310                 315                 320

Gly Thr Val Tyr Ser Thr Leu Gly Ser Arg Leu Asp Val Val Glu Met
                325                 330                 335

Met Asp Gly Leu Met Gln Gly Ala Asp Arg Asp Leu Val Lys Val Trp
            340                 345                 350

Gln Lys Gln Asn Glu Tyr Arg Phe Asp Asn Ile Met Val Asn Thr Lys
        355                 360                 365

Thr Val Ala Val Glu Pro Lys Glu Asp Gly Val Tyr Val Thr Phe Glu
    370                 375                 380

Gly Ala Asn Ala Pro Lys Glu Pro Gln Arg Tyr Asp Ala Val Leu Val
385                 390                 395                 400

Ala Ala Gly Arg Ala Pro Asn Gly Lys Leu Ile Ser Ala Glu Lys Ala
                405                 410                 415

Gly Val Ala Val Thr Asp Arg Gly Phe Ile Glu Val Asp Lys Gln Met
            420                 425                 430

Arg Thr Asn Val Pro His Ile Tyr Ala Ile Gly Asp Ile Val Gly Gln
        435                 440                 445

Pro Met Leu Ala His Lys Ala Val His Glu Gly His Val Ala Ala Glu
    450                 455                 460

Asn Cys Ala Gly His Lys Ala Tyr Phe Asp Ala Arg Val Ile Pro Gly
465                 470                 475                 480

Val Ala Tyr Thr Ser Pro Glu Val Ala Trp Val Gly Glu Thr Glu Leu
                485                 490                 495

Ser Ala Lys Ala Ser Gly Arg Lys Ile Thr Lys Ala Asn Phe Pro Trp
            500                 505                 510

Ala Ala Ser Gly Arg Ala Ile Ala Asn Gly Cys Asp Lys Pro Phe Thr
        515                 520                 525

Lys Leu Ile Phe Asp Ala Glu Thr Gly Arg Ile Ile Gly Gly Gly Ile
    530                 535                 540

Val Gly Pro Asn Gly Gly Asp Met Ile Gly Glu Val Cys Leu Ala Ile
545                 550                 555                 560

Glu Met Gly Cys Asp Ala Ala Asp Ile Gly Lys Thr Ile His Pro His
                565                 570                 575

Pro Gly Glu Ser Ile Gly Met Ala Ala Glu Val Ala Leu Gly Thr Cys
            580                 585                 590

Thr Asp Leu Pro Pro Gln Lys Lys Lys Gly Ser Arg Leu Lys Met Asp
        595                 600                 605

Lys Leu Lys Leu Lys Gly Met Ser Tyr Ala Met Cys Leu Asn Thr Phe
    610                 615                 620

Val Leu Lys Lys Glu Val Ser Glu Thr His Gly Thr Ile Leu Ile Lys
625                 630                 635                 640

Val Glu Tyr Lys Gly Glu Asp Ala Pro Cys Lys Ile Pro Phe Ser Thr
                645                 650                 655

Glu Asp Gly Gln Gly Lys Ala His Asn Gly Arg Leu Ile Thr Ala Asn
            660                 665                 670
```

-continued

```
Pro Val Val Thr Lys Lys Glu Glu Pro Val Asn Ile Glu Ala Glu Pro
        675                 680                 685

Pro Phe Gly Glu Ser Asn Ile Val Ile Gly Ile Gly Asp Lys Ala Leu
    690                 695                 700

Lys Ile Asn Trp Tyr Arg Lys Gly Ser Ser Ile Gly Lys Met Phe Glu
705                 710                 715                 720

Ala Thr Ala Arg Gly Ala Arg Arg Met Ala Ile Leu Gly Asp Thr Ala
                725                 730                 735

Trp Asp Phe Gly Ser Val Gly Gly
            740


<210> SEQ ID NO 46
<211> LENGTH: 426
<212> TYPE: DNA
<213> ORGANISM: Escherichia coli
<220> FEATURE:
<221> NAME/KEY: gene
<222> LOCATION: (1)..(426)
<223> OTHER INFORMATION: Nucleotidic sequence coding for the aminoacids
      286 to 426 of the DEN-4 envelope protein

<400> SEQUENCE: 46

aaagtccgta tggagaaatt gagaatcaag ggaatgtcat acacgatgtg ttcaggaaag     60

ttttcaattg acaaagagat ggcagaaaca cagcatggga caacagtggt gaaagtcaag    120

tatgaaggtg ctggagctcc gtgtaaagtc cccatagaga taagagatgt aaacaaggaa    180

aaagtggttg ggcgtatcat ctcatccacc cctttggctg agaataccaa cagtgtaacc    240

aacatagaat tagaaccccc ctttggggac agctacatag tgataggtgt tggaaacagc    300

gcattaacac tccattggtt caggaaaggg agttccattg gcaagatgtt tgagtccaca    360

tacagaggtg caaaacgaat ggccattcta ggtgaaacag cttgggattt tggttccgtt    420

ggtgga                                                               426


<210> SEQ ID NO 47
<211> LENGTH: 615
<212> TYPE: DNA
<213> ORGANISM: Escherichia coli
<220> FEATURE:
<221> NAME/KEY: gene
<222> LOCATION: (1)..(615)
<223> OTHER INFORMATION: Nucleotidic sequence coding for the quimeric
      protein in the plasmid pID1

<400> SEQUENCE: 47

atgggccacc accaccacca ccacgccatg gtagataaaa gaatggcttt agttgaattg     60

aaagtgcccg acattggcgg aacagaaaat gtagatatta tcgcggttga agtaaacgtg    120

ggcgacacta ttgctgtgga cgataccctg attactttgg atctagattt ggatctagac    180

aaagtgcgta tggagaaatt gagaatcaag ggaatgtcat acacgatgtg ttcaggaaag    240

ttttcaattg acaaagagat ggcagaaaca cagcatggga caacagtggt gaaagtcaag    300

tatgaaggtg ctggagctcc gtgtaaagtc cccatagaga taagagatgt aaacaaggaa    360

aaagtggttg ggcgtatcat ctcatccacc cctttggctg agaataccaa cagtgtaacc    420

aacatagaat tagaaccccc ctttggggac agctacatag tgataggtgt tggaaacagc    480

gcattaacac tccattggtt caggaaaggg agttccattg gcaagatgtt tgagtccaca    540

tacagaggtg caaaacgaat ggccattcta ggtgaaacag cttgggattt tggttccgtt    600

ggtggataag gatcc                                                     615
```

<210> SEQ ID NO 48
<211> LENGTH: 192
<212> TYPE: PRT
<213> ORGANISM: Escherichia coli
<220> FEATURE:
<221> NAME/KEY: CHAIN
<222> LOCATION: (1)..(192)
<223> OTHER INFORMATION: Aminoacidic sequence of the PID1

<400> SEQUENCE: 48

```
His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
         35                  40                  45

Thr Leu Asp Lys Val Arg Met Glu Lys Leu Arg Ile Lys Gly Met Ser
     50                  55                  60

Tyr Thr Met Cys Ser Gly Lys Phe Ser Ile Asp Lys Glu Met Ala Glu
 65                  70                  75                  80

Thr Gln His Gly Thr Thr Val Val Lys Val Lys Tyr Glu Gly Ala Gly
                 85                  90                  95

Ala Pro Cys Lys Val Pro Ile Glu Ile Arg Asp Val Asn Lys Glu Lys
            100                 105                 110

Val Val Gly Arg Ile Ile Ser Ser Thr Pro Leu Ala Glu Asn Thr Asn
        115                 120                 125

Ser Val Thr Asn Ile Glu Leu Glu Arg Pro Leu Asp Ser Tyr Ile Val
    130                 135                 140

Ile Gly Val Gly Asn Ser Ala Leu Thr Leu His Trp Phe Arg Lys Gly
145                 150                 155                 160

Ser Ser Ile Gly Lys Met Phe Glu Ser Thr Tyr Arg Gly Ala Lys Arg
                165                 170                 175

Met Ala Ile Leu Gly Glu Thr Ala Trp Asp Phe Gly Ser Val Gly Gly
            180                 185                 190
```

<210> SEQ ID NO 49
<211> LENGTH: 2241
<212> TYPE: DNA
<213> ORGANISM: Escherichia coli
<220> FEATURE:
<221> NAME/KEY: gene
<222> LOCATION: (1)..(2241)
<223> OTHER INFORMATION: Nucleotidic sequence coding for the quimeric protein in the plasmid pID2

<400> SEQUENCE: 49

```
atgggccacc accaccacca ccacgccatg gtagataaaa gaatggcttt agttgaattg      60

aaagtgcccg acattggcgg aacagaaaat gtagatatta tcgcggttga agtaaacgtg     120

ggcgacacta ttgctgtgga cgataccctg attactttgg atctagacaa agtccgtatg     180

gagaaattga gaatcaaggg aatgtcatac acgatgtgtt caggaaagtt ttcaattgac     240

aaagagatgg cagaaacaca gcatgggaca acagtggtga aagtcaagta tgaaggtgct     300

ggagctccgt gtaaagtccc catagagata agagatgtaa acaaggaaaa agtggttggg     360

cgtatcatct catccacccc tttggctgag aataccaaca gtgtaaccaa catagaatta     420

gaacccccct ttggggacag ctacatagtg ataggtgttg gaaacagcgc attaacactc     480

cattggttca ggaaagggag ttccattggc aagatgtttg agtccacata cagaggtgca     540
```

-continued

```
aaacgaatgg ccattctagg tgaaacagct tgggattttg gtagcgttgg tggactgaat    600

tcgatgaatt cgatggacgt acctgctgaa gttgcaggcg tagtcaaaga agttaaagtt    660

aaagtcggcg acaaaatctc tgaaggtggt ttgattgtcg tcgttgaagc tgaaggcacg    720

gcagccgctc ctaaagccga agcggctgcc gccccggcgc aagaagcccc taaagctgcc    780

gctcctgctc cgcaagccgc gcaattcggc ggttctgccg atgccgagta cgacgtggtc    840

gtattgggtg gcggtcccgg cggttactcc gctgcatttg ccgctgccga tgaaggcttg    900

aaagtcgcca tcgtcgaacg ttacaaaact ttgggcggcg tttgcctgaa cgtcggctgt    960

atcccttcca aagccttgtt gcacaatgcc gccgttatcg acgaagtgcg ccacttggct   1020

gccaacggta tcaaataccc cgagccggaa ctcgacatcg atatgcttcg cgcctacaaa   1080

gacggcgtag tttcccgcct cacgggcggt ttggcaggta tggcgaaaag ccgtaaagtg   1140

gacgttatcc aaggcgacgg gcaattctta gatccgcacc acttggaagt gtcgctgact   1200

gccggcgacg cgtacgaaca ggcagcccct accggcgaga aaaaaatcgt tgccttcaaa   1260

aactgtatca ttgcagcagg cagccgcgta accaaactgc ctttcattcc tgaagatccg   1320

cgcatcatcg attccagcgg cgcattggct ctgaaagaag taccgggcaa actgctgatt   1380

atcggcggcg gcattatcgg cctcgagatg ggtacggttt acagcacgct gggttcgcgt   1440

ttggatgtgg ttgaaatgat ggacggcctg atgcaaggcg cagaccgcga tttggtaaaa   1500

gtatggcaaa aacaaaacga ataccgtttt gacaacatta tggtcaacac caaaaccgtt   1560

gcagttgagc cgaaagaaga cggcgtttac gttacctttg aaggcgcgaa cgcgcctaaa   1620

gagccgcaac gctacgatgc cgtattggtt gccgccggcc gcgcgcccaa cggcaaactc   1680

atcagcgcgg aaaaagcagg cgttgccgta accgatcgcg gcttcatcga agtggacaaa   1740

caaatgcgta ccaatgtgcc gcacatctac gccatcggcg acatcgtcgg tcagccgatg   1800

ttggcgcaca aagccgttca cgaaggccac gttgccgccg aaaactgcgc cggccacaaa   1860

gcctacttcg acgcacgcgt gattccgggc gttgcctaca cttcccccga agtggcgtgg   1920

gtgggcgaaa ccgaactgtc cgccaaagcc tccggccgca aaatcaccaa agccaacttc   1980

ccgtgggcgg cttccggccg tgcgattgcc aacggttgcg acaagccgtt taccaagctg   2040

atttttgatg ccgaaaccgg ccgcatcatc ggcggcggca ttgtcggtcc gaacggtggc   2100

gatatgatcg gcgaagtctg ccttgccatc gaaatgggct gcgacgcggc agacatcggc   2160

aaaaccatcc acccgcaccc gggcgaatcc atcggtatgg cggcggaagt ggcattgggt   2220

acttgtaccg acaaaaaaaa a                                             2241
```

```
<210> SEQ ID NO 50
<211> LENGTH: 747
<212> TYPE: PRT
<213> ORGANISM: Escherichia coli
<220> FEATURE:
<221> NAME/KEY: CHAIN
<222> LOCATION: (1)..(747)
<223> OTHER INFORMATION: Aminoacidic sequence of the PID2

<400> SEQUENCE: 50

His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
         35                  40                  45
```

-continued

```
Thr Leu Asp Leu Asp Lys Val Arg Met Glu Lys Leu Arg Ile Lys Gly
     50                  55                  60

Met Ser Tyr Thr Met Cys Ser Gly Lys Phe Ser Ile Asp Lys Glu Met
 65                  70                  75                  80

Ala Glu Thr Gln His Gly Thr Thr Val Val Lys Val Lys Tyr Glu Gly
                 85                  90                  95

Ala Gly Ala Pro Cys Lys Val Pro Ile Glu Ile Arg Asp Val Asn Lys
            100                 105                 110

Glu Lys Val Val Gly Arg Ile Ile Ser Ser Thr Pro Leu Ala Glu Asn
        115                 120                 125

Thr Asn Ser Val Thr Asn Ile Glu Leu Glu Arg Pro Leu Asp Ser Tyr
    130                 135                 140

Ile Val Ile Gly Val Gly Asn Ser Ala Leu Thr Leu His Trp Phe Arg
145                 150                 155                 160

Lys Gly Ser Ser Ile Gly Lys Met Phe Glu Ser Thr Tyr Arg Gly Ala
                165                 170                 175

Lys Arg Met Ala Ile Leu Gly Glu Thr Ala Trp Asp Phe Gly Ser Val
            180                 185                 190

Gly Gly Leu Asn Ser Met Asn Ser Met Asp Val Pro Ala Glu Val Ala
        195                 200                 205

Gly Val Val Lys Glu Val Lys Val Lys Val Gly Asp Lys Ile Ser Glu
    210                 215                 220

Gly Gly Leu Ile Val Val Val Glu Ala Glu Gly Thr Ala Ala Ala Pro
225                 230                 235                 240

Lys Ala Glu Ala Ala Ala Ala Pro Ala Gln Glu Ala Pro Lys Ala Ala
                245                 250                 255

Ala Pro Ala Pro Gln Ala Ala Gln Phe Gly Gly Ser Ala Asp Ala Glu
            260                 265                 270

Tyr Asp Val Val Val Leu Gly Gly Gly Pro Gly Gly Tyr Ser Ala Ala
        275                 280                 285

Phe Ala Ala Ala Asp Glu Gly Leu Lys Val Ala Ile Val Glu Arg Tyr
    290                 295                 300

Lys Thr Leu Gly Gly Val Cys Leu Asn Val Gly Cys Ile Pro Ser Lys
305                 310                 315                 320

Ala Leu Leu His Asn Ala Ala Val Ile Asp Glu Val Arg His Leu Ala
                325                 330                 335

Ala Asn Gly Ile Lys Tyr Pro Glu Pro Glu Leu Asp Ile Asp Met Leu
            340                 345                 350

Arg Ala Tyr Lys Asp Gly Val Val Ser Arg Leu Thr Gly Gly Leu Ala
        355                 360                 365

Gly Met Ala Lys Ser Arg Lys Val Asp Val Ile Gln Gly Asp Gly Gln
    370                 375                 380

Phe Leu Asp Pro His His Leu Glu Val Ser Leu Thr Ala Gly Asp Ala
385                 390                 395                 400

Tyr Glu Gln Ala Ala Pro Thr Gly Glu Lys Lys Ile Val Ala Phe Lys
                405                 410                 415

Asn Cys Ile Ile Ala Ala Gly Ser Arg Val Thr Lys Leu Pro Phe Ile
            420                 425                 430

Pro Glu Asp Pro Arg Ile Ile Asp Ser Ser Gly Ala Leu Ala Leu Lys
        435                 440                 445

Glu Val Pro Gly Lys Leu Leu Ile Ile Gly Gly Gly Ile Ile Gly Leu
    450                 455                 460

Glu Met Gly Thr Val Tyr Ser Thr Leu Gly Ser Arg Leu Asp Val Val
```

-continued

```
465                 470                 475                 480

Glu Met Met Asp Gly Leu Met Gln Gly Ala Asp Arg Asp Leu Val Lys
                485                 490                 495

Val Trp Gln Lys Gln Asn Glu Tyr Arg Phe Asp Asn Ile Met Val Asn
            500                 505                 510

Thr Lys Thr Val Ala Val Glu Pro Lys Glu Asp Gly Val Tyr Val Thr
        515                 520                 525

Phe Glu Gly Ala Asn Ala Pro Lys Glu Pro Gln Arg Tyr Asp Ala Val
    530                 535                 540

Leu Val Ala Ala Gly Arg Ala Pro Asn Gly Lys Leu Ile Ser Ala Glu
545                 550                 555                 560

Lys Ala Gly Val Ala Val Thr Asp Arg Gly Phe Ile Glu Val Asp Lys
                565                 570                 575

Gln Met Arg Thr Asn Val Pro His Ile Tyr Ala Ile Gly Asp Ile Val
            580                 585                 590

Gly Gln Pro Met Leu Ala His Lys Ala Val His Glu Gly His Val Ala
        595                 600                 605

Ala Glu Asn Cys Ala Gly His Lys Ala Tyr Phe Asp Ala Arg Val Ile
    610                 615                 620

Pro Gly Val Ala Tyr Thr Ser Pro Glu Val Ala Trp Val Gly Glu Thr
625                 630                 635                 640

Glu Leu Ser Ala Lys Ala Ser Gly Arg Lys Ile Thr Lys Ala Asn Phe
                645                 650                 655

Pro Trp Ala Ala Ser Gly Arg Ala Ile Ala Asn Gly Cys Asp Lys Pro
            660                 665                 670

Phe Thr Lys Leu Ile Phe Asp Ala Glu Thr Gly Arg Ile Ile Gly Gly
        675                 680                 685

Gly Ile Val Gly Pro Asn Gly Gly Asp Met Ile Gly Glu Val Cys Leu
    690                 695                 700

Ala Ile Glu Met Gly Cys Asp Ala Ala Asp Ile Gly Lys Thr Ile His
705                 710                 715                 720

Pro His Pro Gly Glu Ser Ile Gly Met Ala Ala Glu Val Ala Leu Gly
                725                 730                 735

Thr Cys Thr Asp Leu Pro Pro Gln Lys Lys Lys
            740                 745


<210> SEQ ID NO 51
<211> LENGTH: 2256
<212> TYPE: DNA
<213> ORGANISM: Escherichia coli
<220> FEATURE:
<221> NAME/KEY: gene
<222> LOCATION: (1)..(2256)
<223> OTHER INFORMATION: Nucleotidic sequence coding for the quimeric
      protein in the plasmid pID3

<400> SEQUENCE: 51

atgggccacc accaccacca ccacgccatg gtagataaaa gaatggcttt agttgaattg      60

aaagtgcccg acattggcgg acacgaaaat gtagatatta tcgcggttga agtaaacgtg     120

ggcgacacta ttgctgtgga cgataccctg attactttgg atctagaaat ggacgtacct     180

gctgaagttg caggcgtagt caaagaagtt aaagttaaag tcggcgacaa aatctctgaa     240

ggtggtttga ttgtcgtcgt tgaagctgaa ggcacggcag ccgctcctaa agccgaagcg     300

gctgccgccc cggcgcaaga agcccctaaa gctgccgctc ctgctccgca agccgcgcaa     360

ttcggcggtt ctgccgatgc cgagtacgac gtggtcgtat tgggtggcgg tcccggcggt     420
```

-continued

```
tactccgctg catttgccgc tgccgatgaa ggcttgaaag tcgccatcgt cgaacgttac    480

aaaactttgg gcggcgtttg cctgaacgtc ggctgtatcc cttccaaagc cttgttgcac    540

aatgccgccg ttatcgacga agtgcgccac ttggctgcca acggtatcaa ataccccgag    600

ccggaactcg acatcgatat gcttcgcgcc tacaaagacg gcgtagtttc ccgcctcacg    660

ggcggtttgg caggtatggc gaaaagccgt aaagtggacg ttatccaagg cgacgggcaa    720

ttcttagatc cgcaccactt ggaagtgtcg ctgactgccg gcgacgcgta cgaacaggca    780

gcccctaccg gcgagaaaaa aatcgttgcc ttcaaaaact gtatcattgc agcaggcagc    840

cgcgtaacca aactgccttt cattcctgaa gatccgcgca tcatcgattc cagcggcgca    900

ttggctctga aagaagtacc gggcaaactg ctgattatcg gcggcggcat tatcggcctc    960

gagatgggta cggtttacag cacgctgggt tcgcgtttgg atgtggttga aatgatggac   1020

ggcctgatgc aaggcgcaga ccgcgatttg gtaaaagtat ggcaaaaaca aaacgaatac   1080

cgttttgaca acattatggt caacaccaaa accgttgcag ttgagccgaa agaagacggc   1140

gtttacgtta cctttgaagg cgcgaacgcg cctaaagagc cgcaacgcta cgatgccgta   1200

ttggttgccg ccggccgcgc gcccaacggc aaactcatca gcgcggaaaa agcaggcgtt   1260

gccgtaaccg atcgcggctt catcgaagtg gacaaacaaa tgcgtaccaa tgtgccgcac   1320

atctacgcca tcggcgacat cgtcggtcag ccgatgttgg cgcacaaagc cgttcacgaa   1380

ggccacgttg ccgccgaaaa ctgcgccggc cacaaagcct acttcgacgc acgcgtgatt   1440

ccgggcgttg cctacacttc ccccgaagtg gcgtgggtgg gcgaaaccga actgtccgcc   1500

aaagcctccg gccgcaaaat caccaaagcc aacttcccgt gggcggcttc cggccgtgcg   1560

attgccaacg gttgcgacaa gccgtttacc aagctgattt ttgatgccga aaccggccgc   1620

atcatcggcg gcggcattgt cggtccgaac ggtggcgata tgatcggcga agtctgcctt   1680

gccatcgaaa tgggctgcga cgcggcagac atcggcaaaa ccatccaccc gcacccgacc   1740

ttgggcgaat ccatcggtat ggcggcggaa gtggcattgg gtacttgtac cgacctgcct   1800

ccgcaaaaga aaaaaggatc caaagtgcgt atggagaaat tgagaatcaa gggaatgtca   1860

tacacgatgt gttcaggaaa gttttcaatt gacaaagaga tggcagaaac acagcatggg   1920

acaacagtgg tgaaagtcaa gtatgaaggt gctggagctc cgtgtaaagt ccccatagag   1980

ataagagatg taaacaagga aaaagtggtt gggcgtatca tctcatccac ccctttggct   2040

gagaatacca acagtgtaac caacatagaa ttagaacccc cctttgggga cagctacata   2100

gtgataggtg ttggaaacag cgcattaaca ctccattggt tcaggaaagg gagttccatt   2160

ggcaagatgt ttgagtccac atacagaggt gcaaaacgaa tggccattct aggtgaaaca   2220

gcttgggatt ttggttcggt tggtggctaa ggatcc                             2256
```

<210> SEQ ID NO 52
<211> LENGTH: 744
<212> TYPE: PRT
<213> ORGANISM: Escherichia coli
<220> FEATURE:
<221> NAME/KEY: CHAIN
<222> LOCATION: (1)..(744)
<223> OTHER INFORMATION: Aminoacidic sequence of the PID3

<400> SEQUENCE: 52

```
His His His His His His Met Val Asp Lys Arg Met Ala Leu Val Glu
 1               5                  10                  15

Leu Lys Val Pro Asp Ile Gly Gly His Glu Asn Val Asp Ile Ile Ala
```

```
            20                  25                  30

Val Glu Val Asn Val Gly Asp Thr Ile Ala Val Asp Asp Thr Leu Ile
        35                  40                  45

Thr Leu Asp Met Asn Ser Met Asp Val Pro Ala Glu Val Ala Gly Val
    50                  55                  60

Val Lys Glu Val Lys Val Lys Val Gly Asp Lys Ile Ser Glu Gly Gly
65                  70                  75                  80

Leu Ile Val Val Val Glu Ala Glu Gly Thr Ala Ala Ala Pro Lys Ala
                85                  90                  95

Glu Ala Ala Ala Ala Pro Ala Gln Glu Ala Pro Lys Ala Ala Ala Pro
            100                 105                 110

Ala Pro Gln Ala Ala Gln Phe Gly Gly Ser Ala Asp Ala Glu Tyr Asp
        115                 120                 125

Val Val Val Leu Gly Gly Gly Pro Gly Gly Tyr Ser Ala Ala Phe Ala
    130                 135                 140

Ala Ala Asp Glu Gly Leu Lys Val Ala Ile Val Glu Arg Tyr Lys Thr
145                 150                 155                 160

Leu Gly Gly Val Cys Leu Asn Val Gly Cys Ile Pro Ser Lys Ala Leu
                165                 170                 175

Leu His Asn Ala Ala Val Ile Asp Glu Val Arg His Leu Ala Ala Asn
            180                 185                 190

Gly Ile Lys Tyr Pro Glu Pro Glu Leu Asp Ile Asp Met Leu Arg Ala
        195                 200                 205

Tyr Lys Asp Gly Val Val Ser Arg Leu Thr Gly Gly Leu Ala Gly Met
    210                 215                 220

Ala Lys Ser Arg Lys Val Asp Val Ile Gln Gly Asp Gly Gln Phe Leu
225                 230                 235                 240

Asp Pro His His Leu Glu Val Ser Leu Thr Ala Gly Asp Ala Tyr Glu
                245                 250                 255

Gln Ala Ala Pro Thr Gly Glu Lys Lys Ile Val Ala Phe Lys Asn Cys
            260                 265                 270

Ile Ile Ala Ala Gly Ser Arg Val Thr Lys Leu Pro Phe Ile Pro Glu
        275                 280                 285

Asp Pro Arg Ile Ile Asp Ser Ser Gly Ala Leu Ala Leu Lys Glu Val
    290                 295                 300

Pro Gly Lys Leu Leu Ile Ile Gly Gly Gly Ile Ile Gly Leu Glu Met
305                 310                 315                 320

Gly Thr Val Tyr Ser Thr Leu Gly Ser Arg Leu Asp Val Val Glu Met
                325                 330                 335

Met Asp Gly Leu Met Gln Gly Ala Asp Arg Asp Leu Val Lys Val Trp
            340                 345                 350

Gln Lys Gln Asn Glu Tyr Arg Phe Asp Asn Ile Met Val Asn Thr Lys
        355                 360                 365

Thr Val Ala Val Glu Pro Lys Glu Asp Gly Val Tyr Val Thr Phe Glu
    370                 375                 380

Gly Ala Asn Ala Pro Lys Glu Pro Gln Arg Tyr Asp Ala Val Leu Val
385                 390                 395                 400

Ala Ala Gly Arg Ala Pro Asn Gly Lys Leu Ile Ser Ala Glu Lys Ala
                405                 410                 415

Gly Val Ala Val Thr Asp Arg Gly Phe Ile Glu Val Asp Lys Gln Met
            420                 425                 430

Arg Thr Asn Val Pro His Ile Tyr Ala Ile Gly Asp Ile Val Gly Gln
        435                 440                 445
```

```
Pro Met Leu Ala His Lys Ala Val His Glu Gly His Val Ala Ala Glu
    450                 455                 460

Asn Cys Ala Gly His Lys Ala Tyr Phe Asp Ala Arg Val Ile Pro Gly
465                 470                 475                 480

Val Ala Tyr Thr Ser Pro Glu Val Ala Trp Val Gly Glu Thr Glu Leu
                485                 490                 495

Ser Ala Lys Ala Ser Gly Arg Lys Ile Thr Lys Ala Asn Phe Pro Trp
            500                 505                 510

Ala Ala Ser Gly Arg Ala Ile Ala Asn Gly Cys Asp Lys Pro Phe Thr
        515                 520                 525

Lys Leu Ile Phe Asp Ala Glu Thr Gly Arg Ile Ile Gly Gly Gly Ile
    530                 535                 540

Val Gly Pro Asn Gly Gly Asp Met Ile Gly Glu Val Cys Leu Ala Ile
545                 550                 555                 560

Glu Met Gly Cys Asp Ala Ala Asp Ile Gly Lys Thr Ile His Pro His
                565                 570                 575

Pro Gly Glu Ser Ile Gly Met Ala Ala Glu Val Ala Leu Gly Thr Cys
            580                 585                 590

Thr Asp Leu Pro Pro Gln Lys Lys Lys Gly Ser Lys Val Arg Met Glu
        595                 600                 605

Lys Leu Arg Ile Lys Gly Met Ser Tyr Thr Met Cys Ser Gly Lys Phe
    610                 615                 620

Ser Ile Asp Lys Glu Met Ala Glu Thr Gln His Gly Thr Thr Val Val
625                 630                 635                 640

Lys Val Lys Tyr Glu Gly Ala Gly Ala Pro Cys Lys Val Pro Ile Glu
                645                 650                 655

Ile Arg Asp Val Asn Lys Glu Lys Val Val Gly Arg Ile Ile Ser Ser
            660                 665                 670

Thr Pro Leu Ala Glu Asn Thr Asn Ser Val Thr Asn Ile Glu Leu Glu
        675                 680                 685

Arg Pro Leu Asp Ser Tyr Ile Val Ile Gly Val Gly Asn Ser Ala Leu
    690                 695                 700

Thr Leu His Trp Phe Arg Lys Gly Ser Ser Ile Gly Lys Met Phe Glu
705                 710                 715                 720

Ser Thr Tyr Arg Gly Ala Lys Arg Met Ala Ile Leu Gly Glu Thr Ala
                725                 730                 735

Trp Asp Phe Gly Ser Val Gly Gly
            740
```

<210> SEQ ID NO 53
<211> LENGTH: 2694
<212> TYPE: DNA
<213> ORGANISM: Escherichia coli
<220> FEATURE:
<221> NAME/KEY: gene
<222> LOCATION: (1)..(2694)
<223> OTHER INFORMATION: Nucleotidic sequence coding for the quimeric protein in the plasmid pD4D2

<400> SEQUENCE: 53

```
atgggccacc accaccacca ccacgccatg gtagataaaa gaatggcttt agttgaattg     60

aaagtgcccg acattggcgg acacgaaaat gtagatatta tcgcggttga agtaaacgtg    120

ggcgacacta ttgctgtgga cgataccctg attactttgg atctagacaa agtccgtatg    180

gagaaattga gaatcaaggg aatgtcatac acgatgtgtt caggaaagtt ttcaattgac    240
```

-continued

```
aaagagatgg cagaaacaca gcatgggaca acagtggtga aagtcaagta tgaaggtgct    300
ggagctccgt gtaaagtccc catagagata agagatgtaa acaaggaaaa agtggttggg    360
cgtatcatct catccacccc tttggctgag aataccaaca gtgtaaccaa catagaatta    420
gaaccccct ttggggacag ctacatagtg ataggtgttg gaaacagcgc attaacactc    480
cattggttca ggaaagggag ttccattggc aagatgtttg agtccacata cagaggtgca    540
aaacgaatgg ccattctagg tgaaacagct tgggattttg gttccgttgg tggtcttcta    600
gaaatggacg tacctgctga agttgcaggc gtagtcaaag aagttaaagt taaagtcggc    660
gacaaaatct ctgaaggtgg tttgattgtc gtcgttgaag ctgaaggcac ggcagccgct    720
cctaaagccg aagcggctgc cgccccggcg caagaagccc ctaaagctgc cgctcctgct    780
ccgcaagccg cgcaattcgg cggttctgcc gatgccgagt acgacgtggt cgtattgggt    840
ggcggtcccg gcggttactc cgctgcattt gccgctgccg atgaaggctt gaaagtcgcc    900
atcgtcgaac gttacaaaac tttgggcggc gtttgcctga acgtcggctg tatcccttcc    960
aaagccttgt tgcacaatgc cgccgttatc gacgaagtgc gccacttggc tgccaacggt   1020
atcaaatacc ccgagccgga actcgacatc gatatgcttc gcgcctacaa agacggcgta   1080
gtttcccgcc tcacgggcgg tttggcaggt atggcgaaaa gccgtaaagt ggacgttatc   1140
caaggcgacg ggcaattctt agatccgcac cacttggaag tgtcgctgac tgccggcgac   1200
gcgtacgaac aggcagcccc taccggcgag aaaaaaatcg ttgccttcaa aaactgtatc   1260
attgcagcag gcagccgcgt aaccaaactg cctttcattc ctgaagatcc gcgcatcatc   1320
gattccagcg gcgcattggc tctgaaagaa gtaccgggca aactgctgat tatcggcggc   1380
ggcattatcg gcctcgagat gggtacggtt tacagcacgc tgggttcgcg tttggatgtg   1440
gttgaaatga tggacggcct gatgcaaggc gcagaccgcg atttggtaaa agtatggcaa   1500
aaacaaaacg aataccgttt tgacaacatt atggtcaaca ccaaaaccgt tgcagttgag   1560
ccgaaagaag acggcgttta cgttaccttt gaaggcgcga acgcgcctaa agagccgcaa   1620
cgctacgatg ccgtattggt tgccgccggc cgcgcgccca acggcaaact catcagcgcg   1680
gaaaaagcag gcgttgccgt aaccgatcgc ggcttcatcg aagtggacaa acaaatgcgt   1740
accaatgtgc cgcacatcta cgccatcggc gacatcgtcg gtcagccgat gttggcgcac   1800
aaagccgttc acgaaggcca cgttgccgcc gaaaactgcg ccggccacaa agcctacttc   1860
gacgcacgcg tgattccggg cgttgcctac acttccccccg aagtggcgtg ggtgggcgaa   1920
accgaactgt ccgccaaagc ctccggccgc aaaatcacca aagccaactt cccgtgggcg   1980
gcttccggcc gtgcgattgc caacggttgc gacaagccgt ttaccaagct gatttttgat   2040
gccgaaaccg gccgcatcat cggcggcggc attgtcggtc cgaacggtgg cgatatgatc   2100
ggcgaagtct gccttgccat cgaaatgggc tgcgacgcgg cagacatcgg caaaaccatc   2160
cacccgcacc cgaccttggg cgaatccatc ggtatggcgg cggaagtggc attgggtact   2220
tgtaccgacc tgcctccgca aaagaaaaaa ggatccgaca ggctgagaat ggacaaacta   2280
cagctcaaag gaatgtcata ctctatgtgt acaggaaagt ttaaaattgt gaaggaaata   2340
gcagaaacac aacatggaac aatagttatc agagtacaat atgaagggga cggctctcca   2400
tgtaagatcc cttttgagat aatggatttg gaaaaaagac acgtcttagg tcgcctgatt   2460
acagttaacc cgatcgtaac agaaaaagat agcccagtca acatagaagc agaacctcca   2520
ttcggagaca gctacatcat cataggagta gagccgggac aattgaaact caactggttt   2580
aagaaaggaa gttccatcgg ccaaatgttt gagacaacaa tgagaggagc gaagagaatg   2640
```

gccattttag gtgacacagc ctgggatttt gggtctctgg gtggttaagg atcc 2694

<210> SEQ ID NO 54
<211> LENGTH: 891
<212> TYPE: PRT
<213> ORGANISM: Escherichia coli
<220> FEATURE:
<221> NAME/KEY: CHAIN
<222> LOCATION: (1)..(891)
<223> OTHER INFORMATION: Aminoacidic sequence of the PD4D2

<400> SEQUENCE: 54

```
His His His His His His Met Val Asp Lys Arg Met Ala Leu Val Glu
  1               5                  10                  15

Leu Lys Val Pro Asp Ile Gly Gly His Glu Asn Val Asp Ile Ile Ala
             20                  25                  30

Val Glu Val Asn Val Gly Asp Thr Ile Ala Val Asp Asp Thr Leu Ile
         35                  40                  45

Thr Leu Asp Leu Asp Lys Val Arg Met Glu Lys Leu Arg Ile Lys Gly
     50                  55                  60

Met Ser Tyr Thr Met Cys Ser Gly Lys Phe Ser Ile Asp Lys Glu Met
 65                  70                  75                  80

Ala Glu Thr Gln His Gly Thr Thr Val Val Lys Val Lys Tyr Glu Gly
                 85                  90                  95

Ala Gly Ala Pro Cys Lys Val Pro Ile Glu Ile Arg Asp Val Asn Lys
            100                 105                 110

Glu Lys Val Val Gly Arg Ile Ile Ser Ser Thr Pro Leu Ala Glu Asn
        115                 120                 125

Thr Asn Ser Val Thr Asn Ile Glu Leu Glu Arg Pro Leu Asp Ser Tyr
    130                 135                 140

Ile Val Ile Gly Val Gly Asn Ser Ala Leu Thr Leu His Trp Phe Arg
145                 150                 155                 160

Lys Gly Ser Ser Ile Gly Lys Met Phe Glu Ser Thr Tyr Arg Gly Ala
                165                 170                 175

Lys Arg Met Ala Ile Leu Gly Glu Thr Ala Trp Asp Phe Gly Ser Val
            180                 185                 190

Gly Gly Leu Leu Glu Met Asn Ser Met Asp Val Pro Ala Glu Val Ala
        195                 200                 205

Gly Val Val Lys Glu Val Lys Val Lys Val Gly Asp Lys Ile Ser Glu
    210                 215                 220

Gly Gly Leu Ile Val Val Val Glu Ala Glu Gly Thr Ala Ala Ala Pro
225                 230                 235                 240

Lys Ala Glu Ala Ala Ala Ala Pro Ala Gln Glu Ala Pro Lys Ala Ala
                245                 250                 255

Ala Pro Ala Pro Gln Ala Ala Gln Phe Gly Gly Ser Ala Asp Ala Glu
            260                 265                 270

Tyr Asp Val Val Val Leu Gly Gly Gly Pro Gly Gly Tyr Ser Ala Ala
        275                 280                 285

Phe Ala Ala Ala Asp Glu Gly Leu Lys Val Ala Ile Val Glu Arg Tyr
    290                 295                 300

Lys Thr Leu Gly Gly Val Cys Leu Asn Val Gly Cys Ile Pro Ser Lys
305                 310                 315                 320

Ala Leu Leu His Asn Ala Ala Val Ile Asp Glu Val Arg His Leu Ala
                325                 330                 335

Ala Asn Gly Ile Lys Tyr Pro Glu Pro Glu Leu Asp Ile Asp Met Leu
```

-continued

```
            340                 345                 350

Arg Ala Tyr Lys Asp Gly Val Val Ser Arg Leu Thr Gly Gly Leu Ala
        355                 360                 365

Gly Met Ala Lys Ser Arg Lys Val Asp Val Ile Gln Gly Asp Gly Gln
    370                 375                 380

Phe Leu Asp Pro His His Leu Glu Val Ser Leu Thr Ala Gly Asp Ala
385                 390                 395                 400

Tyr Glu Gln Ala Ala Pro Thr Gly Glu Lys Lys Ile Val Ala Phe Lys
                405                 410                 415

Asn Cys Ile Ile Ala Ala Gly Ser Arg Val Thr Lys Leu Pro Phe Ile
            420                 425                 430

Pro Glu Asp Pro Arg Ile Ile Asp Ser Ser Gly Ala Leu Ala Leu Lys
        435                 440                 445

Glu Val Pro Gly Lys Leu Leu Ile Ile Gly Gly Gly Ile Ile Gly Leu
    450                 455                 460

Glu Met Gly Thr Val Tyr Ser Thr Leu Gly Ser Arg Leu Asp Val Val
465                 470                 475                 480

Glu Met Met Asp Gly Leu Met Gln Gly Ala Asp Arg Asp Leu Val Lys
                485                 490                 495

Val Trp Gln Lys Gln Asn Glu Tyr Arg Phe Asp Asn Ile Met Val Asn
            500                 505                 510

Thr Lys Thr Val Ala Val Glu Pro Lys Glu Asp Gly Val Tyr Val Thr
        515                 520                 525

Phe Glu Gly Ala Asn Ala Pro Lys Glu Pro Gln Arg Tyr Asp Ala Val
    530                 535                 540

Leu Val Ala Ala Gly Arg Ala Pro Asn Gly Lys Leu Ile Ser Ala Glu
545                 550                 555                 560

Lys Ala Gly Val Ala Val Thr Asp Arg Gly Phe Ile Glu Val Asp Lys
                565                 570                 575

Gln Met Arg Thr Asn Val Pro His Ile Tyr Ala Ile Gly Asp Ile Val
            580                 585                 590

Gly Gln Pro Met Leu Ala His Lys Ala Val His Glu Gly His Val Ala
        595                 600                 605

Ala Glu Asn Cys Ala Gly His Lys Ala Tyr Phe Asp Ala Arg Val Ile
    610                 615                 620

Pro Gly Val Ala Tyr Thr Ser Pro Glu Val Ala Trp Val Gly Glu Thr
625                 630                 635                 640

Glu Leu Ser Ala Lys Ala Ser Gly Arg Lys Ile Thr Lys Ala Asn Phe
                645                 650                 655

Pro Trp Ala Ala Ser Gly Arg Ala Ile Ala Asn Gly Cys Asp Lys Pro
            660                 665                 670

Phe Thr Lys Leu Ile Phe Asp Ala Glu Thr Gly Arg Ile Ile Gly Gly
        675                 680                 685

Gly Ile Val Gly Pro Asn Gly Gly Asp Met Ile Gly Glu Val Cys Leu
    690                 695                 700

Ala Ile Glu Met Gly Cys Asp Ala Ala Asp Ile Gly Lys Thr Ile His
705                 710                 715                 720

Pro His Pro Gly Glu Ser Ile Gly Met Ala Ala Glu Val Ala Leu Gly
                725                 730                 735

Thr Cys Thr Asp Leu Pro Pro Gln Lys Lys Lys Gly Ser Arg Leu Arg
            740                 745                 750

Met Asp Lys Leu Gln Leu Lys Gly Met Ser Tyr Ser Met Cys Thr Gly
        755                 760                 765
```

-continued

```
Lys Phe Lys Ile Val Lys Glu Ile Ala Glu Thr Gln His Gly Thr Ile
    770                 775                 780

Val Ile Arg Val Gln Tyr Glu Gly Asp Gly Ser Pro Cys Lys Ile Pro
785                 790                 795                 800

Phe Glu Ile Met Asp Leu Glu Lys Arg His Val Leu Gly Arg Leu Ile
                805                 810                 815

Thr Val Asn Pro Ile Val Thr Glu Lys Asp Ser Pro Val Asn Ile Glu
            820                 825                 830

Ala Glu Pro Pro Phe Gly Asp Ser Tyr Ile Ile Ile Gly Val Glu Pro
        835                 840                 845

Gly Gln Leu Lys Leu Asn Trp Phe Lys Lys Gly Ser Ser Ile Gly Gln
    850                 855                 860

Met Phe Glu Thr Thr Met Arg Gly Ala Lys Arg Met Ala Ile Leu Gly
865                 870                 875                 880

Asp Thr Ala Trp Asp Phe Gly Ser Leu Gly Gly
                885                 890
```